United States Patent
Garzon et al.

(10) Patent No.: US 10,787,665 B2
(45) Date of Patent: Sep. 29, 2020

(54) ANTISENSE OLIGOMERS TARGETING HOXB-AS3 LONG NON-CODING RNA

(71) Applicants: Ohio State Innovation Foundation, Columbus, OH (US); Aalborg University, Aalborg (DK)

(72) Inventors: Ramiro Garzon, Upper Arlington, OH (US); Adrienne Dorrance, Columbus, OH (US); Dimitrios Papaioannou, Columbus, OH (US); Robert Lee, Lewis Center, OH (US); Sakari Kauppinen, Holte (DK); Andreas Petri, Frederiksberg C (DK); Charlotte Albæk Thrue, Carcavelos (PT)

(73) Assignees: Ohio State Innovation Foundation, Columbus, OH (US); Aalborg University, Aalborg (DK)

( * ) Notice: Subject to any disclaimer, the term of this patent is extended or adjusted under 35 U.S.C. 154(b) by 0 days.

(21) Appl. No.: 16/347,311

(22) PCT Filed: Nov. 3, 2017

(86) PCT No.: PCT/US2017/059932
§ 371 (c)(1),
(2) Date: May 3, 2019

(87) PCT Pub. No.: WO2018/085656
PCT Pub. Date: May 11, 2018

(65) Prior Publication Data
US 2019/0256848 A1 Aug. 22, 2019

Related U.S. Application Data

(60) Provisional application No. 62/416,993, filed on Nov. 3, 2016.

(51) Int. Cl.
| | | |
|---|---|---|
| C07H 21/04 | (2006.01) | |
| C12N 15/113 | (2010.01) | |
| A61K 31/712 | (2006.01) | |
| A61K 45/06 | (2006.01) | |
| A61K 31/7125 | (2006.01) | |
| A61P 35/02 | (2006.01) | |
| A61K 9/127 | (2006.01) | |

(52) U.S. Cl.
CPC .......... *C12N 15/113* (2013.01); *A61K 31/712* (2013.01); *A61K 31/7125* (2013.01); *A61K 45/06* (2013.01); *A61P 35/02* (2018.01); *C12N 15/1135* (2013.01); *A61K 9/127* (2013.01); *C12N 2310/113* (2013.01); *C12N 2310/315* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | | |
|---|---|---|---|---|
| 7,235,653 B2* | 6/2007 | Bennett | ............... | A61K 31/711 |
| | | | | 536/24.3 |
| 7,585,847 B2* | 9/2009 | Bratzler | ............... | A61K 31/138 |
| | | | | 424/130.1 |
| 8,563,528 B2 | 10/2013 | Straarup et al. | | |
| 9,506,060 B2 | 11/2016 | Bandaru et al. | | |
| 2009/0292006 A1* | 11/2009 | Bhanot | ............. | C12N 15/1137 |
| | | | | 514/44 A |
| 2014/0142160 A1 | 5/2014 | Lee et al. | | |

OTHER PUBLICATIONS

Wei, Shuyong, and Kankan Wang. "Long noncoding RNAs: pivotal regulators in acute myeloid leukemia." Experimental hematology & oncology 5.1 (2015): 30.*
Kanehisa (1984) "Use of statistical criteria for screening potential homologies in nucleic acid sequences", Nucl. Acids Res. 12:203.
McHugh CA, Chen CK, Chow Al et al. The Xist lncRNA interacts directly with SHARP to silence transcription through HDAC3. Nature, 2015;521(7551):232-236.
O'Sullivan AC, Sullivan GJ, McStay B. UBF binding in vivo is not restricted to regulatory sequences within the vertebrate ribosomal DNA repeat. Mol Cell Biol. 2002;22(2):657-668.
International Preliminary Report on Patentability issued for Application No. PCT/US201/059932, dated May 16, 2019, 7 pages.
International Search Report and Written Opinion. Issued by the International Searching Authority (US) in PCT Application No. PCT/US2017/059932 dated Feb. 6, 2018. 11 pages.
Garzon, Ramiro, et al. "Expression and prognostic impact of lncRNAs in acute myeloid leukemia." Proceedings of the National Academy of Sciences 111.52 (2014): 18679-18684.

* cited by examiner

*Primary Examiner* — Kimberly Chong
(74) *Attorney, Agent, or Firm* — Meunier Carlin & Curfman LLC

(57) ABSTRACT

The present disclosure relates to antisense oligomers targeting the long non-coding RNA HOXB-AS3 and methods of treating acute myeloid leukemia.

16 Claims, 30 Drawing Sheets
Specification includes a Sequence Listing.

Dose i.v: 5mg/kg of scramble or anti-*HOXB-AS3* LNAs
Dose i.p.: 10mg/kg of scramble or anti-*HOXB-AS3* LNAs

SEQUENCE LISTING

```
<160> NUMBER OF SEQ ID NOS: 33

<210> SEQ ID NO 1
<211> LENGTH: 17
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(2)
<223> OTHER INFORMATION: locked nucleic acid modified bases
<220> FEATURE:
<221> NAME/KEY: misc_feature
<222> LOCATION: (1)..(3)
<223> OTHER INFORMATION: phosphorothioated bonds among bases
<220> FEATURE:
<221> NAME/KEY: misc_feature
<222> LOCATION: (4)..(4)
```

```
<223> OTHER INFORMATION: deoxyCytidine substituted with
      methyl-deoxyCytidine
<220> FEATURE:
<221> NAME/KEY: misc_feature
<222> LOCATION: (5)..(8)
<223> OTHER INFORMATION: phosphorothioated bonds among bases
<220> FEATURE:
<221> NAME/KEY: misc_feature
<222> LOCATION: (9)..(9)
<223> OTHER INFORMATION: deoxyCytidine substituted with
      methyl-deoxyCytidine
<220> FEATURE:
<221> NAME/KEY: misc_feature
<222> LOCATION: (10)..(16)
<223> OTHER INFORMATION: phosphorothioated bonds among bases
<220> FEATURE:
<221> NAME/KEY: misc_feature
<222> LOCATION: (16)..(17)
<223> OTHER INFORMATION: locked nucleic acid modified bases

<400> SEQUENCE: 1
cggngcatng agatcgc                                                    17

<210> SEQ ID NO 2
<211> LENGTH: 17
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(2)
<223> OTHER INFORMATION: locked nucleic acid modified bases
<220> FEATURE:
<221> NAME/KEY: misc_feature
<222> LOCATION: (1)..(17)
<223> OTHER INFORMATION: phosphorothioated bonds among bases
<220> FEATURE:
<221> NAME/KEY: misc_feature
<222> LOCATION: (15)..(17)
<223> OTHER INFORMATION: locked nucleic acid modified bases

<400> SEQUENCE: 2
ggagggaatt gtagcga                                                    17

<210> SEQ ID NO 3
<211> LENGTH: 19
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(2)
<223> OTHER INFORMATION: locked nucleic acid modified bases
<220> FEATURE:
<221> NAME/KEY: misc_feature
<222> LOCATION: (1)..(2)
<223> OTHER INFORMATION: phosphorothioated bonds among bases
<220> FEATURE:
<221> NAME/KEY: misc_feature
<222> LOCATION: (3)..(3)
<223> OTHER INFORMATION: deoxyCytidine substituted with
      methyl-deoxyCytidine
<220> FEATURE:
<221> NAME/KEY: misc_feature
<222> LOCATION: (4)..(18)
<223> OTHER INFORMATION: phosphorothioated bonds among bases
<220> FEATURE:
<221> NAME/KEY: misc_feature
<222> LOCATION: (18)..(19)
<223> OTHER INFORMATION: locked nucleic acid modified bases

<400> SEQUENCE: 3
```
tgngttgtat tggtatggg                                              19

<210> SEQ ID NO 4
<211> LENGTH: 17
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(2)
<223> OTHER INFORMATION: locked nucleic acid modified bases
<220> FEATURE:
<221> NAME/KEY: misc_feature
<222> LOCATION: (1)..(16)
<223> OTHER INFORMATION: phosphorothioated bonds among bases
<220> FEATURE:
<221> NAME/KEY: misc_feature
<222> LOCATION: (15)..(17)
<223> OTHER INFORMATION: locked nucleic acid modified bases

<400> SEQUENCE: 4
ggggaggtta tttcgtt                                                17

<210> SEQ ID NO 5
<211> LENGTH: 19
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(3)
<223> OTHER INFORMATION: locked nucleic acid modified bases
<220> FEATURE:
<221> NAME/KEY: misc_feature
<222> LOCATION: (1)..(12)
<223> OTHER INFORMATION: phosphorothioated bonds among bases
<220> FEATURE:
<221> NAME/KEY: misc_feature
<222> LOCATION: (13)..(13)
<223> OTHER INFORMATION: deoxyCytidine substituted with
      methyl-deoxyCytidine
<220> FEATURE:
<221> NAME/KEY: misc_feature
<222> LOCATION: (14)..(18)
<223> OTHER INFORMATION: phosphorothioated bonds among bases
<220> FEATURE:
<221> NAME/KEY: misc_feature
<222> LOCATION: (18)..(19)
<223> OTHER INFORMATION: locked nucleic acid modified bases

<400> SEQUENCE: 5
ttctattact tgngttgta                                              19

<210> SEQ ID NO 6
<211> LENGTH: 16
<212> TYPE: DNA
<213> ORGANISM: Artificial Sequence
<220> FEATURE:
<223> OTHER INFORMATION: artificial construct
<220> FEATURE:
<221> NAME/KEY: misc_feature
<222> LOCATION: (1)..(3)
<223> OTHER INFORMATION: locked nucleic acid modified bases
<220> FEATURE:
<221> NAME/KEY: misc_feature
<222> LOCATION: (1)..(16)
<223> OTHER INFORMATION: phosphorothioated bonds among bases
<220> FEATURE:
<221> NAME/KEY: misc_feature
<222> LOCATION: (14)..(16)
<223> OTHER INFORMATION: locked nucleic acid modified bases

```
<400> SEQUENCE: 6
cgaatagtta gtagcg                                                      16

<210> SEQ ID NO 7
<211> LENGTH: 611
<212> TYPE: DNA
<213> ORGANISM: Artificial Sequence
<220> FEATURE:
<223> OTHER INFORMATION: artificial construct

<400> SEQUENCE: 7
gtcatagcga cttttgggat agtttgctat cgacaaaggg agacaaagtc aaggggtgaa       60
gggaaaggag ggccaagtag agcctccacg accctcggct tcctcctcac cagctccccc      120
tccctccaag tccagtaaga agtttgggcca agctggaagg gattgaccgg ccgtttcctc     180
tccctcgccg gcctcggcgg agattccagg ccctatagaa accaggacgt cccttagcgc      240
caccgcctca catgccagtg ctgccgggaa cccagcgata tccgcaccag cggagaaggt      300
tccaggctgc cggcggcggc gcagagagcg ggaagagagg ctcggaggaa gccccgggcg      360
tggcgtggtc aggctccgag agcggccggg atgcggccac accggcctgg taaactcgca      420
cctcttagga tcttgctccc ggactcattc ccttccccac ccctattttt aaagttttat      480
ttgggtcgtc tgtatcaatt tagaacgaga taaattaaga caaagaaagt aaaataaatc      540
gaaataaaat ataggaatag ctcttggcga aaaaaaaaa aaaaaaaaaa aaaaaaaaa        600 aaaaaaaaaa a                                                           611

<210> SEQ ID NO 8
<211> LENGTH: 549
<212> TYPE: DNA
<213> ORGANISM: Artificial Sequence
<220> FEATURE:
<223> OTHER INFORMATION: artificial construct

<400> SEQUENCE: 8
gtcatagcga cttttgggat agtttgctat cgacaaaggg agacaaagtc aaggggtgaa       60
gggaaaggag ggccaagtag agcctccacg accctcggct tcctcctcac cagctccccc      120
tccctccaag tccagtaaga agtttgggcca agctggaagg gattgaccgg gttgcttgtc     180
tggagatgga gccactacag gcgggcctgg gcgcctggag tcgggcatga agaaaatag       240 cgcctcatcg ctcttatcta agcccagagg tagacttcgc ttgaaaagat cgagaatgga      300
ggaggggatc ggcactcact tgcagacatc aacagtttcc agaaaattcg gttcaattcc      360
ttcaccacgg acccaccaac caaggagctg gcaaaaccca ctaaccaacc aggagaacac      420
agacccggtt tgtcttttga caaccgagtg gaactgacgg ggccggcgcc tgccctgcgg      480 gtccctccc ttggctgaga agaaaaccaa ataaaccttg aacagccttg gcttcgaaaa       540
aaaaaaaaa                                                              549

<210> SEQ ID NO 9
<211> LENGTH: 452
<212> TYPE: DNA
<213> ORGANISM: Artificial Sequence
<220> FEATURE:
<223> OTHER INFORMATION: artificial construct

<400> SEQUENCE: 9
ggaaccagat cttgatctgg cgctcggaca ggcagagtgc gtgggcgatc tcgatgcgcc       60
gtcgccgggt caggttgctt gtctggagat ggagccacta caggcgggcc tgggcgcctg     120
```

```
gagtcgggca tgaaagaaaa tagcgcctca tcgctcttat ctaagcccag aggtagactt      180
cgcttgaaaa gatcgagaat ggaggagggg atcggcactc acttgcagac atcaacagtt      240
tccagaaaat tcggttcaat tccttcacca cggacccacc aaccaaggag ctggcaaaac      300
ccactaacca accaggagaa cacagacccg gtttgtcttt tgacaaccga gtggaactga      360
cggggccggc gcctgccctg cgggtcccct cccttggctg agaagaaaac caaataaacc      420
ttgaacagcc ttggcttcga aaaaaaaaaa aa                                    452

<210> SEQ ID NO 10
<211> LENGTH: 478
<212> TYPE: DNA
<213> ORGANISM: Artificial Sequence
<220> FEATURE:
<223> OTHER INFORMATION: artificial construct

<400> SEQUENCE: 10
cagtttccag aaaattcggt tcaattcctt caccacggac ccaccaacca aggagctggc      60
aaaacccact aaccaaccag gagaacacag acccgccgtt tcctctccct cgccggcctc     120
ggcggagatt ccaggcccta gaaaaccag gacgtccctt agcgccaccg cctcacatgc      180
cagtgctgcc gggaacccag cgatatccgc accagcggag aaggttccag gctgccggcg     240
gcggcgcaga gagcgggaag agaggctcgg aggaagcccc gggcgtggcg tggtcaggct     300
ccgagagcgg ccgggatgcg gccacaccgg cctggtaaac tcgcacctct taggatcttg     360
ctcccggact cattcccttc ccacccccct attttaaagt tttatttggg tcgtctgtat     420
caatttagaa cgagataaat taagacaaag aaagtaaaat aaatcgaaat aaaatata       478

<210> SEQ ID NO 11
<211> LENGTH: 22
<212> TYPE: DNA
<213> ORGANISM: Artificial Sequence
<220> FEATURE:
<223> OTHER INFORMATION: artificial construct

<400> SEQUENCE: 11
ccattctcga tcttttcaag cg                                               22

<210> SEQ ID NO 12
<211> LENGTH: 20
<212> TYPE: DNA
<213> ORGANISM: Artificial Sequence
<220> FEATURE:
<223> OTHER INFORMATION: artificial construct

<400> SEQUENCE: 12
aggttgcttg tctggagatg                                                  20

<210> SEQ ID NO 13
<211> LENGTH: 25
<212> TYPE: DNA
<213> ORGANISM: Artificial Sequence
<220> FEATURE:
<223> OTHER INFORMATION: artificial construct

<400> SEQUENCE: 13
cgcctcatcg ctcttatcta agccc                                            25

<210> SEQ ID NO 14
<211> LENGTH: 20
<212> TYPE: DNA
```

```
<213> ORGANISM: Artificial Sequence
<220> FEATURE:
<223> OTHER INFORMATION: artificial construct

<400> SEQUENCE: 14
gccggcgagg gagaggaaac                                                     20

<210> SEQ ID NO 15
<211> LENGTH: 22
<212> TYPE: DNA
<213> ORGANISM: Artificial Sequence
<220> FEATURE:
<223> OTHER INFORMATION: artificial construct

<400> SEQUENCE: 15
cttggttggt gggtccgtgg tg                                                  22

<210> SEQ ID NO 16
<211> LENGTH: 19
<212> TYPE: DNA
<213> ORGANISM: Artificial Sequence
<220> FEATURE:
<223> OTHER INFORMATION: artificial construct

<400> SEQUENCE: 16
cgtttcctct ccctcgccg                                                      19

<210> SEQ ID NO 17
<211> LENGTH: 19
<212> TYPE: DNA
<213> ORGANISM: Artificial Sequence
<220> FEATURE:
<223> OTHER INFORMATION: artificial construct

<400> SEQUENCE: 17
caccaaccaa ggagctggc                                                      19

<210> SEQ ID NO 18
<211> LENGTH: 22
<212> TYPE: DNA
<213> ORGANISM: Artificial Sequence
<220> FEATURE:
<223> OTHER INFORMATION: artificial construct

<400> SEQUENCE: 18
caagctggaa tggaggaggg ga                                                  22

<210> SEQ ID NO 19
<211> LENGTH: 21
<212> TYPE: DNA
<213> ORGANISM: Artificial Sequence
<220> FEATURE:
<223> OTHER INFORMATION: artificial construct

<400> SEQUENCE: 19
cgtcagttcc actcggttgt c                                                   21

<210> SEQ ID NO 20
<211> LENGTH: 22
<212> TYPE: DNA
<213> ORGANISM: Artificial Sequence
<220> FEATURE:
<223> OTHER INFORMATION: artificial construct

<400> SEQUENCE: 20
caagctggaa tggaggaggg ga                                                  22
```

<210> SEQ ID NO 21
<211> LENGTH: 19
<212> TYPE: DNA
<213> ORGANISM: Artificial Sequence
<220> FEATURE:
<223> OTHER INFORMATION: artificial construct

<400> SEQUENCE: 21
gagcgaggag gaagccgag                                                  19

<210> SEQ ID NO 22
<211> LENGTH: 27
<212> TYPE: DNA
<213> ORGANISM: Artificial Sequence
<220> FEATURE:
<223> OTHER INFORMATION: artificial construct

<400> SEQUENCE: 22
cggcttcctc ctcgctctta tctaagc                                         27

<210> SEQ ID NO 23
<211> LENGTH: 23
<212> TYPE: DNA
<213> ORGANISM: Artificial Sequence
<220> FEATURE:
<223> OTHER INFORMATION: artificial construct

<400> SEQUENCE: 23
tacgctacgt aacggcatga cag                                             23

<210> SEQ ID NO 24
<211> LENGTH: 22
<212> TYPE: DNA
<213> ORGANISM: Artificial Sequence
<220> FEATURE:
<223> OTHER INFORMATION: artificial construct

<400> SEQUENCE: 24
caagctggaa tggaggaggg ga                                              22

<210> SEQ ID NO 25
<211> LENGTH: 23
<212> TYPE: DNA
<213> ORGANISM: Artificial Sequence
<220> FEATURE:
<223> OTHER INFORMATION: artificial construct

<400> SEQUENCE: 25
ggttagtggc tccatctcca gac                                             23

<210> SEQ ID NO 26
<211> LENGTH: 25
<212> TYPE: DNA
<213> ORGANISM: Artificial Sequence
<220> FEATURE:
<223> OTHER INFORMATION: artificial construct

<400> SEQUENCE: 26
gatggagcca ctaaccaacc aggag                                           25

<210> SEQ ID NO 27
<211> LENGTH: 23
<212> TYPE: DNA
<213> ORGANISM: Artificial Sequence
<220> FEATURE:

```
<223> OTHER INFORMATION: artificial construct

<400> SEQUENCE: 27
tacgctacgt aacggcatga cag                                           23

<210> SEQ ID NO 28
<211> LENGTH: 22
<212> TYPE: DNA
<213> ORGANISM: Artificial Sequence
<220> FEATURE:
<223> OTHER INFORMATION: artificial construct

<400> SEQUENCE: 28
caagctggaa tggaggaggg ga                                            22

<210> SEQ ID NO 29
<211> LENGTH: 21
<212> TYPE: DNA
<213> ORGANISM: Artificial Sequence
<220> FEATURE:
<223> OTHER INFORMATION: artificial construct

<400> SEQUENCE: 29
ggttgtgcaa gtgagtgccg a                                             21

<210> SEQ ID NO 30
<211> LENGTH: 24
<212> TYPE: DNA
<213> ORGANISM: Artificial Sequence
<220> FEATURE:
<223> OTHER INFORMATION: artificial construct

<400> SEQUENCE: 30
cacttgcaca accgagtgga actg                                          24

<210> SEQ ID NO 31
<211> LENGTH: 23
<212> TYPE: DNA
<213> ORGANISM: Artificial Sequence
<220> FEATURE:
<223> OTHER INFORMATION: artificial construct

<400> SEQUENCE: 31
tacgctacgt aacggcatga cag                                           23

<210> SEQ ID NO 32
<211> LENGTH: 21
<212> TYPE: DNA
<213> ORGANISM: Artificial Sequence
<220> FEATURE:
<223> OTHER INFORMATION: artificial construct

<400> SEQUENCE: 32
ctcggcttcc tcctcaccag c                                             21

<210> SEQ ID NO 33
<211> LENGTH: 23
<212> TYPE: DNA
<213> ORGANISM: Artificial Sequence
<220> FEATURE:
<223> OTHER INFORMATION: artificial construct

<400> SEQUENCE: 33
tacgctacgt aacggcatga cag                                           23
```

ANTISENSE OLIGOMERS TARGETING HOXB-AS3 LONG NON-CODING RNA

CROSS-REFERENCE TO RELATED APPLICATIONS

This application is a national stage application filed under 35 U.S.C. § 371 of PCT/US2017/059932 filed Nov. 3, 2017, which claims the benefit of U.S. Provisional Patent Application Ser. No. 62/416,993 filed Nov. 3, 2016, which is expressly incorporated herein by reference.

FIELD

The present disclosure relates to antisense oligomers for use in methods of treating acute myeloid leukemia.

BACKGROUND

Acute myeloid leukemia (AML) is a highly heterogeneous disease with regard to its underlying genetic abnormalities and clinical course. Chromosomal abnormalities deletions, translocations) are identified in approximately 50% of all de novo AML patients. The remaining 50% of AML patients display no karyotypic aberrations in their leukemic clones when assessed with conventional karyotype analyses, that is they have cytogenetically normal AML (CN-AML). Previous work has identified several recurrent gene mutations which associate with the clinical outcome of CN-AML patients and are used in the clinic to risk-stratify the treatment of this patient population. Among them, mutations of the NPM1 gene represent one of the most common genetic alterations in CN-AML, as they are detected in approximately 60% of the newly diagnosed CN-AML cases. This gene encodes for a ubiquitously expressed nucleolar protein that shuttles between the nucleus and cytoplasm. NPM1 mutations specifically result in the inappropriate localization of the NPM1 protein from the nucleus into the cytoplasm. It has been reported that NPM1-mutated CN-AML exhibits distinctive and strong mRNA expression profiles characterized by HOX gene family overexpression and CD34 negativity. AML with mutant NPM1 is now recognized as a distinct entity of AML according to the WHO classification of myeloid neoplasms. Mechanistically, over-expression of mutant NPM1 in mice progenitors induces myeloid proliferation and HOX gene overexpression, supporting a critical role of the mutated protein in leukemogenesis.

In addition to genetic alterations in protein coding genes, aberrant expression of noncoding RNAs plays a critical role in leukemogenesis. A novel class of non-coding RNAs, named long noncoding RNAs (lncRNAs), which encompasses all non-protein coding RNA transcripts longer than 200 nucleotides has been recently described. A large body of accumulating data supports the important regulatory role that lncRNAs play during imprinting, cell differentiation, apoptosis, stem cell function via a plethora of mechanisms. The long intergenic RNA (lincRNA) HOTAIR, whose over-expression induces metastatic phenotype in murine models of breast cancer, the lincRNA SAMSON, which associates with aggressive phenotype of melanoma and the lincRNA LUNAR1 which regulates IGF1R mRNA expression and affects IGF1 signaling in acute lymphoblastic leukemia are notable examples among many others. In CN-AML, it has previously reported that a small number of lncRNAs strongly associate with clinical outcome and provide independent prognostic information in younger adults and older patients with CN-AML. In addition, it was found that recurrent prognostic gene mutations, including NPM1 mutations, associate with distinctive lncRNA signatures. Among the most highly upregulated lncRNAs in patients who harbored NPM1 mutations in both younger and older patient datasets, was a HOXB cluster-embedded lncRNA named HOXB-AS3.

The HOX gene locus contains several lncRNAs that have been shown to play significant roles in malignant diseases, mainly by regulating the expression levels of HOX genes. HOTAIR is a paradigm of this category, as it has been shown to associate with the Polycomb repressor complex and guide its localization on the genome, thereby silencing the HOXD locus. HOTTIP is a lncRNA that is implicated in chromosomal looping, whose overexpression results in Polycomb repressor complex-mediated silencing of the HOXD9. HOTAIRM1 is a HOXA-antisense lncRNA which is involved in the retinoic acid-mediated granulocytic maturation of healthy hematopoietic and leukemic cells by regulating the expression levels of HOXA1 and HOXA4.

The prognosis of AML is poor, highlighting the urgent need for novel therapeutic approaches. The compounds, compositions, and methods disclosed herein address these and other needs.

SUMMARY

Disclosed herein are novel locked nucleic acid (LNA) oligomers targeting the long non-coding RNA HOXB-AS3 for treating acute myeloid leukemia. The inventors have determined that there is a causal relationship between expression of HOXB-AS3 and the presence of NPM1 mutations in acute myeloid leukemia. In addition, in vivo knock down of HOXB-AS3 using LNA oligomers led to a significant increase in the overall survival of mice xenografted with AML blasts from several patients. In some embodiments, a liposome-based method for packaging and delivering in vivo HOXB-AS3 targeting LNA oligomers is used with no significant toxicities.

In some aspects, disclosed herein is a single stranded oligomer, wherein the oligomer is perfectly complementary to a corresponding region of HOXB-AS3 non-coding RNA, and wherein the oligomer comprises at least one nucleotide analogue having a modified sugar moiety.

In some embodiments, the oligomer is between 10-30 nucleotides. In some embodiments, the oligomer is between 15-25 nucleotides.

In some embodiments, the at least one nucleotide analogue having a modified sugar moiety comprises a Locked Nucleic Acid. In some embodiments, the oligomer further comprises a modified phosphodiester linkage. In some embodiments, the modified phosphodiester linkage comprises a phosphorothioate bond.

In some embodiments, the HOXB-AS3 non-coding RNA has the nucleic acid sequence encoded by SEQ ID NO:7, SEQ ID NO:8, SEQ ID NO:9, or SEQ ID NO:10.

In some embodiments, the oligomer comprises a nucleic acid sequence selected from SEQ ID NO:1, SEQ ID NO:2, SEQ ID NO:3, SEQ ID NO:4, SEQ ID NO:5, or a mixture thereof. In some embodiments, the oligomer comprises the nucleic acid sequence SEQ ID NO:2. In some embodiments, the oligomer comprises the nucleic acid sequence SEQ ID NO:3.

In some aspects, disclosed herein is a method for treating acute myeloid leukemia comprising administering to a subject in need thereof a single stranded oligomer, wherein the oligomer is perfectly complementary to a corresponding region of HOXB-AS3 non-coding RNA, and wherein the oligomer comprises at least one nucleotide analogue having a modified sugar.

In some embodiments, the oligomer inhibits the expression of HOXB-AS3 non-coding RNA in a cell.

In some embodiments, the acute myeloid leukemia is cytogenetically normal AML. (CN-AML).

In some aspects, disclosed herein is a method of inhibiting the expression of HOXB-AS3 in a cell, comprising contacting the cell with an effective amount of a single stranded oligomer, wherein the oligomer is perfectly complementary to a corresponding region of HOXB-AS3 non-coding RNA, and wherein the oligomer comprises at least one nucleotide analogue having a modified sugar moiety.

In some embodiments, the cell is within a tissue of a mammal.

In other aspects, disclosed herein is a composition comprising a cationic nanoparticle and a single stranded oligomer, wherein the oligomer is perfectly complementary to a corresponding region of HOXB-AS3 non-coding RNA, and wherein the oligomer comprises at least one nucleotide analogue having a modified sugar moiety.

In some aspects, disclosed herein is a pharmaceutical composition comprising a single stranded oligomer as described herein and a pharmaceutically acceptable diluent, carrier, salt or adjuvant.

BRIEF DESCRIPTION OF DRAWINGS

The accompanying figures, which are incorporated in and constitute a part of this specification, illustrate several aspects described below.

(FIG. 1A) Distribution of HOXB-AS3 expression in younger adults with cytogenetically normal AML (CN-AML) with wild-type NPM1 (NPM1 wt: n=168) or with NPM1 mutations (NPA1mut). (FIG. 1B) Genomic location of the four HOXB-AS3 transcripts, which were identified by 5-end and 3-end rapid amplification of cDNA ends-assays in OCI-AML3 cells. Rectangles indicate exons and lines indicate introns. The detected HOXB-AS3 transcripts are depicted in red and the neighboring, protein-coding HOXB5 and HOXB6 genes are depicted in blue color. The positive strand is depicted in red and the negative strand in blue (FIG. 1C) Expression levels of HOXB-AS3 as measured by real-time PCR (RT-PCR) in six different AML cell lines. Threshold cycle (Ct) values of HOXB-AS3 RNA expression were normalized against GAPDH Ct values. (FIG. 1D) Comparison of HOXB-AS3 expression in bone marrow samples from six healthy donors (hBM), AML blasts from six patients with NPM1mut and AML blasts from six patients with NPM1 wt, in aggregate. HOXB-AS3 RNA measurements were normalized against β-ACT Ct values, indicates P≤0.002. (FIG. 1E) NPM1 mRNA and (FIG. 1F) HOXB-AS3 RNA abundancy in OCI-AML3 cells treated with non-targeting control (Scramble) versus NPM1-targeting oligonucleotides (NPM1-KD). Threshold cycle (Ct) values of NPM1 and HOXB-AS3 expression were normalized against GAPDH Ct values. indicates P<0.01, *indicates P<0.05. (FIG. 1G) HOXB-AS3 RNA abundancy in CRISPR-engineered OCI-AML3 cells that lack the mutant NPM1 allele (NPM1$^{wt/-}$). OCI-AML3 cells treated with non-targeting guide RNAs (NPM1$^{wt/mnt}$) were used as controls. ****indicates P<0.001. (FIG. 1H) Hoxb5os RNA abundancy in lineage negative murine cells of Npm1$^{mut/wt}$ transgenic mice versus Npm1$^{wt/wt}$ controls. HOXB-AS3 RNA measurements were normalized against β-act Ct values.

(FIG. 2A) Abundancy of HOXB-AS3 RNA in OCI-AML3 cells treated with non-targeting control (Scramble) versus HOXB-AS3-targeting oligonucleotides (HBAS3-KD). Threshold cycle (Ct) values of HOXB-AS3 expression were normalized against GAPDH Ct values. The ratios of the normalized Ct values to that of the Scramble-treated sample are depicted in the graph. ***indicates P=0.001 (FIG. 2B) Cell cycle analysis based on Bromodeoxyuridine (BrdU) and 7-Aminoactinomycin D (7-AAD) incorporation and flow cytometry in Scramble—versus HBAS3-KD-treated OCI-AML3 cells. The flow cytometry graphs of one experiment are depicted as an example. (FIG. 2C) Comparison of the percent of cells at each stage of the cell cycle (G0/G1 Phase, S Phase, G2/M Phase) in OCI-AML3 cells treated with Scramble versus HBAS3-KD. *indicates P=0.02; NS indicates not significant. Results of three independent experiments are depicted (FIG. 2D) Comparison of the number of colonies formed by Scramble—versus HBAS3-KD-treated OCI-AML3 cells in colony-forming unit assays. *indicates P=0.02. Results of three independent experiments are depicted. (FIG. 2E) Abundancy of HOXB-AS3 RNA in K562 cells transfected with empty pcDNA3 vector (Control) versus a HOXB-AS3-overexpressing pcDNA3 vector. indicates P=0.02. (FIG. 2F) Cell-cycle analysis based on BrdU and 7-AAD incorporation followed by flow cytometry in Control—versus HBAS3-transfected K562 cells. Results of one experiment are depicted as an example. (FIG. 2G) Comparison of the percent of cells at each stage of the cell cycle (G0/G1 Phase, S Phase, G2/M Phase) in K562 cells transfected with Control versus HBAS3. indicates P=0.01;*indicates P=0.02; NS indicates not significant. Results of three independent experiments are depicted.

(FIG. 3A) Abundancy of HOXB-AS3 RNA in AML blasts from three patients with NPM1 mutations (NPM1mut), treated with non-targeting control (Scramble) versus HOXB-AS3-targeting oligonucleotides (HBAS3-KD). ****indicates P<0.001. (FIG. 3B) Number of colonies formed by Scramble versus HBAS3-KD-treated OCI-AML3 cells in colony-forming unit assays. *indicates P<0.05; *indicates P<0.005. (FIG. 3C) Schematic representation of the study design of in vivo HBAS3-KD, in a patient-derived xenograft (PDX) mouse model of NOD Scid gamma mice engrafted with human AML patient blasts (FIG. 3D) Abundancy of HOXB-AS3 RNA in AML blasts from an NPM1/mut AML patient treated in vivo, in a PDX mouse model, with nano-particle-formulated Scramble versus HBAS3-KD. Human AML blasts were isolated from the bone marrow of treated animals by magnetic bead-based sorting after staining for human CD45. *indicates P=0.003 (FIG. 3E), (FIG. 3F) Kaplan-Meyer curves depicting survival of NOD scid gamma (NSG) mice, which were xeno-transplanted with blasts of two different NPM1mut AML patients and treated with lipid nanoparticle-formulated Scramble or HBAS3-KD. In FIG. 3E, 10 mice were treated with Scramble and 11 with HBAS3-KD. In FIG. 3F, seven mice were treated with Scramble and eight with HBAS3-KD.

(FIG. 4A) HOX gene expression in scramble versus HOXB-AS3-KD treated OCI-AML3 cells, measured by RNA sequencing as aligned fragments per kilobase of transcript per million mapped reads. Abundancy of HOX messenger and long non-coding RNAs is depicted. Purification of the HOXB-AS3 and the U1 transcripts with biotinylated probes according to the RNA antisense purification (RAP) protocol in OCI-AML3 cell lysates. Yield of (FIG. 4B) HOXB-AS3 RNA, (FIG. 4C) U1 RNA and (FIG. 4D) GAPDH RNA in the eluate and the flow-through of lysates hybridized with either HOXB-AS3- or U1-targeting probes. Yield is depicted relative to (i.e., as percent of) the input sample. (FIG. 4E) List of candidate RNA binding proteins identified to interact with the HOXB-AS3 or the U1 transcript by Mass Spectometry analysis of the HOXB-AS3- or the U1-specific eluates. Proteins that have previously been reported to interact with U1 RNA are annotated in yellow color in the U1-specific list. Proteins that have previously been reported to form complexes are listed in proximity and annotated in blue color in the HOXB-AS3 specific list. The functions that these proteins regulate or the names of the complexes that they form are also annotated. (FIG. 4F) Validation of HOXB-AS3-protein interactions via RNA-Immunoprecipitation (RIP) experiments with nine exemplary chosen proteins. **indicates $P<0.001$, *indicates $P<0.005$, *** indicates $P<0.05$, NS indicates not significant. (FIG. 4G)-(FIG. 4I) Direct visualization of the HOXB-AS3 with custom-designed RNAScope assays (in red), combined with indirect immunofluorescent visualization of NPM1 and EBP1 proteins (in green). Visualization of Nucleolin (in green) served as non-HOXB-AS3 binding control. (FIG. 4J) Quantitation of the co-localizing NPM1, EBP1 or Nucleolin voxels which co-localize with HOXB-AS3. (FIG. 4K) Pearson co-relation coefficient values for the co-localization of NPM1, EBP1 or Nucleolin voxels with the HOXB-AS3. (FIG. 4L) Co-Immunoprecipitation experiments with anti-EBP1 or anti-NPM1 antibodies of nuclear lysates of OCI-AML3 cells, or the corresponding controls (Mouse or Rabbit IgG). Western-blot visualization for the EBP1 and NPM1 proteins was subsequently performed.

(FIG. 5A) Effect of HOXB-AS3 depletion on the formation of the EBP1-NPM1 complex in OCI-AML3 cells. In brief protein complexes were immunoprecipitated with anti-EBP1 or the corresponding control (Rabbit IgG). Western-blot visualization for the NPM1 and EBP1 protein was subsequently performed (FIG. 5B) Effect of HBAS3-KD on the abundancy of pre-ribosomal RNA (pre-rRNA) in OCI-AML3 cells. Threshold cycle (Ct) values of HOXB-AS3 RNA expression were normalized against GAPDH Ct values. *indicates $P<0.005$. (FIG. 5C), (FIG. 5D) Effect of HOXB-AS3 depletion on de novo protein synthesis in OCI-AML3 cells, as measured by Alexa Fluor 688-labelled O-Propargyl-Puromycin incorporation into newly synthesized peptides in Scramble versus HBAS3-KD treated cells. The mean fluorescent intensity of the FITCH-positive Scramble versus HBAS3-KD treated cells is compared and results of three independent experiments are depicted. (FIG. 5E) Sucrose gradient-based ribosome profiling of Scramble (in red) versus HBAS3-KD (in black) treated OCI-AML3 cells. (FIG. 5F) Occupancy of ribosomal DNA promoter repeat sequences (28S rDNA) by RNA-Polymerase I in OCI-AML3 cells treated with either non-targeting control (Scramble) versus HOXB-AS3-targeting oligonucleotides (HBAS3-KD). Rabbit IgG Immunoprecipitations were performed as control for unspecific antibody binding. *indicates $P<0.005$, indicates $P<0.001$ (FIG. 5G) Effect of HOXB-AS3 depletion on abundancy of pre-rRNA transcripts in AML patient blasts, after in vivo treatment of patient-derived xenografts. Human AML blasts were isolated from the bone marrow of treated animals by magnetic bead-based sorting after staining for human CD45 prior to RNA isolation. Three scramble and four HBAS3-KD-treated mice were analyzed, in aggregate. *indicates $P<0.005$ (FIG. 5H) Effect of HOXB-AS3 overexpression on the formation of the EBP1-NPM1 complex in K562 cells. In brief protein complexes were immunoprecipitated with anti-EBP1 antibodies, or the corresponding control (Rabbit IgG) in control versus HOXB-AS3-overexpressing K562 cells. Western-blot visualization for the EBP1 and NPM1 proteins was subsequently performed. (FIG. 5I) Effect of HOXB-AS3 overexpression (HBAS3) on abundancy of pre-rRNA in K562 cells. Threshold cycle (Ct) values of HOXB-AS3 RNA expression were normalized against GAPDH Ct values. *indicates $P<0.005$. (FIG. 5J), (FIG. 5K) Effect of HOXB-AS3 overexpression on de novo protein synthesis in K562 cells xenograft, as measured by GFP-labelled O-Propargyl-Puromycin incorporation into newly synthesized peptides in empty vector control versus HOXB-AS3 overexpressing K562 cells. The mean fluorescent intensity of the FITCH-positive control versus HOXB-AS3 overexpressing cells is compared and results of three independent experiments are depicted. (FIG. 5L) Luciferase/Renila activity in K562 cells transfected with an empty luciferase reporter vector or an rDNA-promoter containing luciferase reporter vector, a renila vector and empty pcDNA3 expression vector or a HOXB-AS3 overexpressing vector. indicates $P<0.01$. (FIG. 5M) Occupancy of ribosomal DNA promoter repeat sequences (28S rDNA) by RNA-Polymerase I in K562 cells transfected with either empty vector control or HOXB-AS3 overexpressing pcDNA3 vector.

(FIG. 6A) Wild-type HOXB-AS3 and five mutant variants generated by deletion of approximately 100 nucleotides (FIG. 6B) RNA immunoprecipitation experiments with native EBP1 of K562 cells which were transfected with either wt or mutant variants of HOKB-AS3.

(FIG. 7A) HOKB-AS3 expression between different cytogenetic AML subtypes and bone marrow-isolated healthy hematopoietic cells based on the publicly available dataset of the International Microarray Innovations in Leukemia Study Group. (FIG. 7B) HOXB-AS3 expression between different cytogenetic AML subtypes in the publicly available dataset of The Cancer Genome Atlas project. (FIG. 7C) HOXB-AS3 expression between different molecular subtypes of cytogenetically normal AML in the publicly available dataset of The Cancer Genome Atlas project.

(FIG. 8A) The areas of the HOXB-AS3 transcripts that are targeted by the different LNAs (LNA #1-#5) are annotated in blue-color boxes. (FIG. 8B), (FIG. 8C) Abundancy of the HOXB-AS3 RNA in OCI-AML3 cells treated with non-targeting control (Scramble) versus different LNAs (LNA #1-LNA #5), as measured by custom-designed real-time PCR assays. The assay used in FIG. 8B measures abundancy of transcripts NR_033202.2 and NR_033203.1. The assay used in FIG. 8C measures abundancy of transcripts NR_—033201.2 and uc060gwg.1. ** indicates P<0.0001; * indicates P<0.0009; **indicates P=0.002

(FIG. 9A) Apoptosis evaluation in OCI-AML3 cells treated with either non-targeting control (Scramble) or HOXB-AS3-targeting oligonucleotides (HBAS3-KD). Apoptosis analysis was conducted with Annexin V and Propidium Iodide (PI) staining and flow cytometry. Results of one experiment are depicted as an example. (FIG. 9B) Comparison of percent of viable and apoptotic cells in Scramble— versus HBAS3-KD-treated cells. Results of three independent experiments are depicted. NS indicates not significant.

DETAILED DESCRIPTION

Figure 1A:
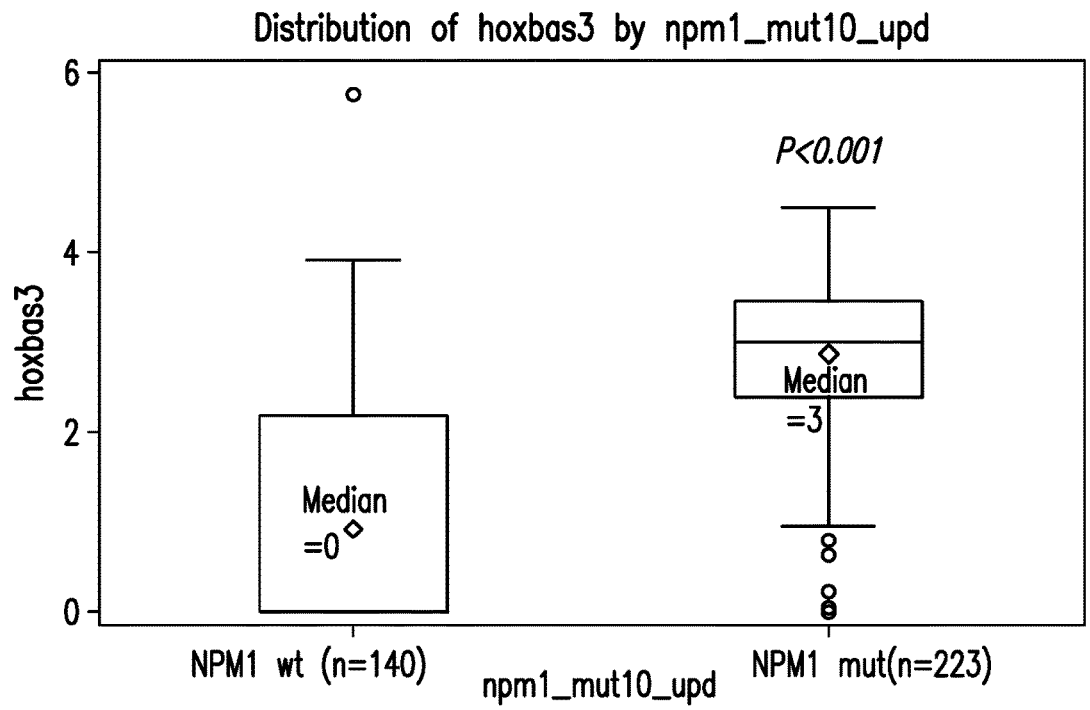
FIG. 1A-1H. Characterization and expression levels of the HOXB-AS3 long non-coding RNA in acute myeloid leukemia (AML) blasts and healthy hematopoietic cells.

Disclosed herein are novel locked nucleic acid (LNA) oligomers targeting the long non-coding RNA HOXB-AS3 for treating acute myeloid leukemia. The inventors have determined that there is a causal relationship between expression of HOXB-AS3 and the presence of NPM1 mutations in acute myeloid leukemia. In addition, in vivo knock down of HOXB-AS3 using LNA oligomers led to a significant increase in the overall survival of mice xenografted with AML blasts from several patients. In some embodiments, a liposome-based method for packaging and delivering in vivo HOXB-AS3 targeting LNA oligomers is used with no significant toxicities.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

The term "subject" or "host" refers to any individual who is the target of administration or treatment. The subject can be a vertebrate, for example, a mammal. Thus, the subject can be a human or veterinary patient. The term "patient" refers to a subject under the treatment of a clinician, e.g., physician. The subject can be either male or female.

The terms "peptide," "protein," and "polypeptide" are used interchangeably to refer to a natural or synthetic molecule comprising two or more amino acids linked by the carboxyl group of one amino acid to the alpha amino group of another.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA). In some embodiments, the DNA and RNA sequences are used interchangeably to refer to the RNA sequence encoded by the underlying DNA (gene) sequence. For example, antisense oligomers targeting the corresponding cDNA sequence of a non-coding RNA, are understood to hybridize to the analogous RNA sequence encoded by the DNA sequence provided. It is understood that for DNA sequences disclosed herein, the corresponding RNA sequences are also disclosed herein (wherein all thymine (T) nucleotides are replaced by a uracil (U) nucleotide, and all deoxyribose moieties in the DNA are replaced with the ribose moieties present in RNA).

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T/U, or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, at least about 75%, or at least about 90% complementary. See Kanehisa (1984) Nucl. Acids Res. 12:203.

"Hybridization" refers to the process in which two single-stranded oligonucleotides bind non-covalently to form a stable double-stranded oligonucleotide. The term "hybridization" may also refer to triple-stranded hybridization. The resulting (usually) double-stranded oligonucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. In certain exemplary embodiments, hybridization takes place at room temperature. The term "stringent hybridization conditions" as used herein is the binding which occurs within a range from about Tm 5° C. (5° C. below the melting temperature Tm of the probe) to about 20° C. to 25° C. below Tm. The term "highly stringent hybridization conditions" as used herein refers to conditions of: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

The term "oligomer" as used herein refers to a molecule formed by covalent linkage of two or more nucleotides (i.e. an oligonucleotide). Herein, a single nucleotide (unit) may also be referred to as a monomer or unit. In some embodiments, the oligomer consists or comprises of a contiguous nucleotide sequence of between 10-50, such as 10-30 nucleotides in length.

The term "LNA" refers to a bicyclic nucleotide analogue, known as "Locked Nucleic Acid". It may refer to an LNA monomer, or, when used in the context of an "LNA oligonucleotide", "LNA oligomer", or "LNA gapmer", LNA refers to an oligonucleotide containing one or more such bicyclic nucleotide analogues. LNA nucleotides are characterized by the presence of a biradical 'bridge' between C2' and C4' of the ribose sugar ring (LNA bases have a modification to the ribose backbone that locks the base in the C3'-endo-position). See for example, U.S. Pat. Nos. 8,563,528, 9,506,060.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

Antisense Oligomers and Methods

In some aspects, disclosed herein is a single stranded oligomer, wherein the oligomer is perfectly complementary to a corresponding region of HOXB-AS3 non-coding RNA, and wherein the oligomer comprises at least one nucleotide analogue having a modified sugar moiety.

In some embodiments, the oligomer is between 10-30 nucleotides. In some embodiments, the oligomer is between 15-25 nucleotides. In some embodiments, the oligomer is selected from the following number of nucleotides: 10, 11, 12, 13, 14, 15, 16, 17, 18, 19, 20, 21, 22, 23, 24, 25, 26, 27, 28, 29, or 30.

In some embodiments, the at least one nucleotide analogue having a modified sugar moiety comprises a Locked Nucleic Acid. In some embodiments, the oligomer further comprises a modified phosphodiester linkage. In some embodiments, the modified phosphodiester linkage comprises a phosphorothioate bond.

In some embodiments, at least one nucleotide analogue comprises a locked nucleic acid (for example, at least 1, at least 2, at least 3, at least 4, at least 5, at least 6, at least 7, at least 8, at least 9, at least 10) or more nucleotide analogues comprising a locked nucleic acid.

Figure 8A:
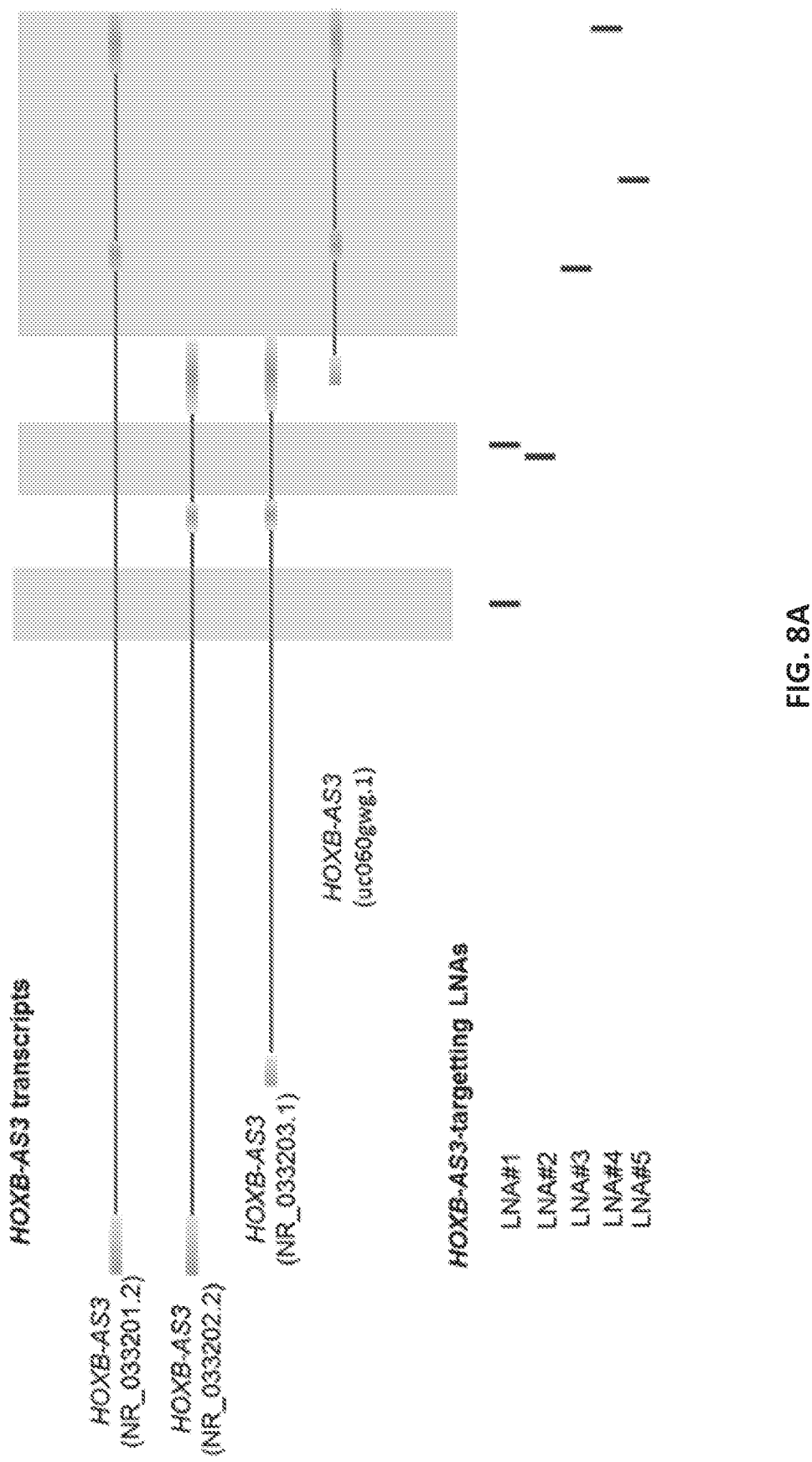
FIG. 8A-8C. Targeting of the HOXB-AS3 long non-coding RNA with RNase H-recruiting, locked nucleic acid-modified oligonucleotides (LNAs).
Figure 8B:
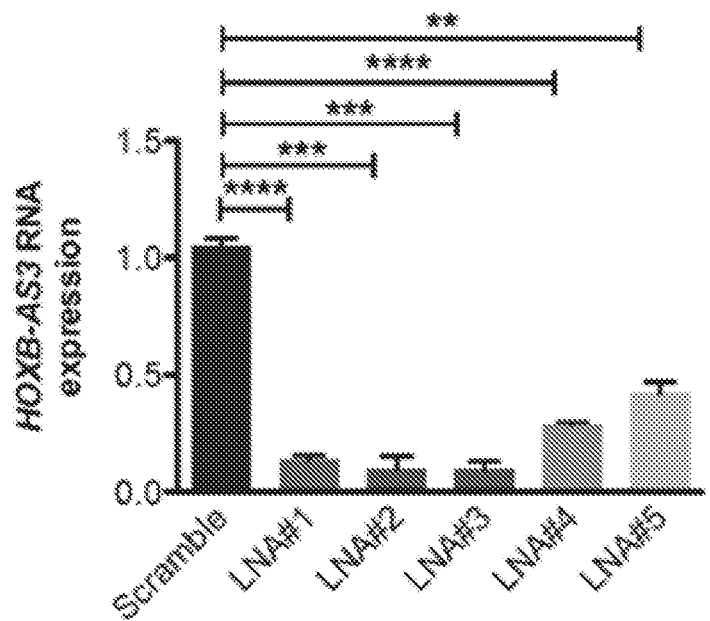
Figure 8C:
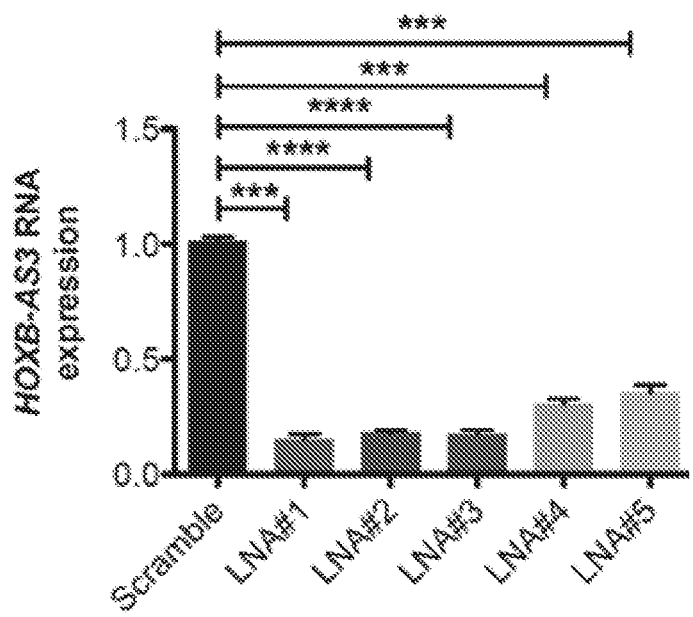

In some embodiments, the HOXB-AS3 non-coding RNA is encoded by the nucleic acid sequence encoded by SEQ ID NO:7, SEQ ID NO:8, SEQ ID NO:9, or SEQ ID NO:10. In some embodiments, the HOXB-AS3 non-coding RNA is encoded by the nucleic acid sequence SEQ ID NO:7. In some embodiments, the HOXB-AS3 non-coding RNA is encoded by the nucleic acid sequence SEQ ID NO:8. In some embodiments, the HOXB-AS3 non-coding RNA is encoded by the nucleic acid sequence SEQ ID NO:9. In some embodiments, the HOXB-AS3 non-coding RNA is encoded by the nucleic acid sequence SEQ ID NO:10. In some embodiments, the HOXB-AS3 non-coding RNA encoded by a nucleic acid sequence comprising at least 60% (for example, at least 60%, at least 65%, at least 70%, at least 75%, at least 80%, at least 85%, at least 90%, at least 95%, at least 99%) similarity to SEQ ID NO:7, SEQ ID NO:8, SEQ ID NO:9, or SEQ ID NO:10. The HOXB-AS3 transcripts are shown in FIG. 8 and the DNA sequences encoding the RNA transcripts are disclosed in the Sequences section below.

In some embodiments, the oligomer comprises a nucleic acid sequence selected from SEQ ID NO:1, SEQ ID NO:2, SEQ ID NO:3, SEQ ID NO:4, SEQ ID NO:5, or a mixture thereof. In some embodiments, the oligomer comprises the nucleic acid sequence SEQ ID NO:1. In some embodiments, the oligomer comprises the nucleic acid sequence SEQ ID NO:2. In some embodiments, the oligomer comprises the nucleic acid sequence SEQ ID NO:3. In some embodiments, the oligomer comprises the nucleic acid sequence SEQ ID NO:4. In some embodiments, the oligomer comprises the nucleic acid sequence SEQ ID NO:5. In some embodiments, the oligomer comprises a mixture of the nucleic acid sequence SEQ ID NO:2 and SEQ NO:3.

In some embodiments, the oligomer comprises a nucleic acid sequence with at least 60% (for example, at least 60%, at least 65%, at least 70%, at least 75%, at least 80%, at least 85%, at least 90%, at least 95%, at least 99%) similarity to SEQ ID NO:1, SEQ ID NO:2, SEQ ID NO:3, SEQ NO:4, SEQ ID NO:5.

In some embodiments, the oligomer targets a continuous sequence within the non-coding RNA. In some embodiments, the oligomer targets a split (non-continuous) sequence within the non-coding RNA (wherein the oligomer can hybridize to different portions of the non-coding RNA or may target different splice variants of the non-coding RNA).

In some aspects, disclosed herein is a single stranded oligomer, wherein the oligomer is substantially complementary to a corresponding region of HOXB-AS3 non-coding RNA, and wherein the oligomer comprises at least one nucleotide analogue having a modified sugar moiety.

In some embodiments, the at least one nucleotide analogue comprises a chemically modified nucleobase, a modified sugar moiety, a chemically modified phosphodiester linkage, or a combination thereof. In one embodiment, the chemically modified phosphodiester linkage is selected from Phosphorothioate (PS), Boranophosphate, phosphodithioate (PS2), 3',5'-amide, N3'-phosphoramidate (NP), Phosphodiester (PO), or 2',5'-phosphodiester (2',5'-PO). In one embodiment, the chemically modified phosphodiester linkage is phosphorothioate.

In some aspects, disclosed herein is a method for treating acute myeloid leukemia comprising administering to a subject in need thereof a single stranded oligomer, wherein the oligomer is perfectly complementary to a corresponding region of HOXB-AS3 non-coding RNA, and wherein the oligomer comprises at least one nucleotide analogue having a modified sugar.

In some embodiments, the oligomer is between 10-30 nucleotides. In some embodiments, the oligomer is between 15-25 nucleotides.

In some embodiments, the at least one nucleotide analogue having a modified sugar moiety comprises a Locked Nucleic Acid. In some embodiments, the oligomer further comprises a modified phosphodiester linkage. In some embodiments, the modified phosphodiester linkage comprises a phosphorothioate bond.

In some embodiments, the HOXB-AS3 non-coding RNA has the nucleic acid sequence encoded by SEQ ID NO:7, SEQ ID NO:8, SEQ ID NO:9, or SEQ ID NO:10.

In some embodiments, the oligomer comprises a nucleic acid sequence selected from SEQ ID NO:1 SEQ ID NO:2, SEQ ID NO:3, SEQ ID NO:4, SEQ ID NO:5, or a mixture thereof. In some embodiments, the oligomer comprises the nucleic acid sequence SEQ ID NO:2. In some embodiments, the oligomer comprises the nucleic acid sequence SEQ ID NO:3.

In some embodiments, the oligomer inhibits the expression of HOXB-AS3 non-coding RNA in a cell.

In some embodiments, the acute myeloid leukemia is cytogenetically normal AML (CN-AML).

In some aspects, disclosed herein is a method of inhibiting the expression of HOXB-AS3 in a cell, comprising contacting the cell with an effective amount of a single stranded oligomer, wherein the oligomer is perfectly complementary to a corresponding region of HOXB-AS3 non-coding RNA, and wherein the oligomer comprises at least one nucleotide analogue having a modified sugar moiety.

In some embodiments, the oligomer is between 10-30 nucleotides. In some embodiments, the oligomer is between 15-25 nucleotides.

In some embodiments, the at least one nucleotide analogue having a modified sugar moiety comprises a Locked Nucleic Acid. In some embodiments, the oligomer further comprises a modified phosphodiester linkage. In some embodiments, the modified phosphodiester linkage comprises a phosphorothioate bond.

In some embodiments, the HOXB-AS3 non-coding RNA has the nucleic acid sequence encoded by SEQ ID NO:7, SEQ ID NO:8, SEQ ID NO:9, or SEQ ID NO:10.

In some embodiments, the oligomer comprises a nucleic acid sequence selected from SEQ ID NO1, SEQ ID NO:2, SEQ ID NO:3, SEQ ID NO:4, SEQ ID NO:5, or a mixture thereof. In some embodiments, the oligomer comprises the nucleic acid sequence SEQ ID NO:2. In some embodiments, the oligomer comprises the nucleic acid sequence SEQ ID NO:3.

In some embodiments, the cell is within a tissue of a mammal.

In some embodiments, the acute myelogenous leukemia (AML) is cytogenetically normal acute myelogenous leukemia (CN-AML). In some embodiments, the acute myelogenous leukemia (AML) is NPM1mut (comprises an NPM1 mutation).

Compositions

In some aspects, disclosed herein is a composition comprising a cationic nanoparticle and a single stranded oligomer, wherein the oligomer is perfectly complementary to a corresponding region of HOXB-AS3 non-coding RNA, and wherein the oligomer comprises at least one nucleotide analogue having a modified sugar moiety.

In some embodiments, the oligomer is between 10-30 nucleotides. In some embodiments, the oligomer is between 15-25 nucleotides.

In some embodiments, the at least one nucleotide analogue having a modified sugar moiety comprises a Locked Nucleic Acid. In some embodiments, the oligomer further comprises a modified phosphodiester linkage. In some embodiments, the modified phosphodiester linkage comprises a phosphorothioate bond.

In some embodiments, the HOXB_AS3 non-coding RNA has the nucleic acid sequence encoded by SEQ ID NO:7, SEQ ID NO:8, SEQ ID NO:9, or SEQ ID NO:10.

In some embodiments, the oligomer comprises a nucleic acid sequence selected from SEQ ID NO:1, SEQ ID NO:2, SEQ ID NO:3, SEQ ID NO:4, SEQ ID NO:5, or a mixture thereof. In some embodiments, the oligomer comprises the nucleic acid sequence SEQ ID NO:2. In some embodiments, the oligomer comprises the nucleic acid sequence SEQ ID NO:3.

In some aspects, disclosed herein is a pharmaceutical composition comprising the oligomer as described herein and a pharmaceutically acceptable diluent, carrier, salt or adjuvant.

Compositions, as described herein, comprising an active compound and an excipient of some sort may be useful in a variety of applications. For example, pharmaceutical compositions comprising an active compound and an excipient can be useful for the treatment or prevention of acute myeloid leukemia. In one embodiment, disclosed herein is a pharmaceutical composition comprising: an oligomer as disclosed herein and a pharmaceutically acceptable excipient.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g, carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxytnethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), polyvinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkoniutn chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium hi sulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Plutonic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Di stearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty add esters (e.g, polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g, Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium, Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. The Long Non-Coding RNA HOXB-AS3 Regulates Ribosome Biogenesis in NPM1-Mutated Acute Myeloid Leukemia Acute myeloid leukemia (AML) is a highly heterogeneous disease with regard to its underlying genetic abnormalities and clinical course. The prognosis of AML is poor, highlighting the urgent need for novel therapeutic approaches. Chromosomal abnormalities (e.g., deletions, translocations) are identified in approximately 50% of all de novo AML patients. The remaining 50% of AML patients display no karyotypic aberrations in their leukemic clones when assessed with conventional karyotype analyses, that is they have cytogenetically normal AML (CN-AML). Previous work has identified several recurrent gene mutations which associate with the clinical outcome of CN-AML patients and are used in the clinic to risk-stratify the treatment of this patient population. Among them, mutations of the NPM1 gene represent one of the most common genetic alterations in CN-AML, as they are detected in approximately 60% of the newly diagnosed CN-AML cases. This gene encodes for a ubiquitously expressed nucleolar protein that shuttles between the nucleus and cytoplasm. NPM1 mutations specifically result in the inappropriate localization of the NPM1 protein from the nucleus into the cytoplasm. It has been reported that NPM1-mutated CN-AML exhibits distinctive and strong mRNA expression profiles characterized by HOX gene family overexpression and CD34 negativity. AML with mutant NPM1 is now recognized as a distinct entity of AML according to the WHO classification of myeloid neoplasms. Mechanistically, over-expression of mutant NPM1 in mice progenitors induces myeloid proliferation and HOX gene overexpression supporting a critical role of the mutated protein in leukemogenesis.

In addition to genetic alterations in protein coding genes, aberrant expression of noncoding RNAs plays a critical role in leukemogenesis. A novel class of non-coding RNAs, named long noncoding RNAs (lncRNAs), which encompass all non-protein coding RNA transcripts longer than 200 nucleotides has been recently described. A large body of accumulating data supports the important regulatory role that lncRNAs play during imprinting, cell differentiation, apoptosis, stem cell function via a plethora of mechanisms. The long intergenic RNA (lincRNA) HOTAIR, whose overexpression induces metastatic phenotype in murine models of breast cancer, the lincRNA SAMSON, which associates with aggressive phenotype of melanoma and the lincRNA LUNAR1 which regulates IGF1R mRNA expression and affects IGF1 signaling in acute lymphoblastic leukemia are notable examples among many others. In CN-AML, it has previously reported that a small number of lncRNAs strongly associate with clinical outcome and provide independent prognostic information in younger adults and older patients with CN-AML. In addition, it was found that recurrent prognostic gene mutations, including NPM1 mutations, associate with distinctive lncRNA signatures. Among the most highly upregulated lncRNAs in patients who harbored NPM1 mutations in both younger and older patient datasets, was a HOXB cluster-embedded lncRNA named HOXB-AS3.

The HOX gene locus contains several lncRNAs that have been shown to play significant roles in malignant diseases, mainly by regulating the expression levels of HOX genes. HOTAIR is a paradigm of this category, as it has been shown to associate with the Polycomb repressor complex and guide its localization on the genome, thereby silencing the HOXD locus. HOTTIP is a lncRNA that is implicated in chromosomal looping, whose overexpression results in Polycomb repressor complex-mediated silencing of the HOXD9. HOTAIRM1 is a HOXA-antisense lncRNA which is involved in the retinoic acid-mediated granulocytic maturation of healthy hematopoietic and leukemic cells by regulating the expression levels of HOXA1 and HOXA4. In the example here, the functional significance of HOXB-AS3 was examined in NPM1mut AML.

Methods

AML Patient Samples and Cell Lines

For association analyses of HOXB-AS3 expression with clinical characteristics, gene mutations and clinical outcome, a previously published cohort of 377 younger adults with CN-AML, who were treated on frontline Alliance CALGB protocols was analyzed. All patients had provided informed consent for the use of their biologic specimens for research purposes according to the Declaration of Helsinki. Cytogenetic analyses were performed with standard banding technique after stimulation of cells with for 48 h. Gene mutations, which have previously been described to be prognostic in AML were analyzed by means of a targeted DNA sequencing panel (Miseq; ASXL1, DNMT3A, IDH1, IDH2, FLT3-TKD, NPM1, RUNX1, TET2, WT1), Sanger sequencing (double CEBPA) and fragment analyses (FLT3-ITD), as previously described. Expression levels of prognostic mRNA (BAALC, MN1, ERG) and microRNA (miR-155, miR-181) genes were evaluated with total RNAseq and small RNAseq, respectively.

For the in vitro and in vivo functional experiments leukapheresis samples of AML patients deposited in the biobank of The Ohio State University were used. For in vitro experiments patient blasts were cultured in SFEM media (Stem cell technologies), supplemented with 10% BIT media and cytokines (hSCF, hTPO, hFLT3-ligand, hIL-3 and hIL-6-Peprotech). For colony formation unit assays, cells were electroporated (see below cultured for 24 h and then mixed with Methocult, Stem Cell technologies, according to the instructions of the manufacturer. For in vivo experiments NOD-Scid Gamma (NSG) mice, pretreated with Busulfan (20 mg/kg weight) were engrafted with 10 million AML blasts, as previously described.

Kasumi-1, KG1-A, MV4-11, MOLM-13, K562, OCI-AML3 and the THP1 AML cell lines were grown in RPM1 media, supplemented with 10% FBS. For colony formation unit assays, cells were electroporated (see below), cultured for 24 h and then mixed with plain Methocult (without cytokines), Stem Cell technologies, according to the instructions of the manufacturer RNA Isolation and cDNA Transcription RNA isolations were performed using the Trizol reagent according to the instructions of the manufacturer. Reverse transcription was performed with the Superscript III single strand RT kit. All custom real time PCR experiments were conducted in the standard conditions, suggested by Applied Biosystems. The sequences of the real-time assays used to interrogate HOXB-AS3 expression were the following:

```
Primer #1:
                                        (SEQ ID NO: 11)
CCA TTC TCG ATC TTT TCA AGC G Primer #2:
                                        (SEQ ID NO: 12)
AGG TTG CTT GTC TGG AGA TG Probe:
                                        (SEQ ID NO: 13)
/56-FAM/CGC CTC ATC/ZEN/GCT CTT ATC TAA GCC C/
3IABkFQ/
```

Rapid amplification of cDNA ends was performed with the Generacer Assay Kit, Invitrogen, following the instructions of the manufacturer. The primer sequences used for the RACE assays are the following:

```
For the 5-end-RACE:
Rv.Primer#1:
                                        (SEQ ID NO: 14)
5'-GCC GGC GAG GGA GAG GAA AC-3'

Rv.Primer#2:
                                        (SEQ ID NO: 15)
5'-CTT GGT TGG TGG GTC CGT GGT G-3'

For the 3-end-RACE:
Fw primer#1:
                                        (SEQ ID NO: 16)
5'-CGT TTC CTC TCC CTC GCC G-3'

Fw primer#2:
                                        (SEQ ID NO: 17)
5'-CAC CAA CCA AGG AGC TGG C-3'
```

Gene Knock-Downs and Overexpression

For the knock-down of HOXB-AS3 in OCI-AML3 cells and samples from NPM1mut AML patients, custom-designed locked nucleic acid modified RNaseH recruiting oligonucleotides were used. For the in vitro delivery of the oligos, the Amaxa Nucleofector device and corresponding reagents (Solution T for OCI-AML3 cells and human Monocyte Solution for AML blasts) were used according to the instructions of the manufacturer.

For the in vivo knock down of the lncRNA, HOXB-AS3-targeting, LNA-modified Gapmers or non-targeting controls were packaged in a cationic liposomal nanoparticle formulation and were conjugated with human transferrin. Human AML xenografts were treated and followed for survival as previously described.

For the overexpression of HOXB-AS3, RACE identified transcripts were cloned into TOPO-Blunt end vectors (Invitrogen) and were then excised with double digestion with the enzymes Hind III and BamHI. Standard pcDNA3 LIC 6A vectors were acquired from Addgene and were also digested with the same restriction enzymes in parallel. Digestion products were weight separated by agarose gel electrophoresis and visible bands were excised, purified with the Qiagen gel extraction kit and ligated into the pcDNA3 vectors with T4 DNA ligase. Sequences were verified by Sanger sequencing.

Flow Cytometry Analyses

Cell cycle and apoptosis analyses were performed with the BrDU and the Annexin/PI staining kits of BD Biosciences. Experiments were analyzed with flow cytometry on an LSRII instrument, according to the instructions of the manufacturers.

RNA Antisense Purification Experiments

RNA-protein complex pull down experiments were conducted according to a modified version of the RAP protocol, as published by McHugh et al. (McHugh C A, Chen C K, Chow Al et al. The Xist lncRNA interacts directly with SHARP to silence transcription through HDAC3. *Nature,* 2015; 521(7551):232-236). In brief, batches of $20 \times 10^6$ cells were crosslinked directly with 8000 Joules/m2 of UV irradiation, Cells were lysed in lysis buffer (10 mM Tris-HCl, 500 mM LiCl, 0.5% dodecyl maltoside (DDM), 0.2% sodium dodecyl sulfate (SDS), 0.1% sodium deoxycholate), sonicated and treated with DNAse I (Norgen Biotek). Lysates were mixed with hybridization buffer (10 mM Tris-HCl, 5 mM EDTA, 500 mM LiCl, 0.5% DDM, 0.2% SDS, 0.1% sodium deoxycholate, 4 M urea, 2.5 mM TCEP) and span down in a table top centrifuge (10 minutes at 16000 Gs at 4° C.). The supernatants were pre-cleaned, by incubation (37 degrees for 30 minutes, shaking) with streptavidin-coated magnetic beads (Life Technologies, Dynabeads MyOne, Streptavidin C1). After removal of beads the lysates were incubated with biotinylated probes (2 μgs per 20 million cells) that were complementary to either the HOXB-AS3 or the U1 transcripts. The sequences of the biotinylated probes are provided in the supplemental material. Probes and lysates were allowed to hybridize by incubation at 67° C. for 2 hours, shaking. Streptavidin-coated magnetic beads were used for the purification of complexes. The purified complexes were either treated with Proteinase K (New England Biolabs) (to digest protein residues) or with benzonase nuclease (EMD Millipore) (to digest probes and captured RNA and release RNA-bound protein residues from the streptavidin beads). Proteinase K-treated eluates were mixed with an N-lauroylsarcosine-rich (NLS, Sigma) buffer, heated for 2 minutes at 95° C. and released from the magnetic beads. Eluted nucleic acids were subsequently treated with DNase I and purified by use of magnetic SILANE beads (Invitrogen, Dynabeads MyOne). The isolated RNA was reversed transcribed into cDNA and analyzed with RT-PCR. Polypeptides in the benzonase endonuclease treated samples were precipitated by overnight with trichloroacetic acid (Ricca Chemical Company) and centrifugation, Polypeptides were then digested with Trypsin (Promega) and Endopeptidase Lys-C (Wako), purified with HiPPR detergent removal columns (Lite Technologies) and analyzed with tandem mass spectrometry. The results were filtered for number and quality of identified peptides (for more information see data supplement) and analyzed comparatively to identify putative HOXB-AS3 and U1-specific protein interactors.

RNA Immunoprecipitations and Protein-Protein Co-Immunoprecipitation Experiments

RNA immunoprecipitation experiments to validate the predicted HOXB-AS3-protein interactions by the RAP screening experiments and co-immunoprecipitation experiments to study protein-protein interactions were conducted in nuclear lysates as previously described. In brief $10 \times 10^6$ cells were crosslinked by exposure to UV irradiation (8000 Joules/m2) prior to cell lysis. Cells were then re-suspended in 10 ml of lysis Buffer consisting of 6 ml of water, 2 ml of PBS and 2 ml of Nuclear Isolation Buffer (1.28 M sucrose, 40 mM Tris-HCl pH 7.5, 20 mM to MgCl2, 4% Triton X-100). Nuclei were pelleted by centrifugation at 2500 Gs at 4° C. for 15 minutes and were then re-suspended in 1 ml of RIP Buffer (150 mM KCl, 25 mM Tris pH 7.4, 5 mM EDTA, 0.5 mM DTT, 0.5% NP40 plus RNAase and Protease inhibitors). Cell pellets were sonicated with a microtip sonicator (pulse sonication of 5 Watts for 10 seconds followed by a 50-second interval, three repeats) and spun down for 10 minutes at 16.000 Gs at 4° C. Supernatants were mixed with magnetic A/G beads, pre-coated and cross-linked with antibodies as previously described and incubated overnight at 4° C. Beads were then magnetically separated, washed and mixed with either Proteinase K-containing solution (for RIP analyses) or beta-mercaptoethanol containing buffer (for Co-immunoprecipitation analyses).

Immunoprecipitates used for RIP analysis were treated with proteinase K (one hour at 52° C.) and were then mixed with 1 ml of Trizol reagent. Standard Trizol-based RNA isolations were subsequently performed. For Co-IPs, the beads were denatured at 99° C. for 10 mins. Following magnetic separation, the eluates were directly loaded onto SDS-PAGE gels and separated by electrophoresis.

Chromatin Immunoprecipitation Experiments

Chromatin immunoprecipitation experiments were conducted according to previously published protocols. To isolate nucleolar chromatin cells, the experimental approach described by O'Sullivan et al. was used (O'Sullivan A C, Sullivan G J, McStay B. UBF binding in vivo is not restricted to regulatory sequences within the vertebrate ribosomal DNA repeat. *Mol Cell Biol.* 2002; 22(2):657-668). Briefly, cells cross-linked by formaldehyde (0.25% for 10 min) and washed in phosphate buffered saline (PBS), After centrifugation at 200 Gs for 5 minutes, cell pellets were re-suspended in 1.0 ml of high-magnesium buffer (10 mM HEPES [pH 7.5], 0.88 M sucrose, 12 mM MgCl2, and 1 mM dithiothreitol [DTT], plus protease inhibitors). Nucleoli were released by sonication on ice (two to three bursts of 10 s each at full power) using a Soniprep 150 (MSE) with a fine probe. Nucleoli were pelleted by centrifugation in a microfuge (15,000 Gs for 20 s), and the pellets were resuspended in 1.0 ml of low-magnesium buffer (10 mM HEPES [pH 7.5], 0.88 M sucrose, 1 mM MgCl2, and 1 mM DTT, plus protease inhibitors). Nucleoli were subject to further sonication on ice (10 s at full power) and pelleted as before. Nucleoli were resuspended in 0.2 ml of 20/2TE (20 mM Tris [pH 8.0], 2 mM EDTA) and a 1/10 volume of 20% sodium dodecyl sulfate (SDS) was added. Following incubation at 37° C. for 15 min, 20/2TE (0.8 ml) was added, and the solutions were sonicated (three to four bursts of 5 s each at full power). The resulting sheared nucleolar chromatin was centrifuged in a microfuge (15,000 Gs for 10 min), and the nucleolar chromatin supernatant was used immediately in ChIP assays.

RNA Pol I or EBP1 (Cell signaling) antibodies were incubated with magnetic Agarose beads for one hour at room temperature and washed twice with PBS. Agarose beads were blocked by incubation in 2% BSA and salmon sperm containing solution. Cell lysates were pre-cleaned with blocked agarose beads, Antibodycoated beads were incubated overnight with nucleolar lysates. Chromatin immunoprecipitates were analyzed with the Simple Chip 28S rDNA assay (Cell signaling) and/or the custom primers for Nucleolar Chip as described by O; Sullivan et al.

rRNA Transcription Reporter and Assay

To further study the effect of HOXB-AS3 on the expression of rRNA transcription by RNA polymerase I, the pHrD-IRES-Luc (human rRNA promoter-luciferase reporter) was used. In this plasmid, Kozak sequence of the pGL3-basic vector has replaced by the internal ribosome entry site (IRES) of encephalomyocarditis viral genome to optimize pol I-driven reporter gene expression. K562 cells were concomitantly transfected with i) the Renilla, ii) the pGL3-IRES-Luc or the pHrD-IRES-Luc and iii) the pcDNA3 or the pcDNA3-HOXB-AS3 vectors. Transfected cells were incubated for 72 hours and were then lysed in lysis buffer (Promega), according to the instructions of the manufacturer. Luciferase activity was measured using the Dual Luciferase Assay kit (Promega) in a Luminometer (Lumat LB 9507; EG&G Berthold, Oak Ridge, Tenn.).

Results

Associations of HOXB-AS3 Expression Status with Pre-Treatment Characteristics and Clinical Outcome of CN-AML Patients The association of HOXB-AS3 expression with clinical features was evaluated in a dataset of 377 younger (aged <60 years) adults with CN-AML patients, whose samples were analyzed with RNA sequencing. Patients with NPM1 mutations (NPM1mut) had approximately a three-fold increase in HOXB-AS3 expression when compared to patients with wild-type NPM1 (NPM1 wt; FIG. 1A, P<0.001). Next, the median HOXB-AS3 expression value was used to divide the patient cohort into high or low HOXB-AS3 expressers. With regard to pretreatment characteristics, younger adult CN-AML patients with high HOXB-AS3 expression were more likely to be female than those with low HOXT3-AS3 expression (P=0.007). Patients with high HOXB-AS3 expression were also more likely to have higher white blood cell counts (P<0.001), and higher percent of blasts in peripheral blood (P<0.001) and in bone marrow (BM) (P<0.001) at the time of diagnosis. Other than NPM1 mutations, patients with high HOXB-AS3 were more likely to harbor internal tandem duplications of the FLT3 gene (FLT3-ITD, P<0.001), as well as mutations in the DNMT3A (P=0.004) and WT1 (P=0.02) genes and to be high expressers of miR-155 (P<0.001). In contrast, patients with low HOXB-AS3 expression were more likely to have mutations in the CEBPA (P<0.001), ASXL1 (P=0.006) and RUNX1 (P<0.001) genes and to be high expressers of MN1 (P<0.001), BAALC (P<0.001), miR-3151 (P<0.001) and miR-181a (P=0.05) genes. With regard to clinical outcome, patients with low HOXB-AS3 expression showed a trend towards higher complete remission rates when compared to patients with high HOXB-AS3 expression (87% versus 80%, P=0.07). There was no significant difference in other survival end points.

Figure 1B:
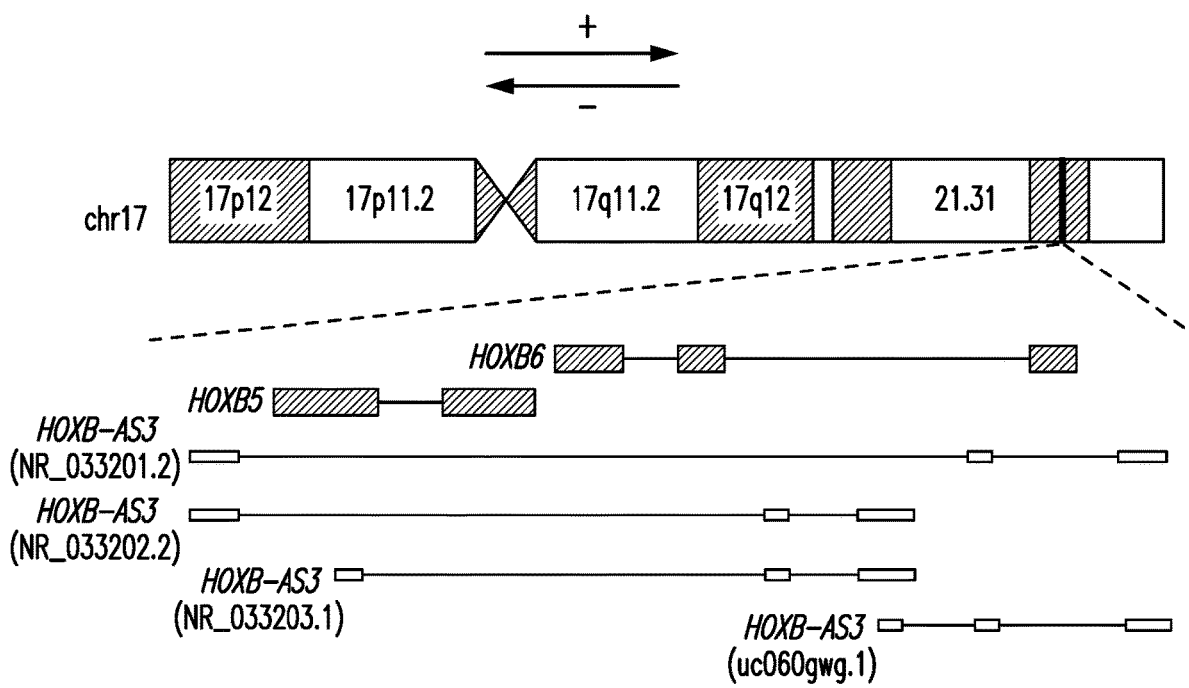

Characterization of HOXB-AS3 Transcripts and Expression Profiling in Healthy Hematopoietic Cells and Leukemic Blasts The HOXB-AS3 locus shows striking transcriptional complexity as 24 transcript variants of this lncRNA have been identified and annotated in genomic databases (UCSC Genome Browser). To characterize the transcripts that are expressed in leukemic blasts, 5-end and 3-end rapid amplification of cDNA ends (RACE) assays were performed in the NPM1mut harboring OCI-AML3 cells. Primers were designed based on the transcripts previously identified in a cohort of 148 older CN-AML patients, analyzed with the Arraystar microarray assay. Four different transcript variants of HOXB-AS3 were identified ((NR_033201.2, NR_033202.2, NR_033203.1, and uc60gwg. 1; FIG. 1B).

Figure 1C:
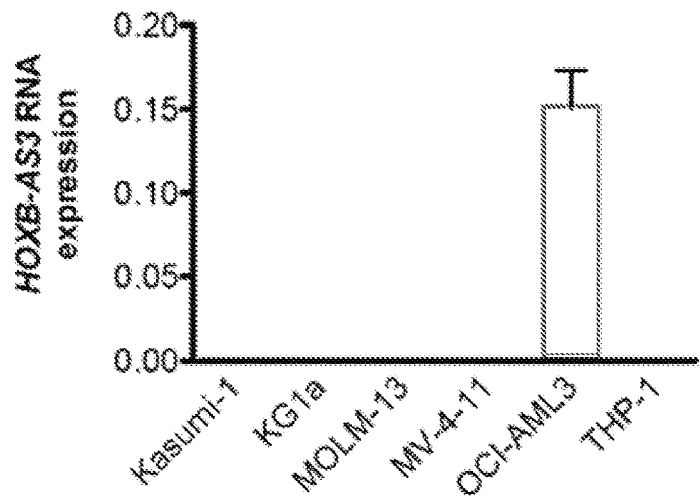
Figure 1D:
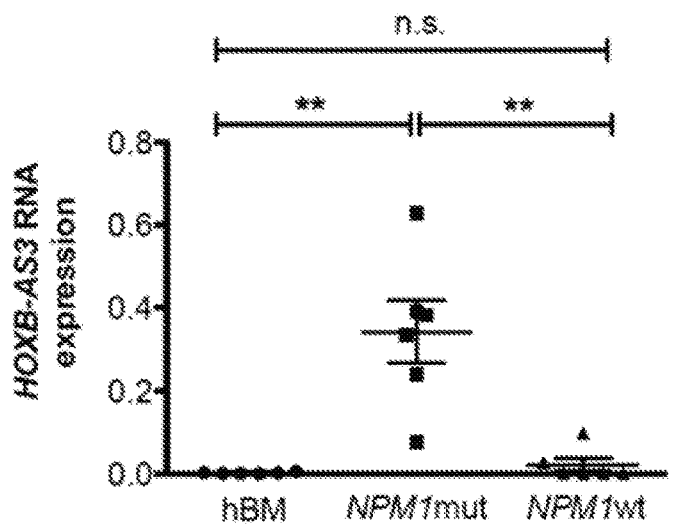
Figure 7A:
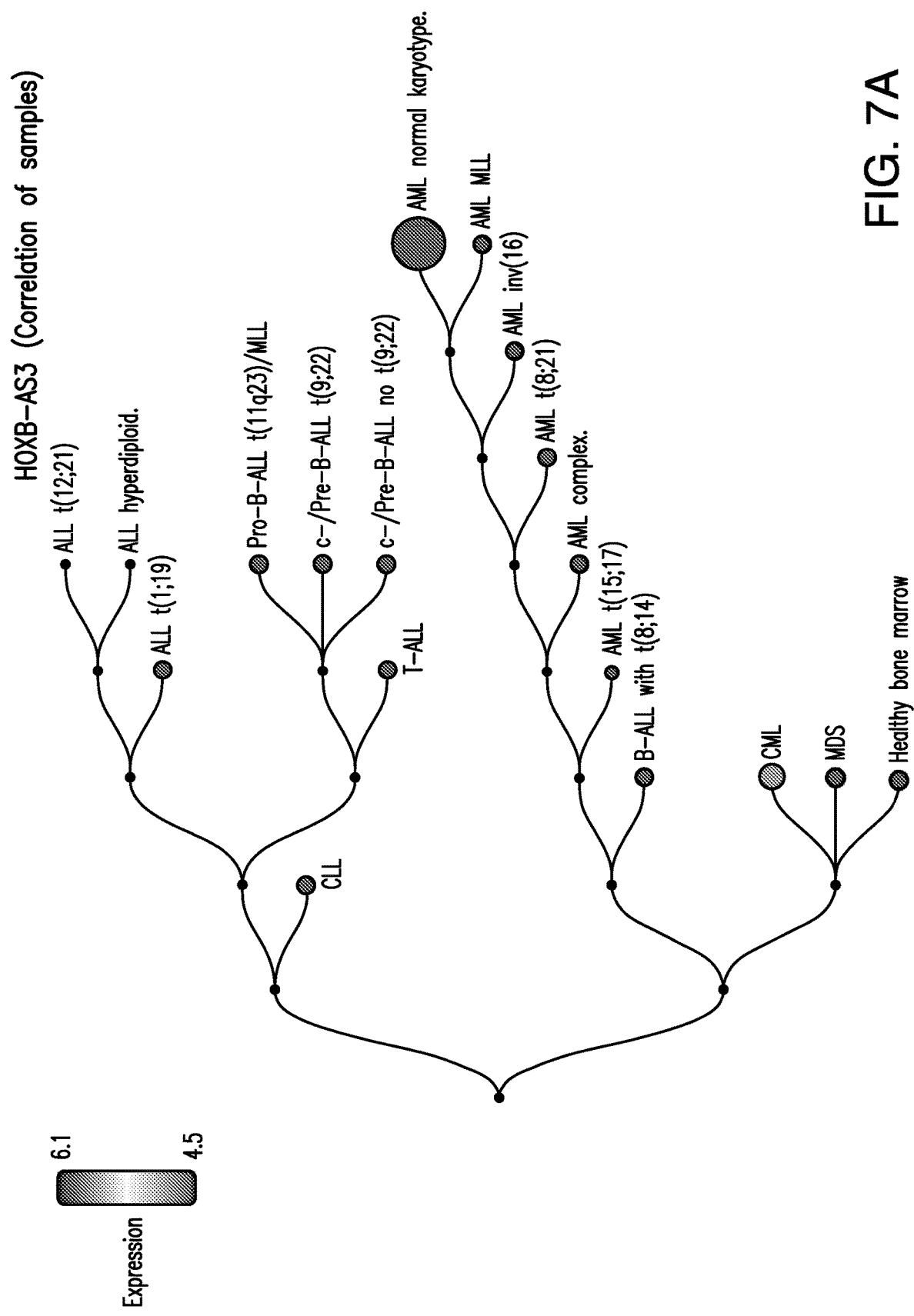
FIG. 7A-7C. Expression of the HOXB-AS3 long non-coding RNA across different populations of healthy hematopoietic cells and acute myeloid leukemia subtypes.
Figure 7B:
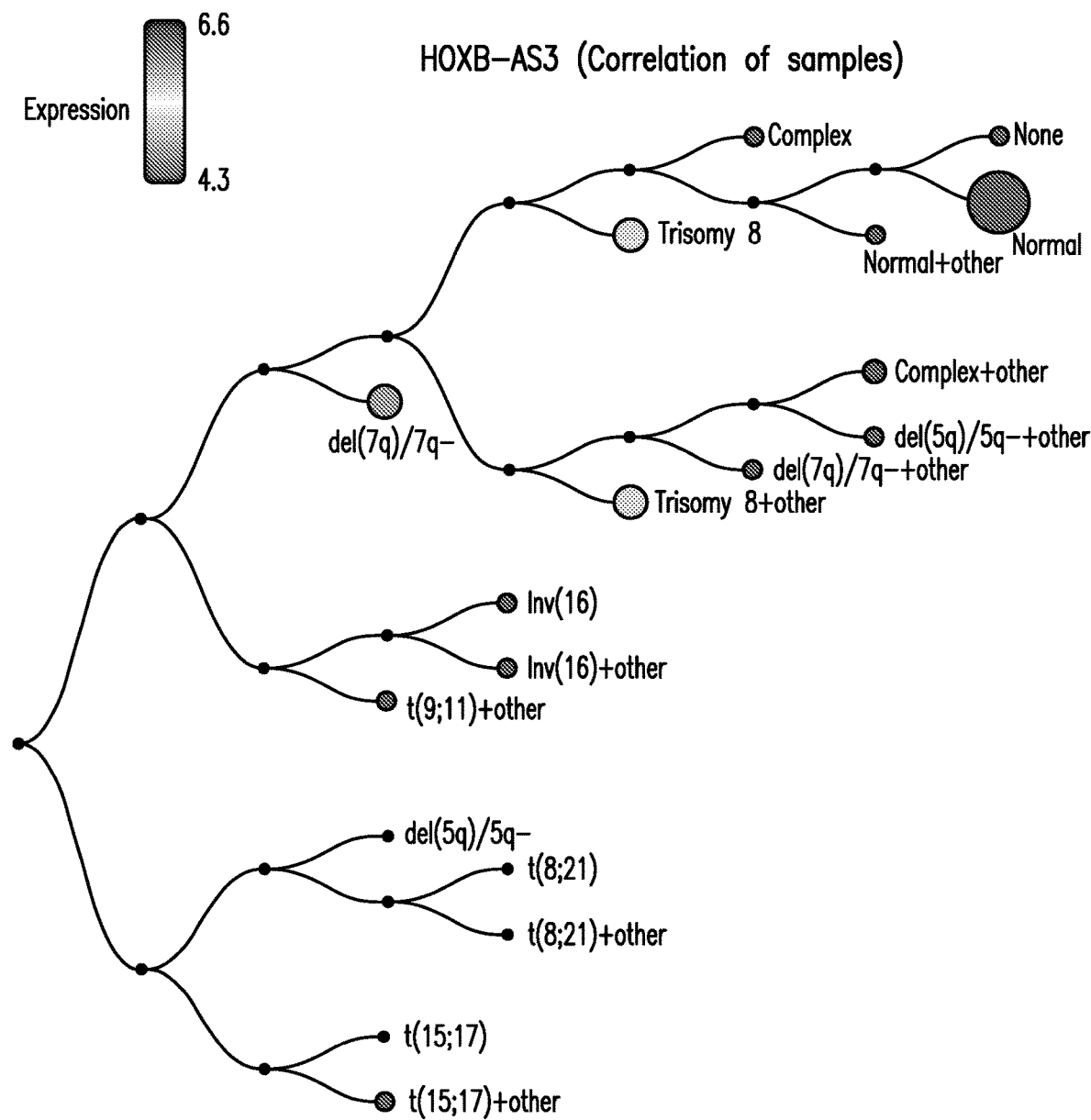
Figure 7C:
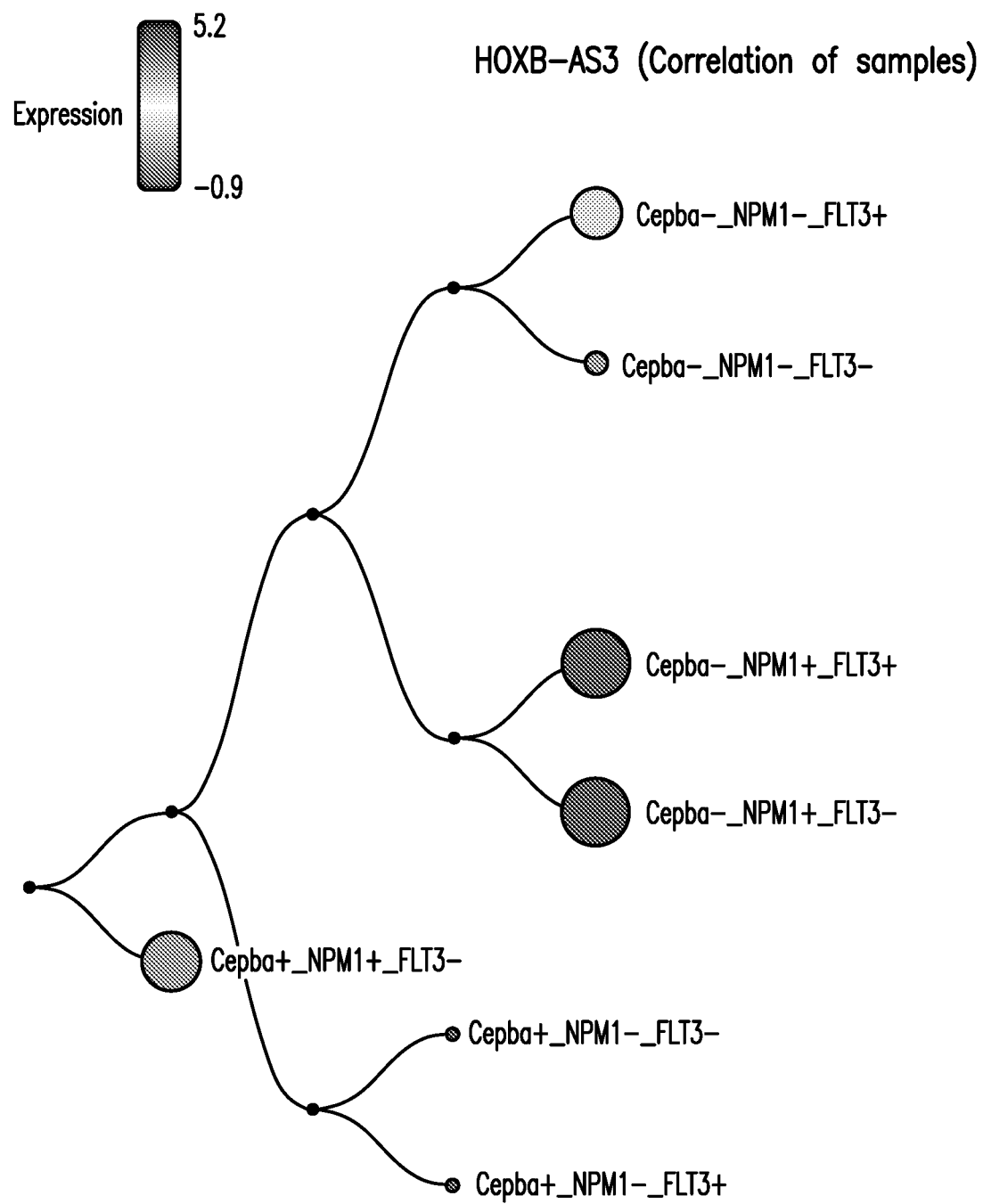

The expression levels of HOXB-AS3 were then analyzed in six different AML cell lines (Kasumi-1, KG1a, MOLM13, MV4-11, OCI-AML3 and THP1: all are NPM1 wt except OCI-AML3) by real-time PCR, custom designed to interrogate the expression of RACE-identified transcripts. Detectable levels of HOXB-AS3 were only found in the NPM1mut OCI-AML3 cells (FIG. 1C). Furthermore, samples from NPA1mut and NPM1 wt AML patients were screened, as well as samples of whole BM cells from healthy donors (n=6 in each group). It was found that HOXB-AS3 was expressed at higher levels in NPM1mut AML patients compared to patients with NPM1 wt (P<0.01) and healthy BM cells (FIG. 1D; P<0.01). There was no significant difference in HOXB-AS3 expression between healthy BM cells and the NPM1 wt samples. In addition, publicly available microarray and RNA sequencing datasets of AML samples and normal hematopoietic cells were also queried (as analyzed by the International Microarray Innovations in Leukemia Study Group and The Cancer Genome Atlas Project. Consistent with these findings, these analyses showed that HOXB-AS3 is not expressed in healthy BM cells and that it is primarily detected in CN-AML samples (FIGS. 7A and 7B). With regard to molecular subsets of CN-AML, HOXB-AS3 was highly expressed in patients who harbored NPM1 mutations independently of the concomitant presence or absence of FLT3-ITD (FIG. 7C).

HOXB-AS3 Overexpression in AML Blasts is Driven by the Presence of NPM1 Mutations.

Figure 1E:
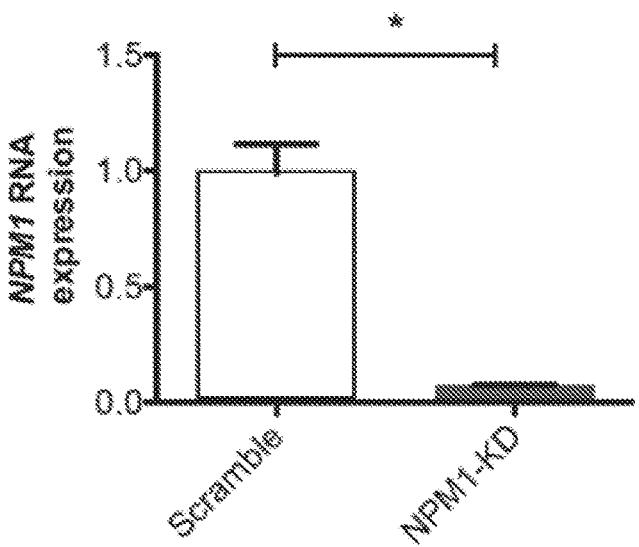
Figure 1F:
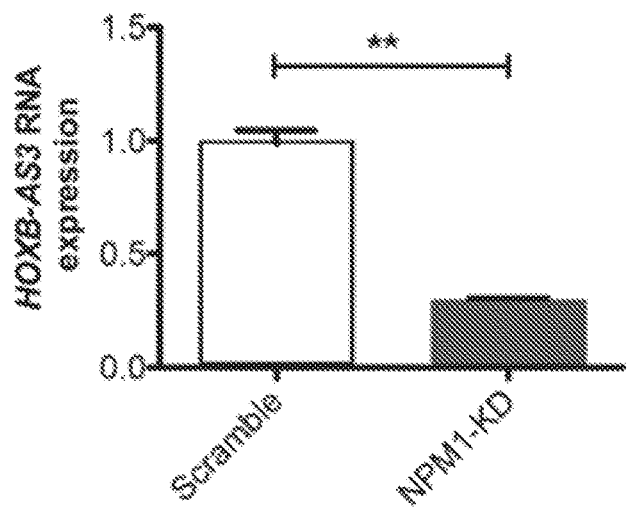
Figure 1G:
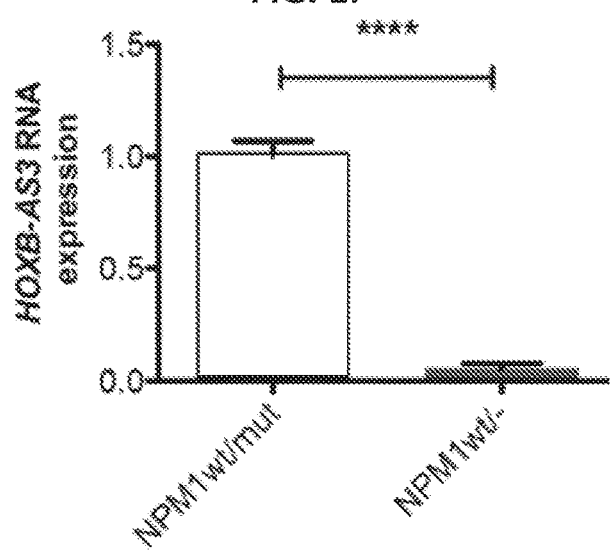

To further examine the association between HOXB-AS3 expression and presence of NPM1 mutations, knock-down (KD) experiments of NPM1 were performed in OCI-AML3 cells. Electroporation-mediated delivery of NPM1-targeting, locked nucleic acid (LNA)-modified oligonucleotides led to significant downregulation of NPM1 mRNA (FIG. 1E; P<0.001). At 48 hours post electroporation, when no differences in apoptosis between cells treated with scramble or anti-NPM1 oligos could be detected KD of NPM1 led to a decrease in HOXB-AS3 expression (FIG. 1F; P=0.003). To further study this association, CRISPRi technology was used to generate genetically modified OCI-AML3 cells, which lack the NPM1mut and express one NPM1 wt allele (NPM1$^{wt/-}$). Genetic removal of the mutated NPM1 allele led to a decrease in the expression of HOXB-AS3 as well as that of the flanking HOXB5 and HOXB6 genes (FIG. 1G; P<0.001).

Figure 1H:
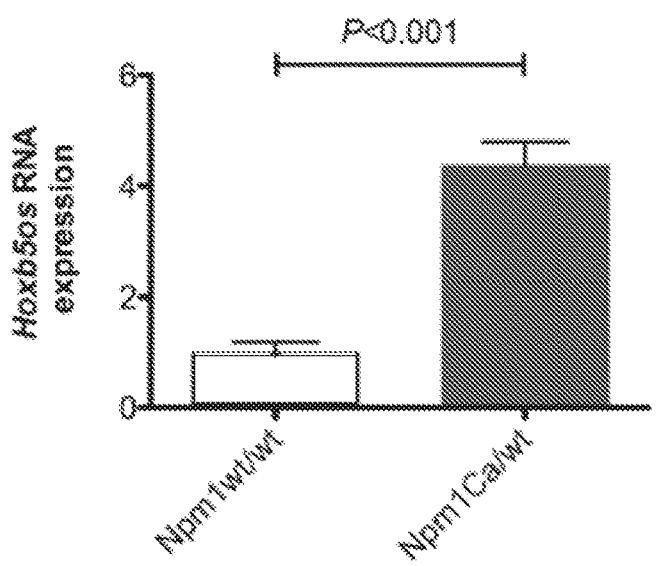

Finally, lineage marker negative progenitor cells were analyzed, which were harvested from bone marrow of NPM1mut transgenic mice and age-matched controls. The expression of a murine lncRNA transcript was measured, which is antisense to the Hoxb5 and Hoxb6 genes and displays a 25% sequence identity to the human HOXB-AS3, named Hoxb5os. As shown in FIG. 1H, Hoxb5os was significantly upregulated in the ATM/mut mice (P<0.001), when compared to the wt controls. Taken together, these data indicate that HOXB-AS3 overexpression in AML blasts is driven by the presence of NPM1 mutations.

HOXB-AS3 Expression Regulates Cell Proliferation in AML Cells

Figure 2A:
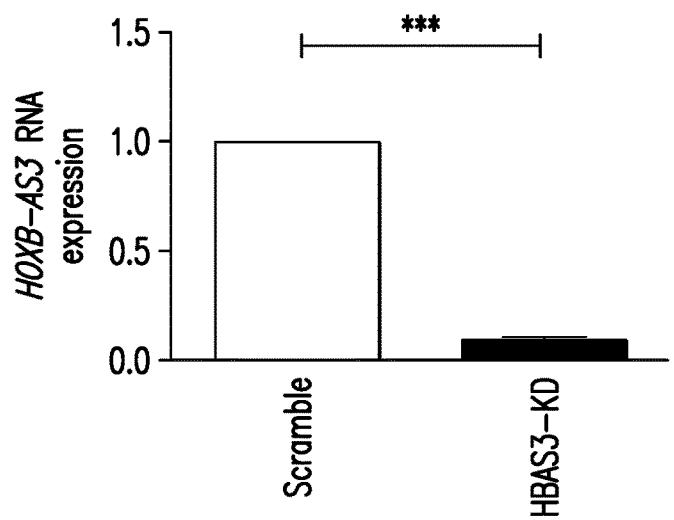
FIG. 2A-2G. In vitro functional significance of the HOXB-AS3 long non-coding RNA in acute myeloid leukemia cells.
Figure 2B:
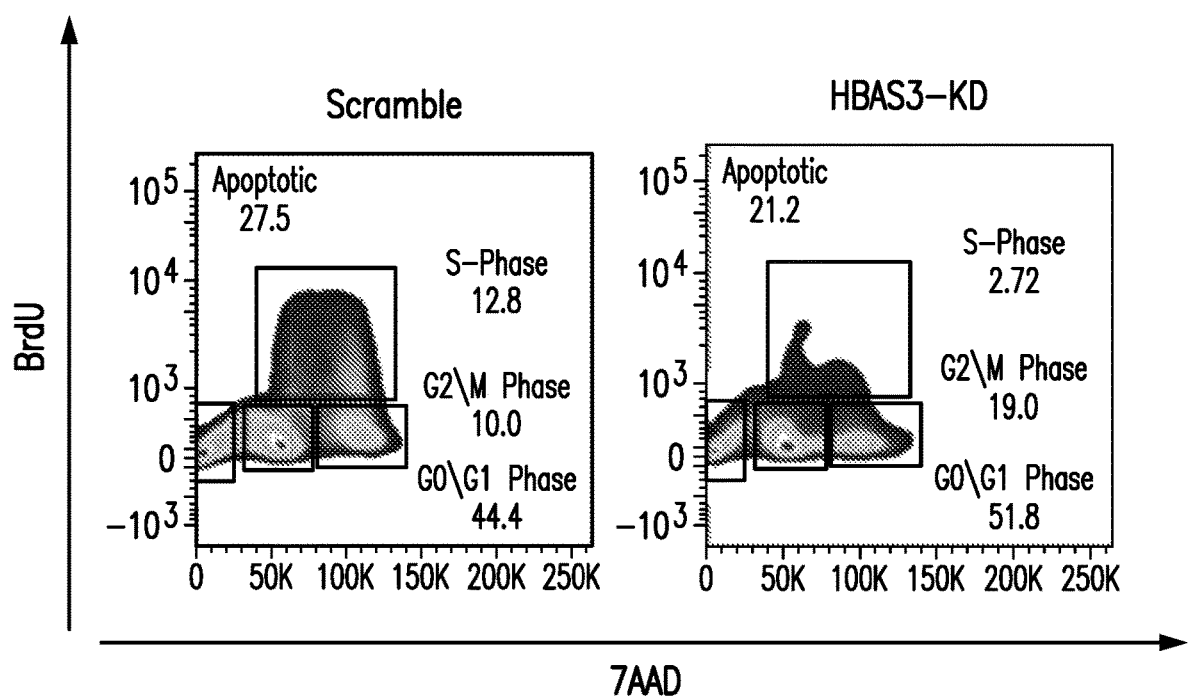
Figure 2C:
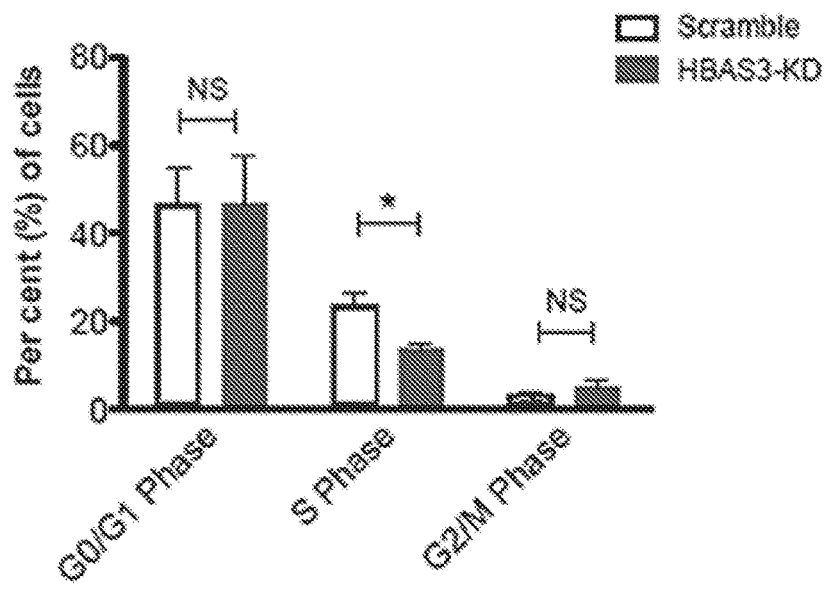
Figure 2D:
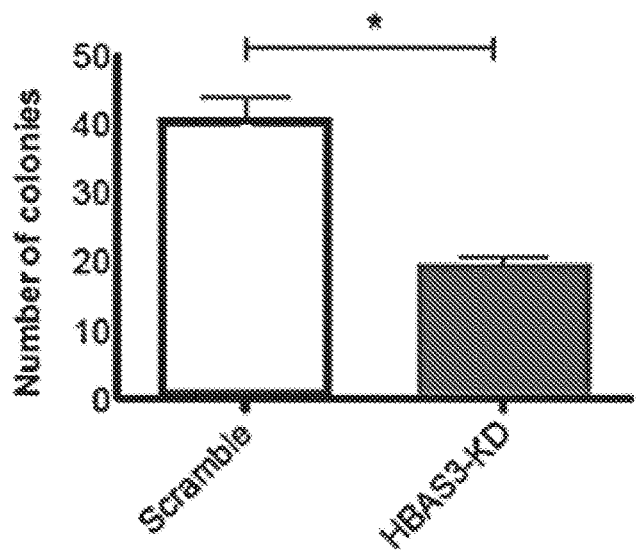
Figure 9A:
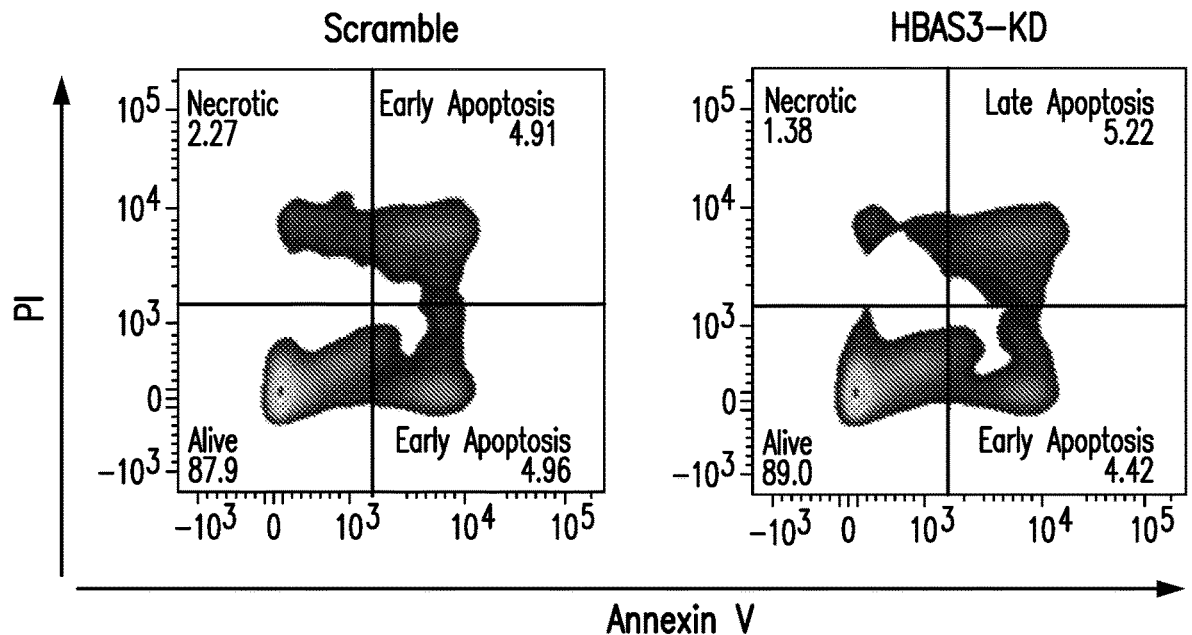
FIG. 9A-9B. Knock-down of the HOXB-AS3 long non-coding RNA does not affect apoptosis in OCI-AML3 cells.
Figure 9B:
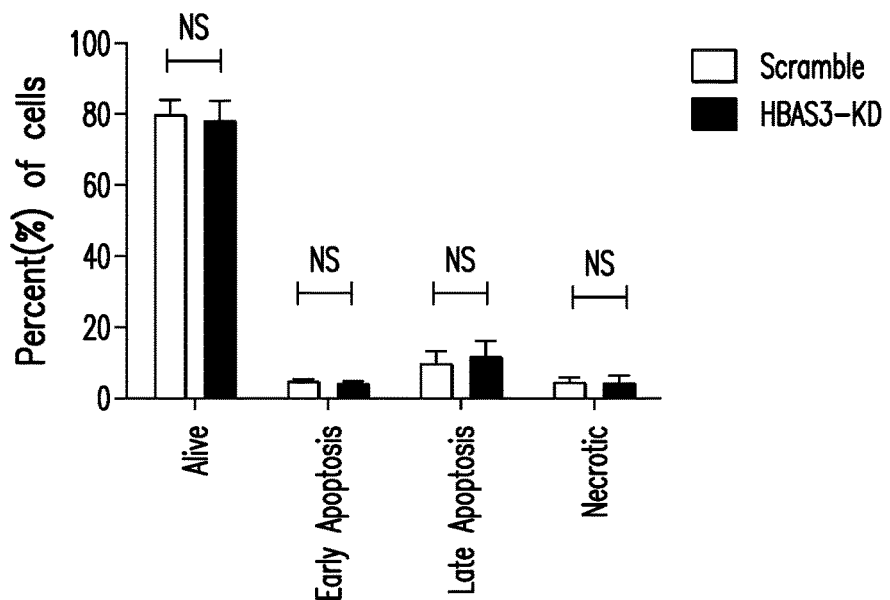

To evaluate the functional significance of HOXB-AS3 expression in NPM1 mutated AML cells, HOXB-AS3-KD experiments were conducted using RNAseH recruiting, LNA-modified gapmers. Delivery of five different oligonucleotides that targeted distinct regions of the four HOXB-AS3 variants to OCI-AML3 cells via electroporation led to significant concomitant downregulation of all HOXB-AS3 transcripts (FIG. 8), suggesting that all variants stem from one common precursor transcript. In all subsequent KD experiments, a mixture of the Gapmers #2 and #3 were used to deplete HOXB-AS3 (FIG. 2A, P<0.001). Cell-cycle analysis based on Bromodiuridine (BrDU) incorporation and 7-Actinomycin D staining revealed a decrease of the proliferating fraction of OCI-AML3 cells upon HOXB-AS3-KD (FIGS. 2B and 2C; P=0.02; S-phase average % in control versus KD: 24% versus 16%). Annexin V/Propidium Iodide (PI) staining analysis showed no difference in apoptosis between the scramble and the HOXB-AS3-KD treated cells (Supplemental FIG. 9. Colony formation unit assays in soft agar revealed a decrease in the colony forming capacity of OCI-AML3 cells after HOXB-AS3-KD (FIG. 2D; P=0.02; mean of colonies in scramble versus HOXB-AS3-KD; 37 versus 18).

Figure 2E:
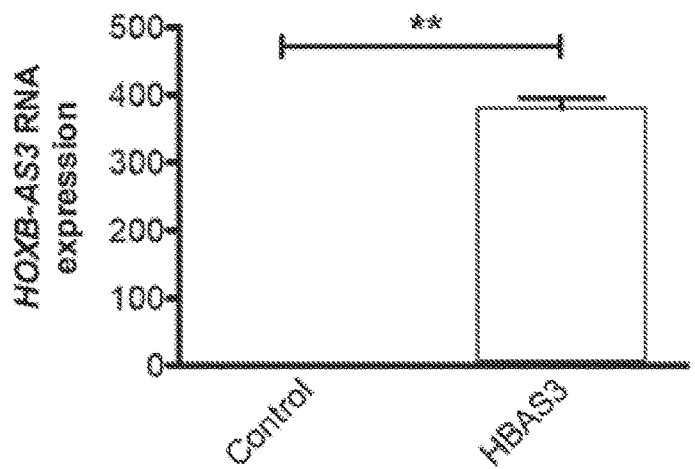
Figure 2F:
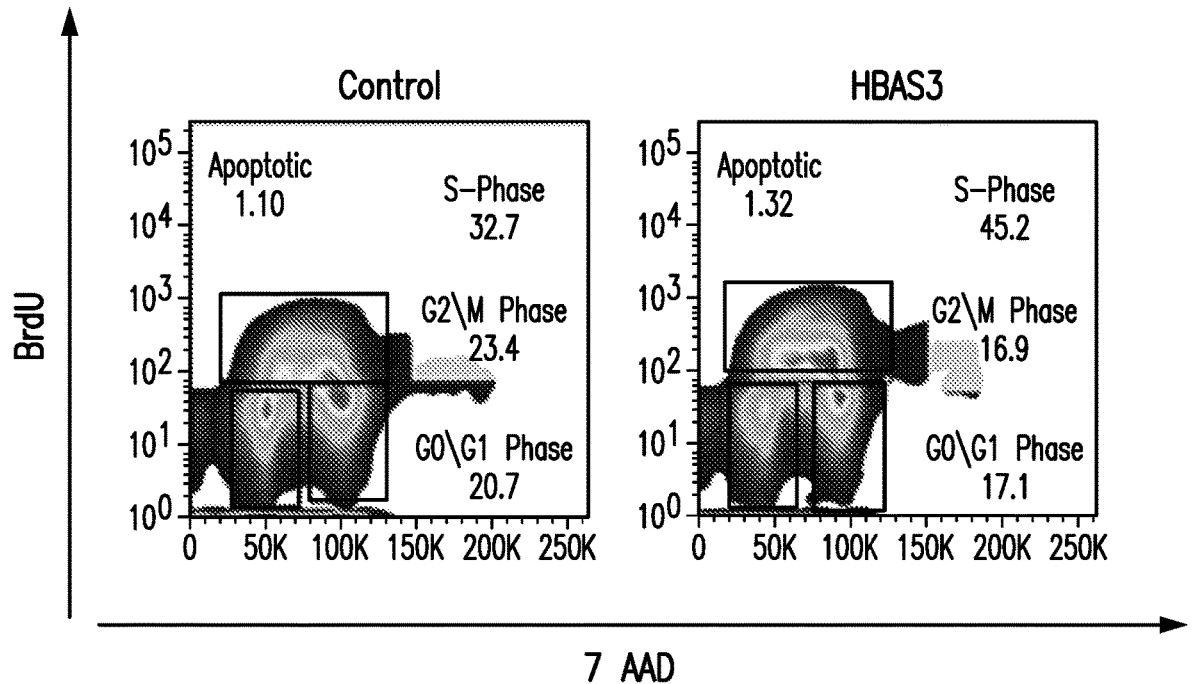
Figure 2G:
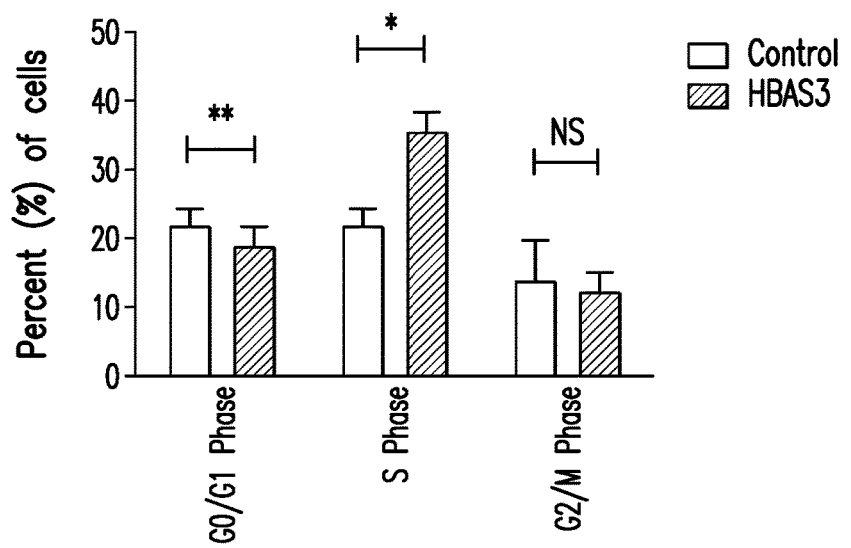

In contrast, overexpression of the HOXB-AS3 in K562 cells (FIG. 2E; P=0.008) led to an increase in the fraction of the proliferating blasts as measured by BrdU-based cell cycle analysis (FIG. 2G; P=0.02; S-phase average % in control versus HOXB-AS3 overexpression: 32% versus 43%), with a concomitant decrease in the percent of cells in the G0-G1 phase (FIG. 2G; P=0.008; G0-G1-phase average % in control versus HOXB-AS3 overexpression: 22% versus 16%, P<0.01): The proliferative phenotype was specifically mediated by overexpression of the transcript variant NR_033202.2, Overexpression of HOXB-AS3 did not affect the viability of K562 cells (Data not shown).

Figure 3A:
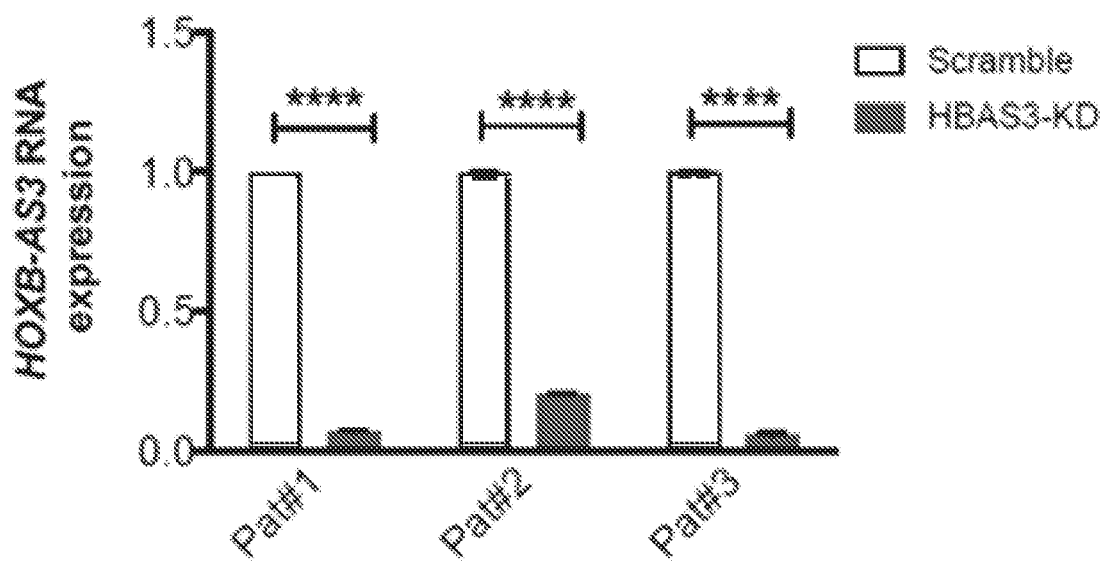
FIG. 3A-3F. In vitro and in vivo evaluation of the functional significance of HOXB-AS3 AML patient blasts.
Figure 3B:
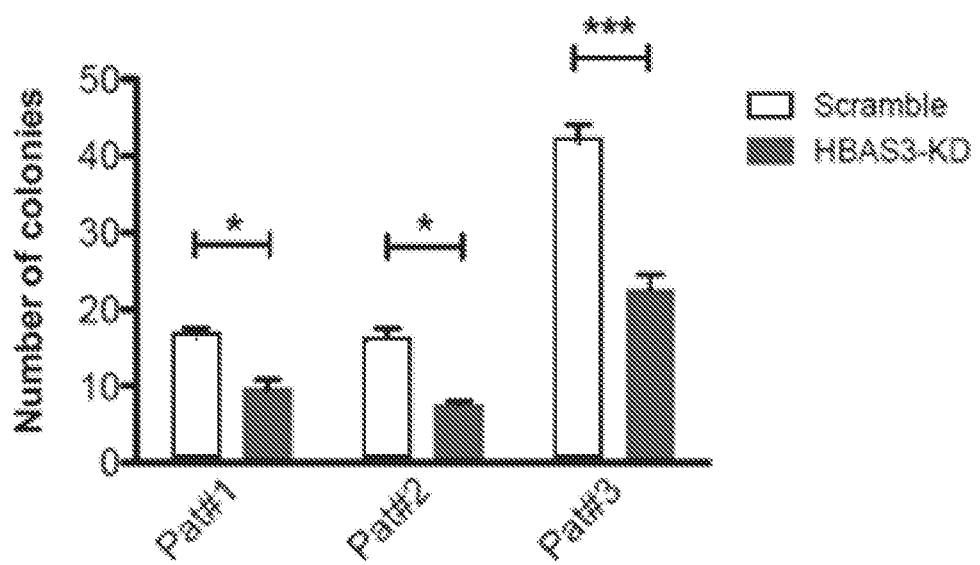

Knock down (KD) experiments were then conducted in blasts of AML patients, who harbored NPM1mut. Delivery of anti-HOXB-AS3 oligonucleotides via electroporation efficaciously targeted and down-regulated HOXB-AS3 expression (FIG. 3A; P<0.001 in all three cases). HOXB-AS3-KD led to a significant decrease in the number of colonies formed by the leukemic blasts in CFU-assays in soft agar, compared to non-targeting scramble control (FIG. 3B).

Figure 3C:
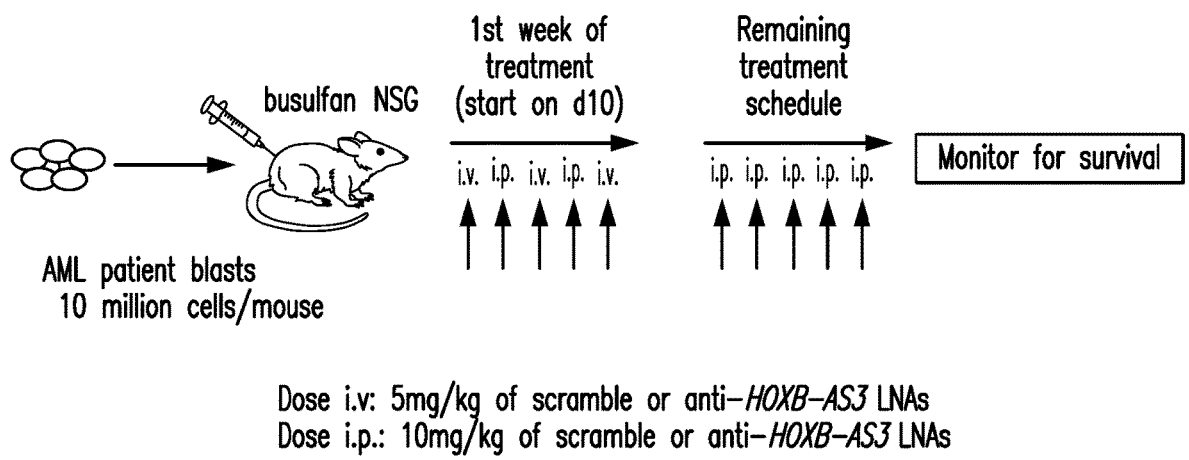
Figure 3D:
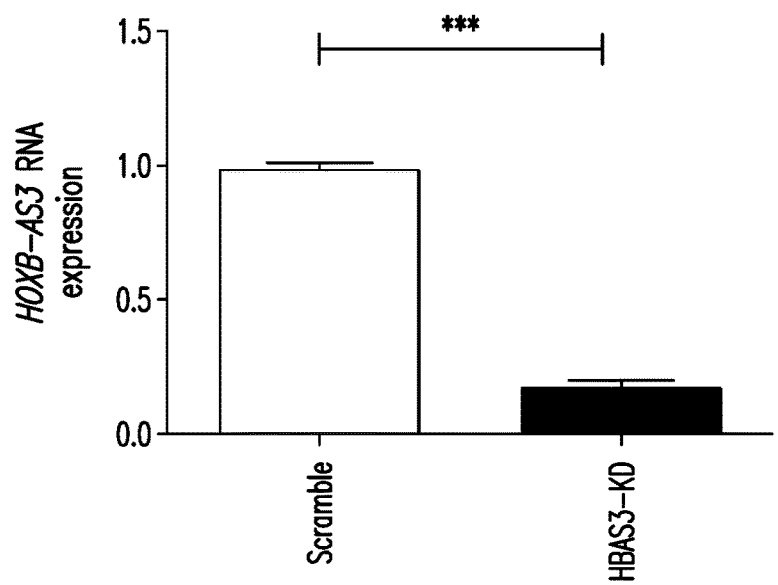
Figure 3E:
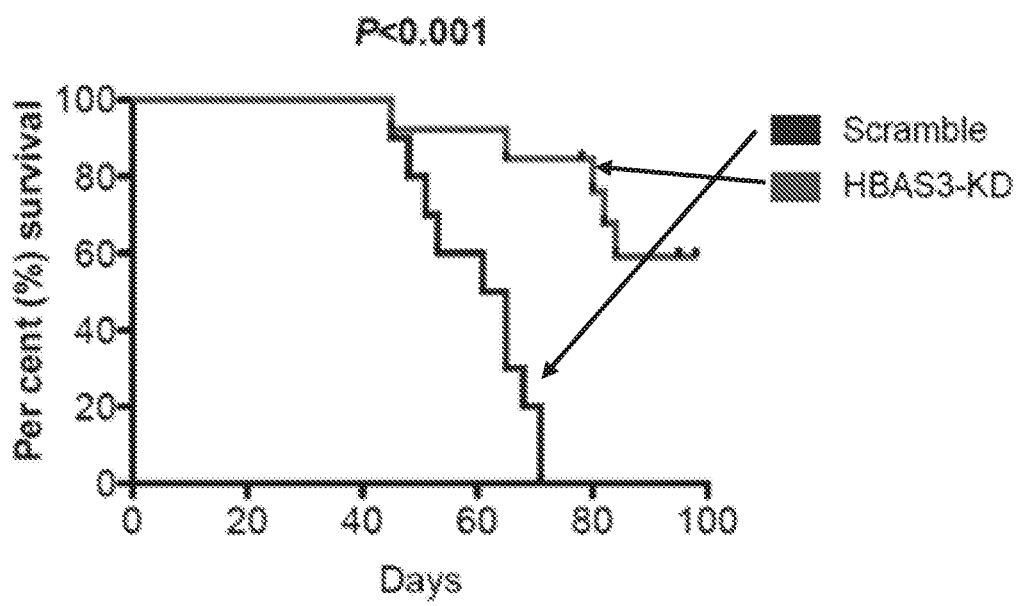
Figure 3F:
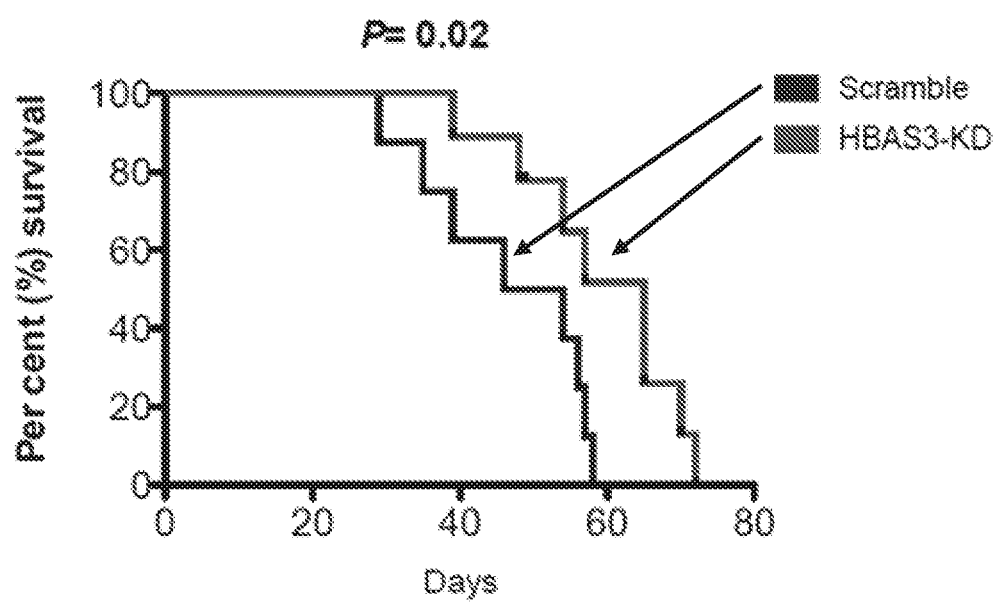
Figure 10A:
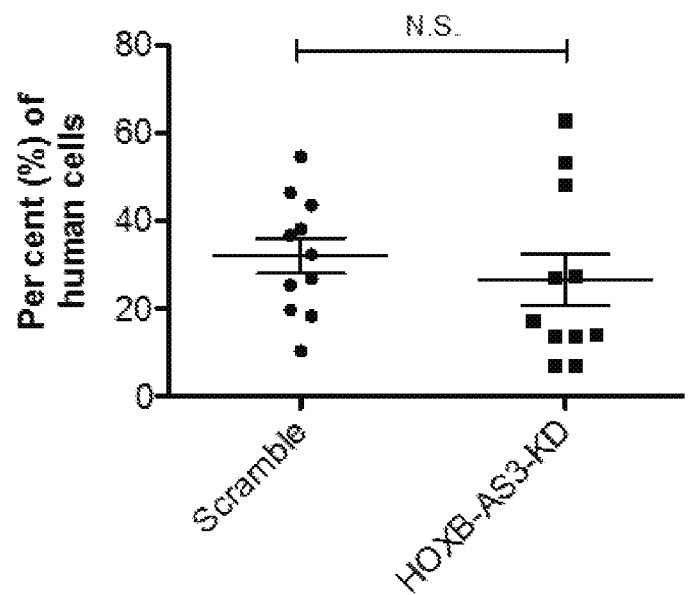
FIG. 10A-10B. Engraftment of human AML blasts in NOD Scid Gamma mouse recipients. Percent of human AML blasts in the peripheral blood of mice engrafted with human AML blasts of patients 1 (FIG. 10A) and 2 (FIG. 10B), who harbor NPM1 mutations, as evaluated by staining for the human CD45 and the murine CD45.1 antigens and flow cytometric analyses. Mice were randomly assigned to receive scramble non-targeting control or anti-HOXB-AS3 treatment. NS indicates not significant.
Figure 10B:
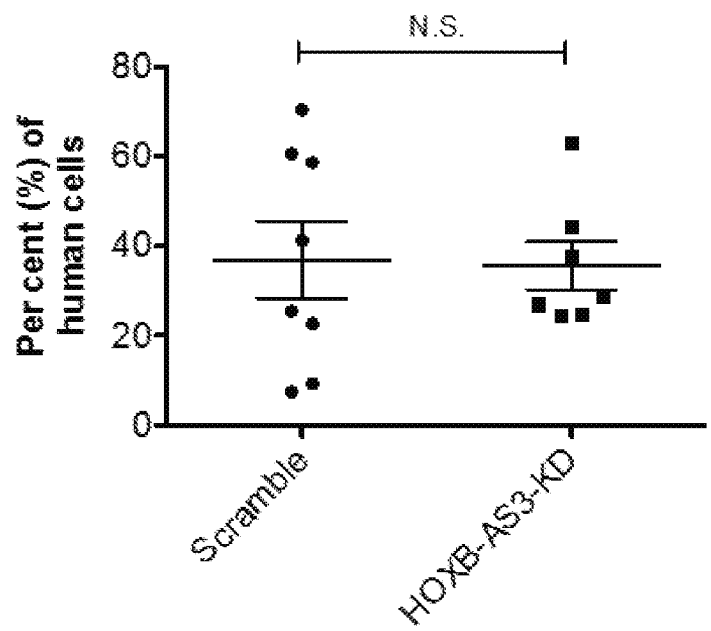

In Vivo Depletion of HOXB-AS3 Prolongs Survival of Mice Xenotransplanted with NPM1mut Patient AML Blasts In order to evaluate the in vivo effect of HOXB-AS3-KD in AML blasts, experiments were conducted in patient-derived xenograft mouse models. In brief, a modification of a previously described protocol was used to transplant Busulfan-pre-treated Nod Scid Gamma (NSG) mice with unselected leukemic blasts of two AML patients, who harbored NPM1mut. Mice were randomly divided into a group which received nanoparticle-formulated LNA-modified anti-HOXB-AS3 oligos or similarly formulated non-targeting scramble control. A schematic overview of the treatment protocol and experimental design is provided in FIG. 3C. A small cohort of mice engrafted with blasts of patient #2 was treated for two weeks and was then sacrificed to evaluate the efficacy of the in vivo HOXB-AS3-KD. Treatment with anti-HOXB-AS3 oligos led to significant down-regulation of HOXB-AS3 expression in human-CD45 selected AML blasts, which were isolated form the bone marrow of the treated mice (FIG. 3D; P<0.001). Larger cohorts of mice engrafted with blasts of patient#1 and patient #2 were treated and monitored for survival. Mice were evaluated for engraftment on day 42 post-transplant by flow cytometry analysis of peripheral blood and evaluation of human CD45 and murine CD45.1 expression. In the xenografts of both patients there was no significant difference in the engraftment of human leukemia in the scramble treated versus the HOXB-AS3-KD treated groups (FIG. 10). For both NPM1mut xenograft models, in vivo HOXB-AS3-KD led to significant prolongation of the survival of the treated mice compared to the non-targeting scramble control. In xenografts of patient #1, the median survival of the scramble treated mice (n=10) was 62 days whereas the median survival of the HOXB-AS3-KD treated groups (n=11) was not reached after 100 days of treatment (FIG. 3E, P<0.001). In xenografts of patient#2 the median survival of the scramble treated atm (n=7) was 42 days and that of the HOXB-AS3-KD arm (n=8) was 58 days (FIG. 3F P=0.02). Interaction of HOXB-AS3 with the Protein-Coding Transcriptome of NPM1mut AML Blasts.

To study the molecular pathways that are regulated by HOXB-AS3, additional analyses were performed in the cohort of 377 younger CN-AML patients who were previously studied with RNAseq. The initial focus was on the NPM1 mutated subpopulation and correlation analysis of HOXB-AS3 expression with protein-coding mRNA transcripts was performed. Pathway analysis revealed that genes involved in RNA-processing, ribosome biogenesis and DNA repair response are enriched in patients with high HOXB-AS3 expression. Furthermore, RNA sequencing was performed in scramble versus HOXB-AS3-KD treated OCI-AML3 cells as well as blasts of three NPM1mut AML patients. Pathway analyses revealed that genes involved in DNA damage response were upregulated.

Figure 4A:
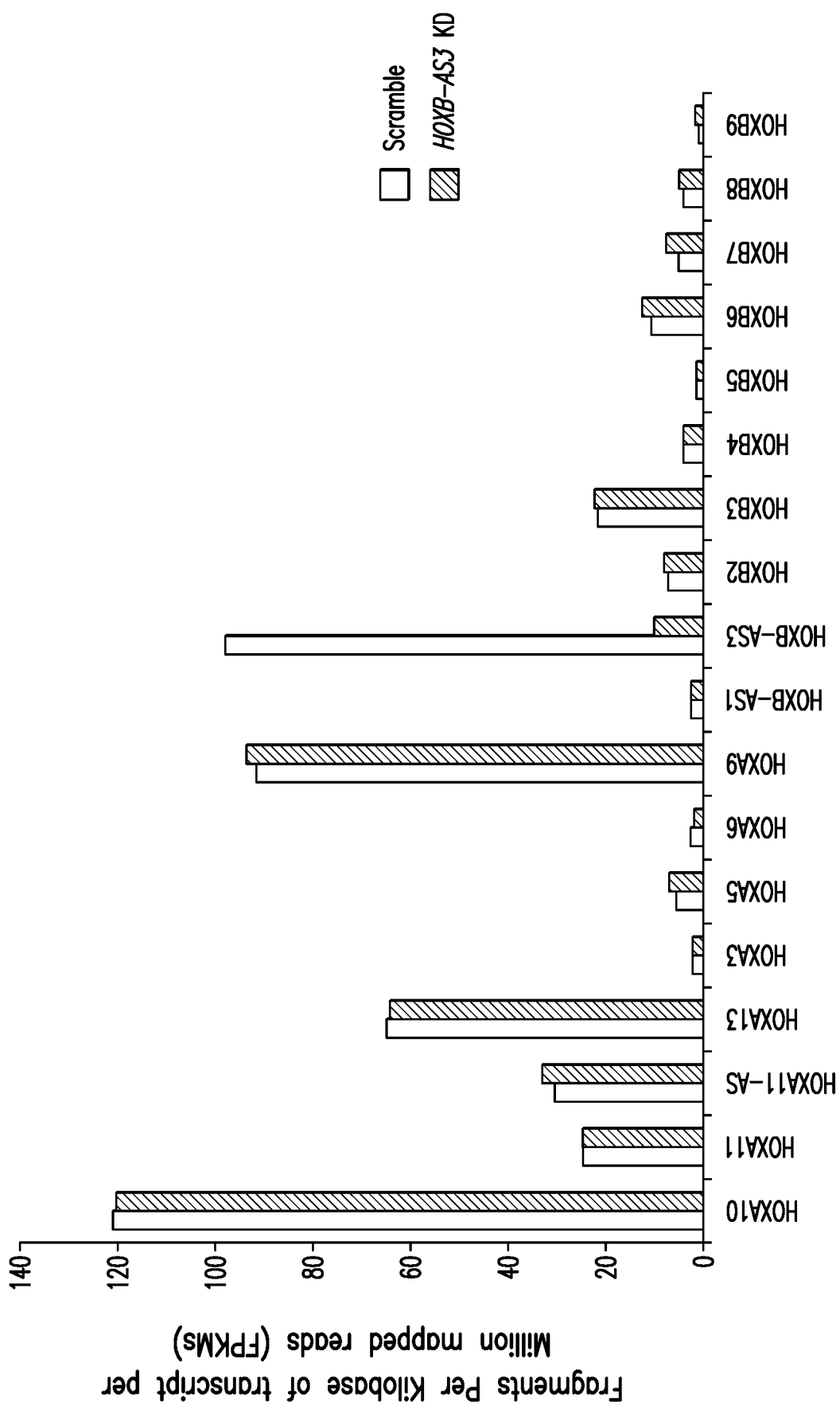
FIG. 4A-4L. Interactions of the HOXB-AS3 long non-coding RNA with the transcriptome and proteome of OCI-AML3 cells.

Since several HOX-loci-embedded lncRNAs have been shown to play a significant role in cancer by regulating (in cis or trans) expression levels of HOX genes, it was specifically examined whether HOXB-AS3-KD affected the expression of HOX genes, in particular the NOXA and HOXB clusters, which are upregulated in NPM1mut CN-AML. It was found that HOXB-AS3-KD had no effect on the expression levels of any of the HOXB and HOXA loci that were overexpressed in the OCI-AML3 cells (FIG. 4A). Since HOX49 is highly expressed in NPM1mut CN-AML and is relevant for leukemogenesis, HOXA9 protein expression was also assessed by western blotting after HOXB-AS3 KD in OCI-AML3 cells. In concordance with the RNA seq data, no difference between controls and HOXB-AS3 KD was detected.

Interaction of HOXB-AS3 with the Proteome of NPM1mut AML Cells

Figure 4B:
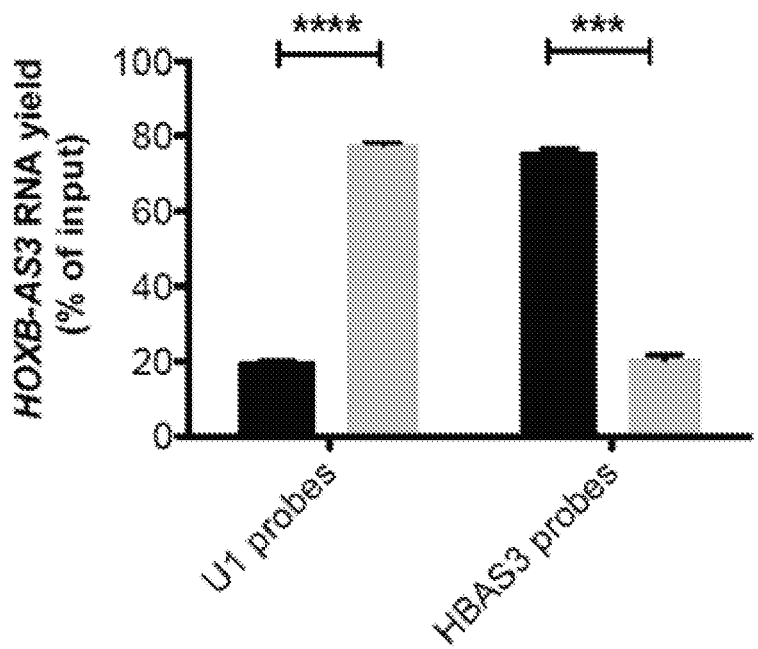
Figure 4C:
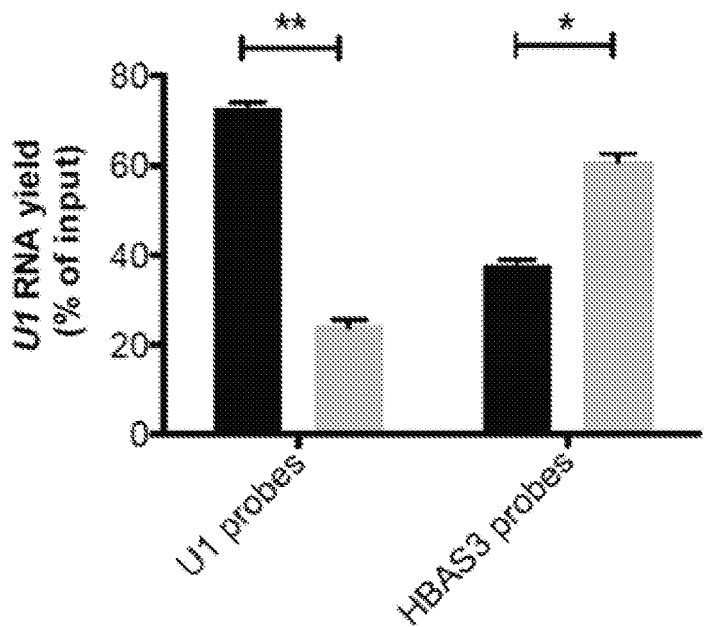
Figures 4D, 4E:
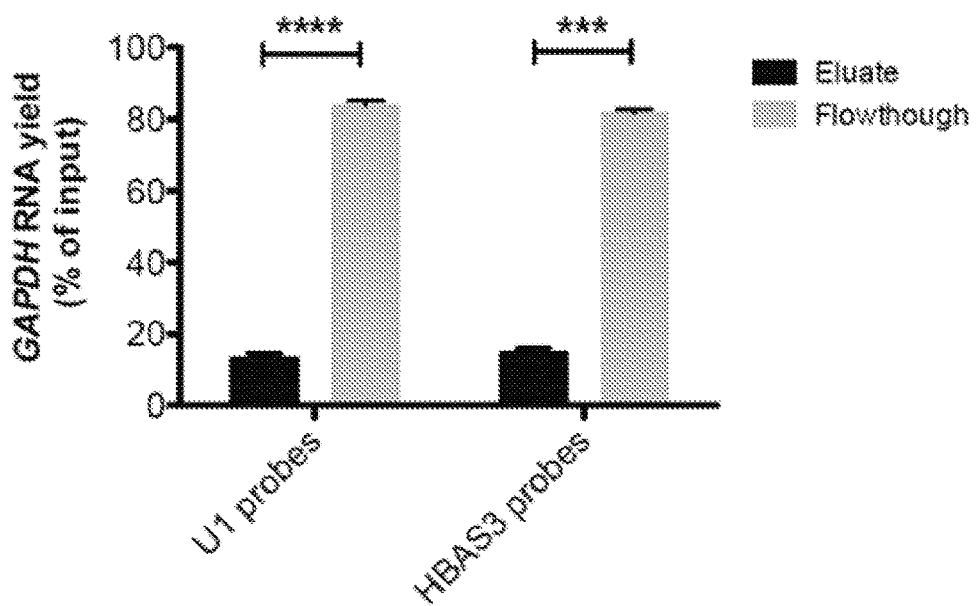

To further study the mechanism by which HOXB-AS3 modulates cell proliferation, RNA-protein complex pull-down experiments were performed to identify the interactions of HOXB-AS3 with the proteome of NPM1mut AML cells. A modified version of the RNA-antisense purification technique was used, as previously described by McHught et al. (McHugh CbA, Chen C K, Chow Al et al. The Xist lncRNA interacts directly with SHARP to silence transcription through HDAC3. *Nature,* 2015; 521(7551):232-236). In brief, biotinylated probes that are complementary to the HOXB-AS3 lncRNA or the U1 transcripts were incubated with UV-cross-linked lysates of OCI-AML3 cells and allowed to hybridize. Streptavidin-coated magnetic beads were used for the purification of the RNA-protein complexes, which were then subjected either to RNA isolation and real-time PCR (RT-PCR) or mass-spectrometry analyses. RT-PCR analyses showed that a high percent of the targeted RNA transcripts could be purified from the hybridized lysates with high specificity (FIGS. 4B-4D). Comparative analysis of the putative U1 and HOXB-AS3 interacting proteins, as identified by mass spectrometry analyses was conducted and the results are listed in FIG. 4E. Four proteins, previously reported to form the U1-complex (SN-RPA, SMD2, SMD3 and RUXE) were included in the list of the identified U1-interactors, validating the efficacy of the approach.

Figure 4F:
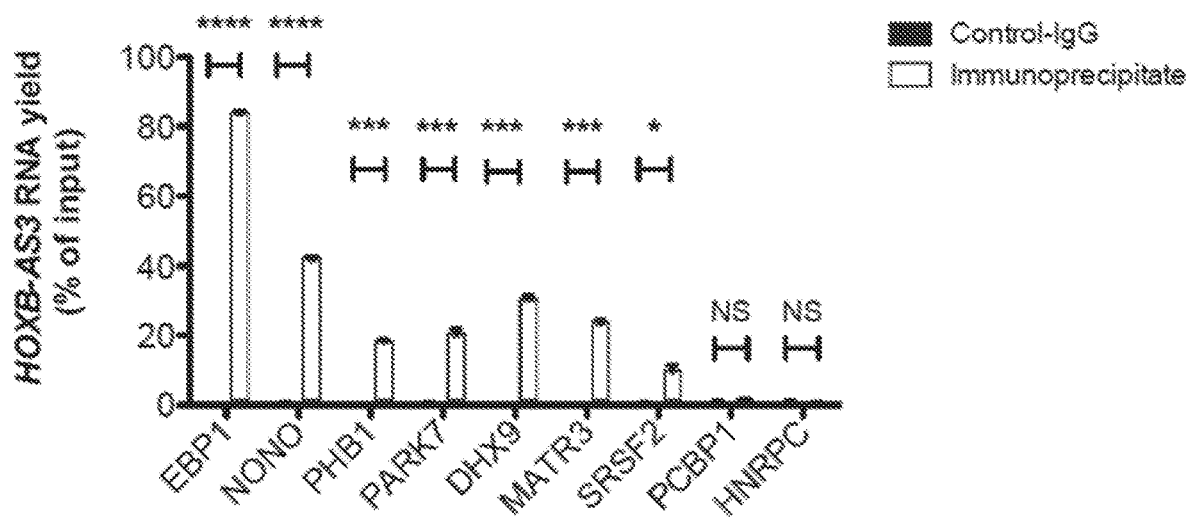
Figure 4G:
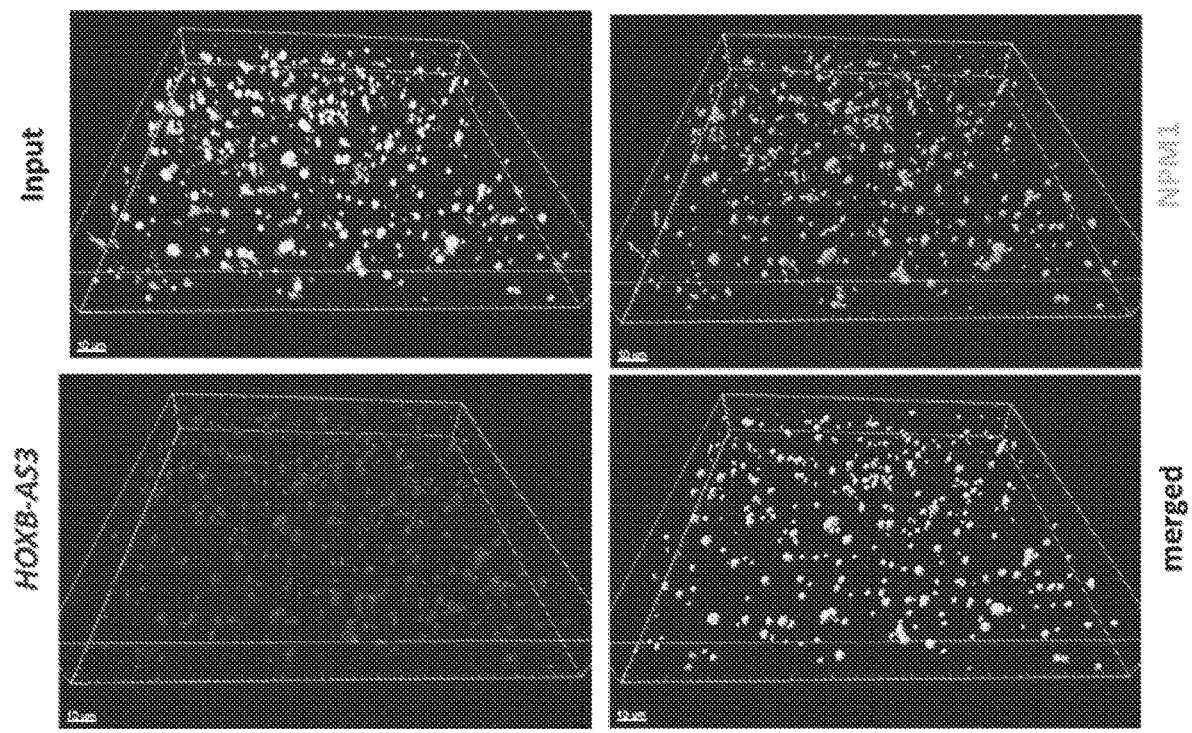
Figure 4H:
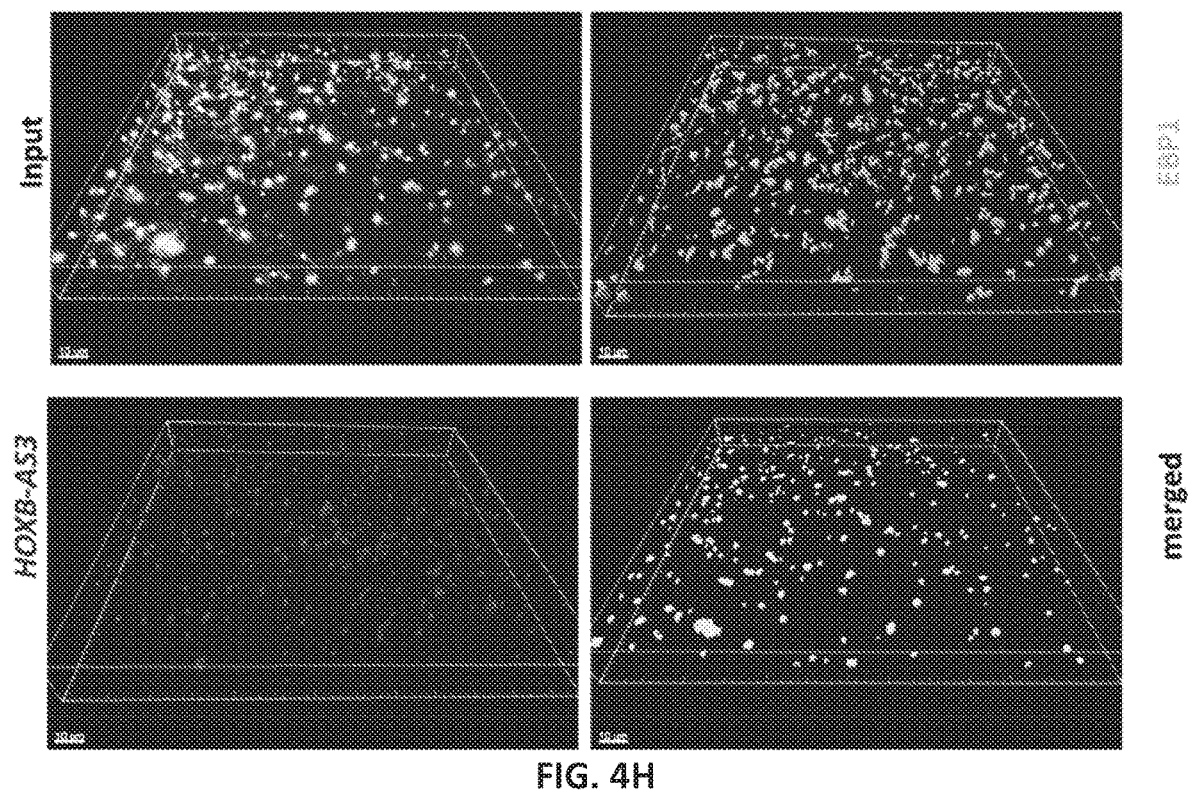
Figure 4I:
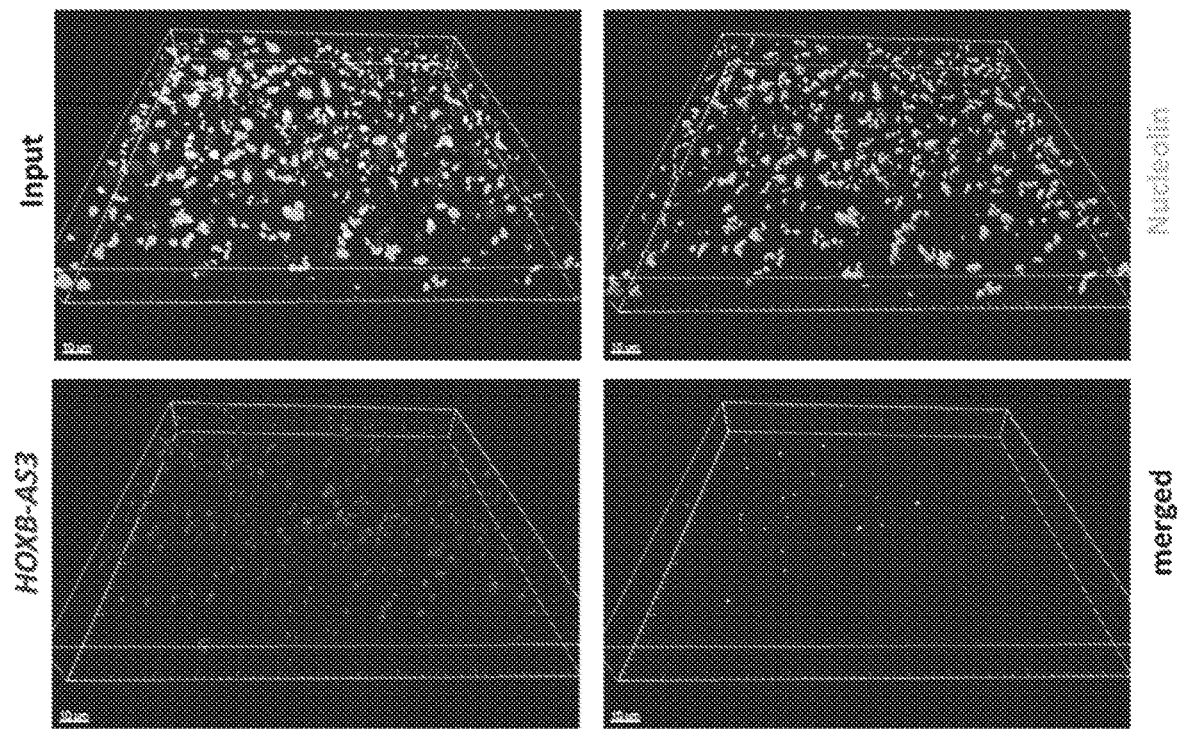

Twenty-two RNA-binding proteins were identified as putative HOXB-AS3 interactors. Validation experiments were performed with nine of the 22 identified proteins by RNA immunoprecipitations. Significant enrichment of HOXB-AS3 was found in the respective immunoprecipitates in seven of the nine proteins (FIG. 4F). The validated HOXB-AS3-binding proteins showed specificity with regard to the HOXB-AS3 transcripts, with which they interacted (EBP1, NONO, DHX9, and PARK7 interacted with the NR_033202.2 and/or the NR_0332023.1 transcripts, whereas MATR3, SRSF2 and PHB1 interacted with the NR_033201.2 and/or the uc060gwg. 1 transcripts). EBP1 was shown to bind to HOXB-AS3 most avidly, as it bound to approximately 80% of the measured HOXB-AS3 in input samples. In addition, in vitro KD of EBP1 in OCI-AML3 cells generated a similar phenotype to HOXB-AS3-KD, a decrease in the proliferating fraction of the cells with no significant effect on apoptosis.

Figure 4L:
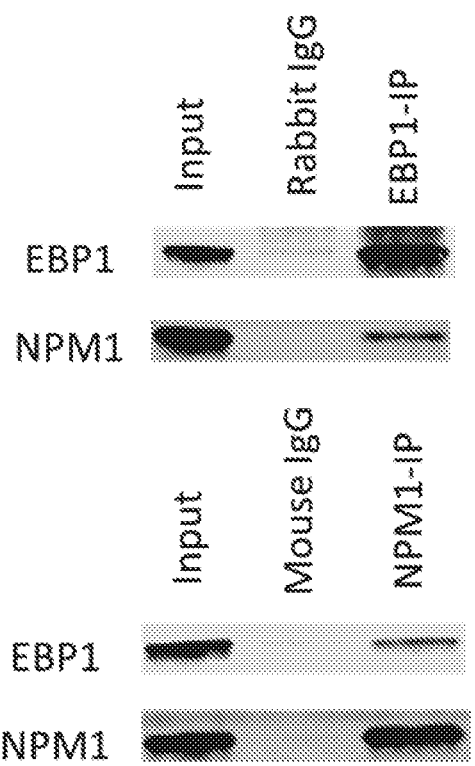
Figure 5A:
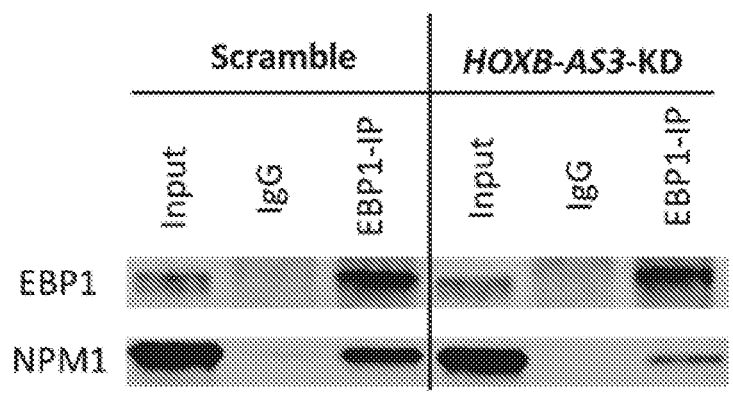
FIG. 5A-5M, HOXB-AS3 long non-coding RNA regulates ribosomal RNA transcription and ribosome biogenesis in acute myeloid leukemia blasts.

EBP1 is an RNA binding protein which regulates a variety of cellular functions, such as proliferation, cell cycle progression and response to cellular stress, EBP1 has been reported to interact with NPM1 and regulate transcription of ribosomal RNA species transcription and ribosome biogenesis in AML cells. The interaction of EBP1 and NPM1, proteins in the presence of NPM1 mutations was investigated by co-immunoprecipitation experiments in nuclear lysates of OCI-AML3 cells. It was found that EBP1 and NPM1 interact as shown by immunoprecipitation experiments of either of the two proteins, followed by western blotting (FIG. 4L. As both wt and mutant NPM1 proteins are expressed in OCI-AML3 cells, similar immunoprecipitation experiments were performed with an antibody which specifically recognizes the C-terminus of the mutated NPM1 protein. Only a small amount of the mutated protein could be isolated from nuclear lysates and this was not found to interact with the EBP1 protein (FIG. 5A).

Figures 4J, 4K:
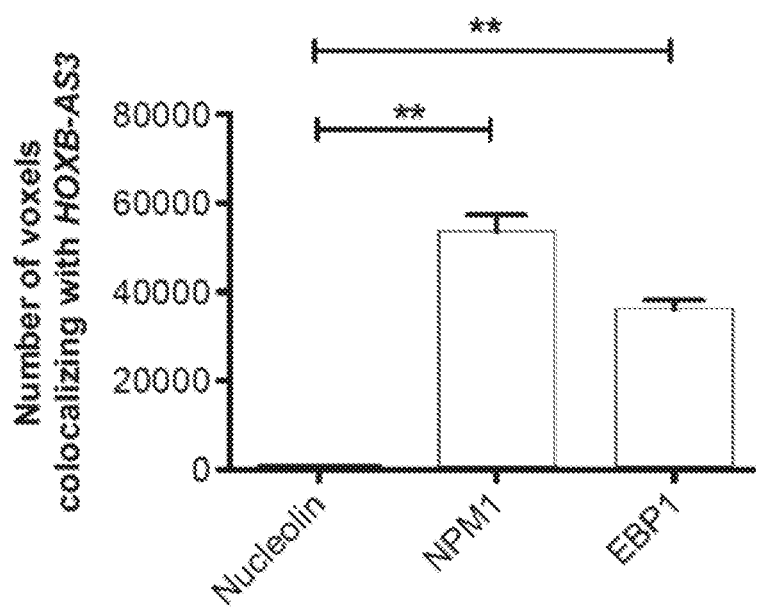

To further study the interaction of HOXB-AS3 with its binding proteins and to dissect the cellular localization of the lncRNA, direct visualization experiments were performed using the RNAScope assay and custom designed probes, which specifically targeted the NR_033202.2 transcript. Co-staining with DAPI showed that the HOXB-AS3 lncRNA is located in the nucleus, Concomitant immunostaining was performed of the EBP1 and the NPM1 proteins, as well as of the RNA-binding protein Nucleolin, which was not predicted to interact with HOXB-AS3, as a control. Analyses of the generated images showed a high degree of intra-nuclear interaction of HOXB-AS3 with the NPM1 and the EBP1 proteins, in contrast to Nucleolin. The number of visualized voxels co-localizing with HOXB-AS3 was 60000 for NPM1, 42000 for EBP1 and 169 for Nucleolin. The Pearson correlation co-efficient of co-localization was 0.72 for NPM1, 0.82 for EBP1 and 0.19 with Nucleolin (FIG. 4K).

Figure 5B:
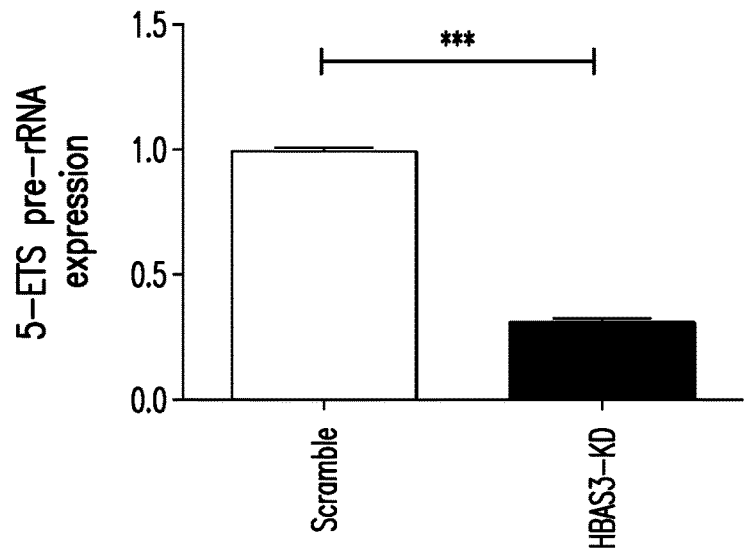
Figure 5C:
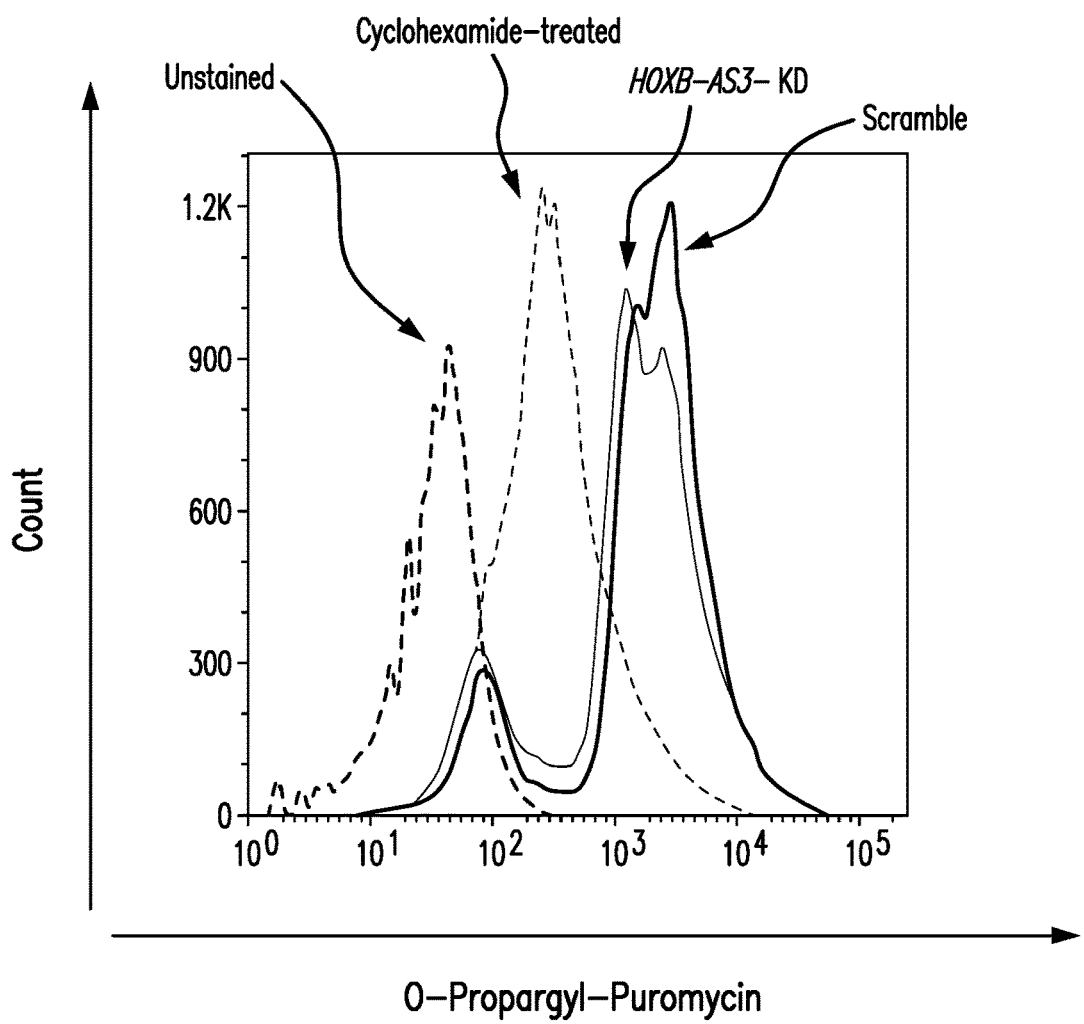
Figure 5D:
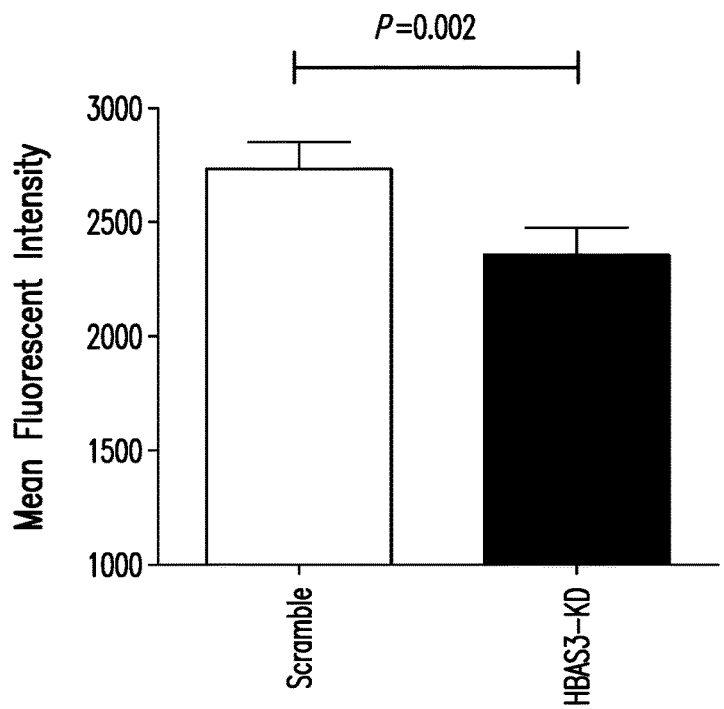
Figure 5E:
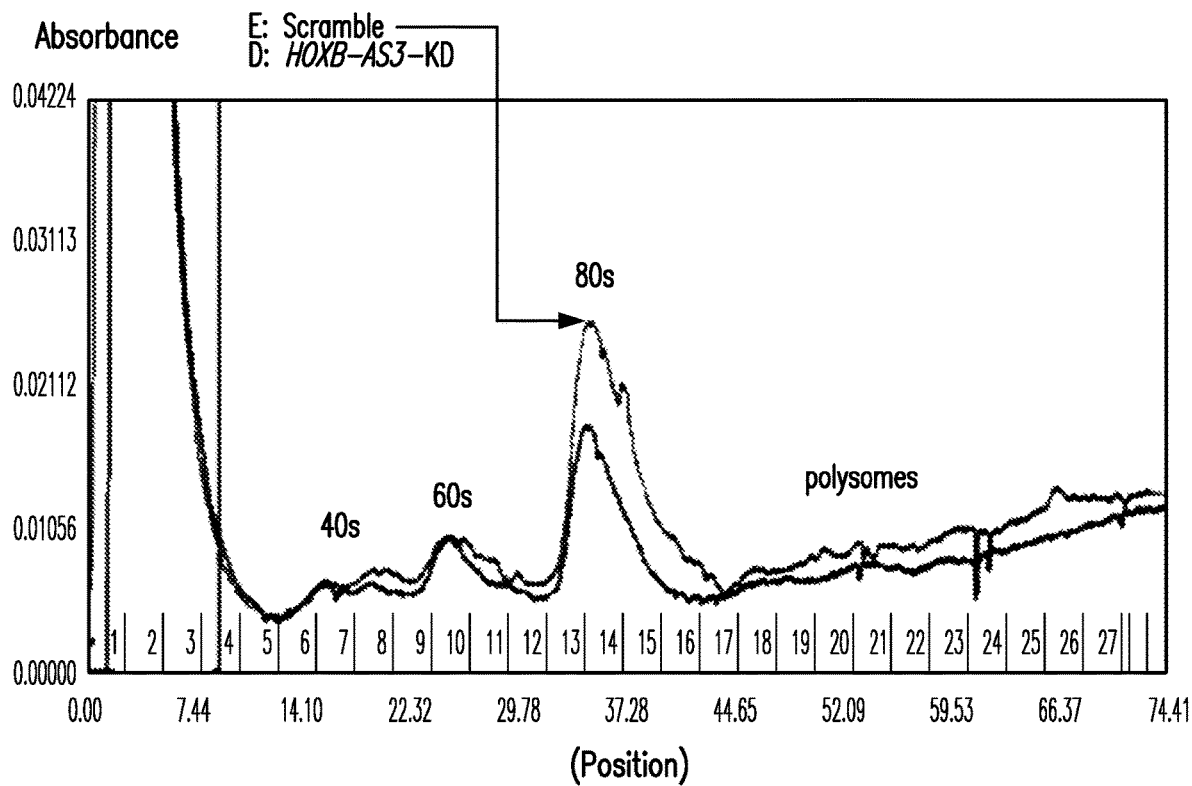
Figure 5F:
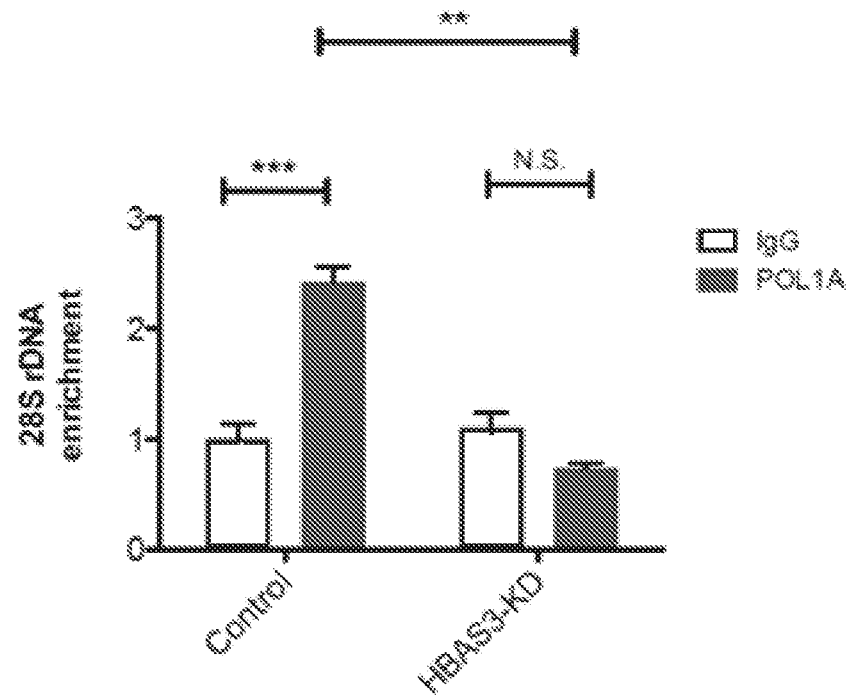
Figure 5G:
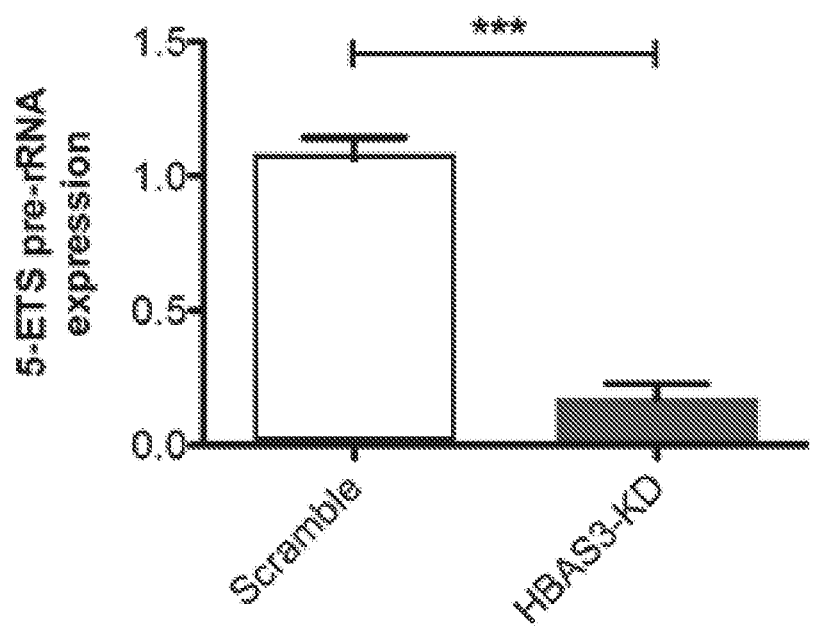

Regulation of Ribosomal RNA (rRNA) Transcription and Ribosome Biogenesis by the HOXB-AS3-EBP1-NONO-NPM1 Ribonucleoprotein Complex As mentioned previously, EBP1 has been shown to interact with NPM1 in the nucleus and to regulate rRNA transcription and ribosome biogenesis in AML cells. To investigate whether HOXB-AS3 modulates ribosome biogenesis in NPH1mut CN-AML, it was investigated how the HOXB-AS3 levels affect the formation of the EBP1-NPN1 complex. As shown in FIG. 5A, depletion of HOXB-AS3 in OCI-AML3 cells led to a decrease in the interacting amount of EBP1 and NPM1, as evaluated by co-immunoprecipitation experiments. The effect of HOXB-AS3 KD in rRNA transcription and ribosome biogenesis was also investigated. HOXB-AS3-KD led to a decrease in the abundancy of the transcribed rRNA in OCI-AML3 cells (FIG. 5B, P<0.001). In addition, chromatin-immunoprecipitation experiments with an RNA Polymerase I (POL1RA) binding antibody showed that HOXB-AS3-KD led to a reduction in the occupancy of the rDNA promoter by POL1RA (FIG. 5F; P<0.01). With regard to ribosome biogenesis, sucrose gradient-mediated polysome profiling in OCI-AML3 cells showed a reduction in the formed polysomes upon HOXB-AS3-KD. This reduction primarily concerned the 80S fraction of the formed polysomes (FIG. 5E). Consistently, in vitro labelling of the de novo synthesized polypeptides in OCI-AML3 cells by incorporation of O-propargyl-puromycin (OPP) and fluorochrome-conjugation, showed that HOXB-AS3-KD led to a reduction of protein synthesis in the OCI-AML3 cells, when compared to scramble control (FIG. 5D; P=0.02). Finally, short-term in vivo treatment of human AML blasts in murine PDX models revealed that HOXB-AS3-KD led to a decrease in the amount of transcribed rRNA species and a decrease (FIG. 5B; P<0.001) in the de novo protein synthesis in these cells (FIG. 5G).

Figure 5H:
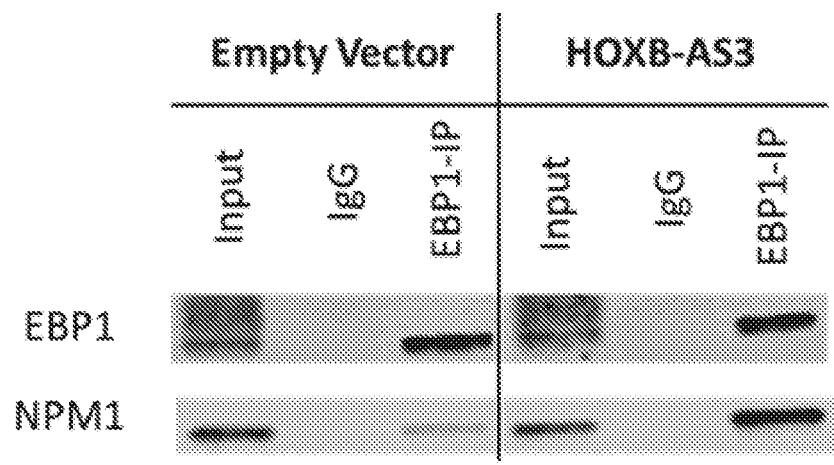
Figure 5I:
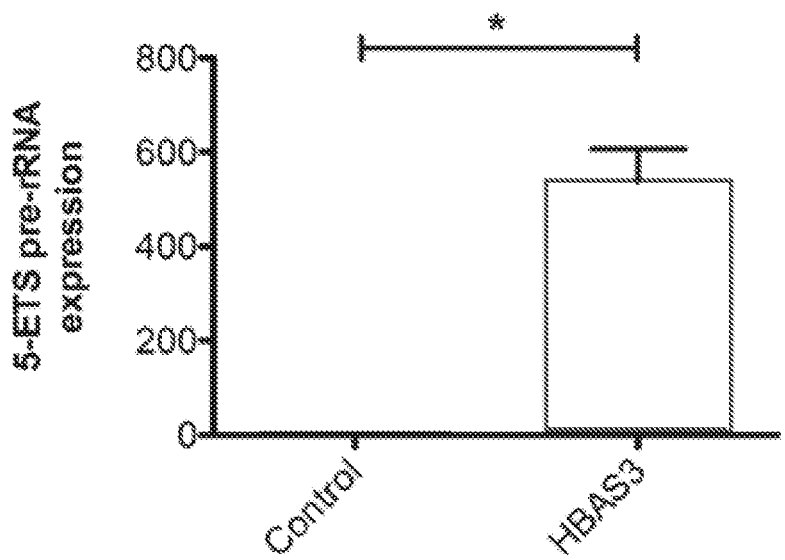
Figure 5J:
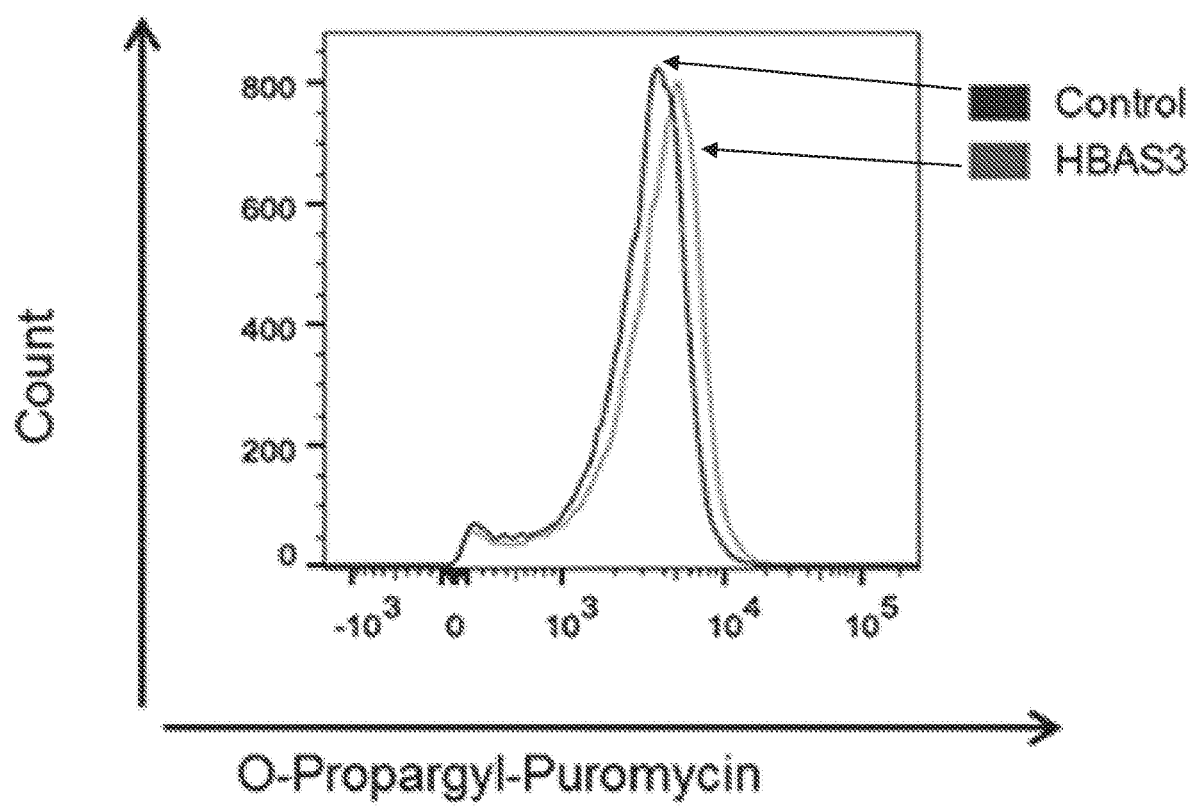
Figure 5K:
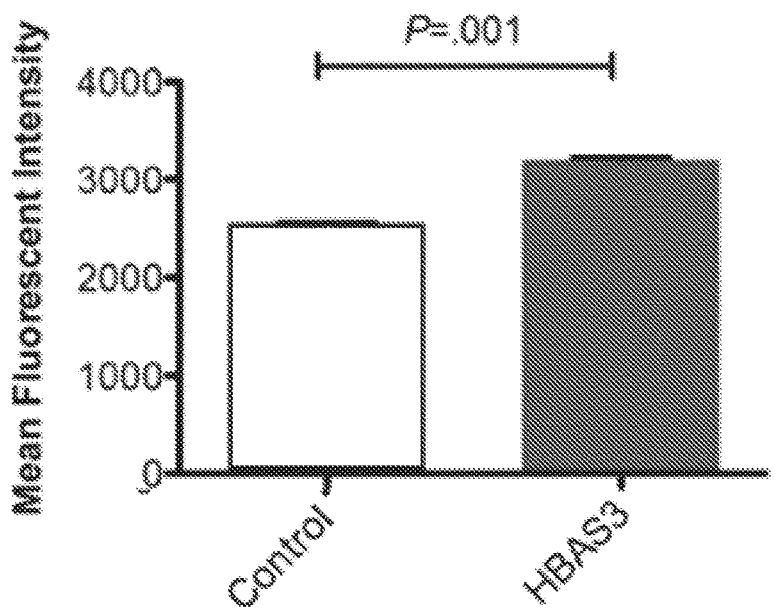
Figure 5L:
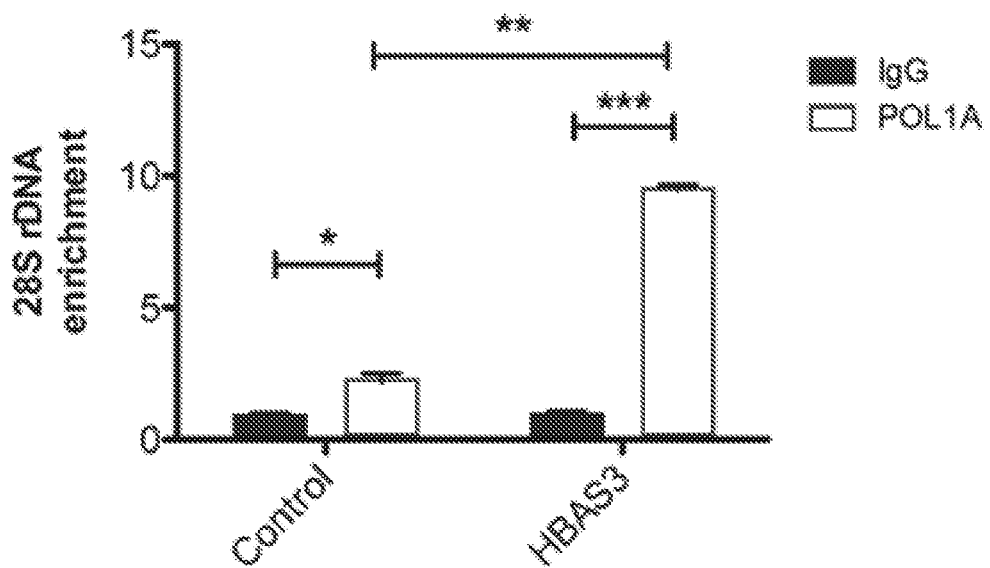
Figure 5M:
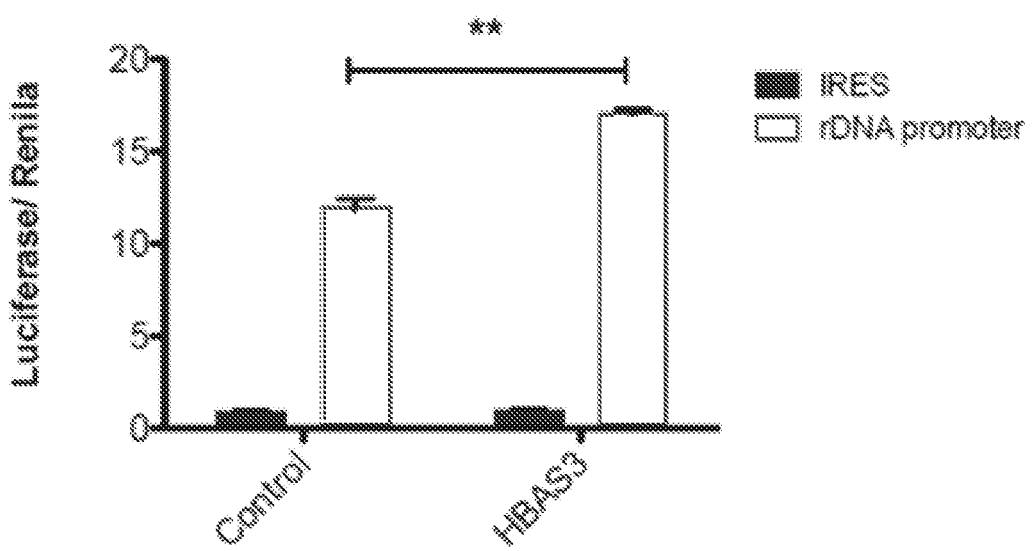

Inversely, overexpression of the HOXB-AS3 in K562 led to an increase in the formed EBP1-NPM1 complex, as shown by co-immunoprecipitation experiments (FIG. 5H). In addition, overexpression of HOXB-AS3 led to an increase in the transcribed rRNA species, in comparison to empty vector control (FIG. 5I; P<0.05). Overexpression of HOXB-AS3 also led to increased occupancy of the rDNA promoter by POL1RA when compared to control (FIG. 5L; P<0.001). To further validate these observations, experiments were performed with a luciferase reporter vector of POL1RA activity as described by Ghoshal et al. (Ghoshal K, Majumder S, Datta J et al. Role of Human Ribosomal RNA (rRNA) Promoter Methylation and of Methyl-CpG-binding Protein MBD2 in the Suppression of rRNA Gene Expression, *J Biol Chem.* 2004; 279(8):6783-6793). In brief, a region of 800 nucleotides of the ribosomal DNA promoter sequence was ligated into a luciferase reporter of promoter activity, which was modified to minimize interference by RNA-polymerase II-mediated transcription. K562 cells transfected with the rDNA promoter-containing luciferase vector showed an approximately 10-fold increase in the luciferase-to-renila ratio compared to cells transfected with empty vector controls. This increase was significantly higher when the K562 cells were concomitantly transfected with a HOXB-AS3 overexpressing vector versus a control empty vector (FIG. 5M; P<0.01). Finally, HOXB-AS3 overexpression led to an increase in the de novo protein synthesis of transfected K562 cells, as measured by OPP incorporation and subsequent fluorochrome labelling of the newly synthesized peptides (FIG. 5K; P=0.01).

To study whether the proliferation inducing effect of HOXB-AS3 overexpression is primarily mediated by its interaction with the EBP1-NPM1 protein complex, ERP1 (or NPM1) was concomitantly knocked down and HOXB-AS3 was overexpressed in K562 cells. NPM1 was shown to be indispensable for the proliferative phenotype that is induced by HOXB-AS3 overexpression, as its depletion abrogated this effect.

Figure 6A:
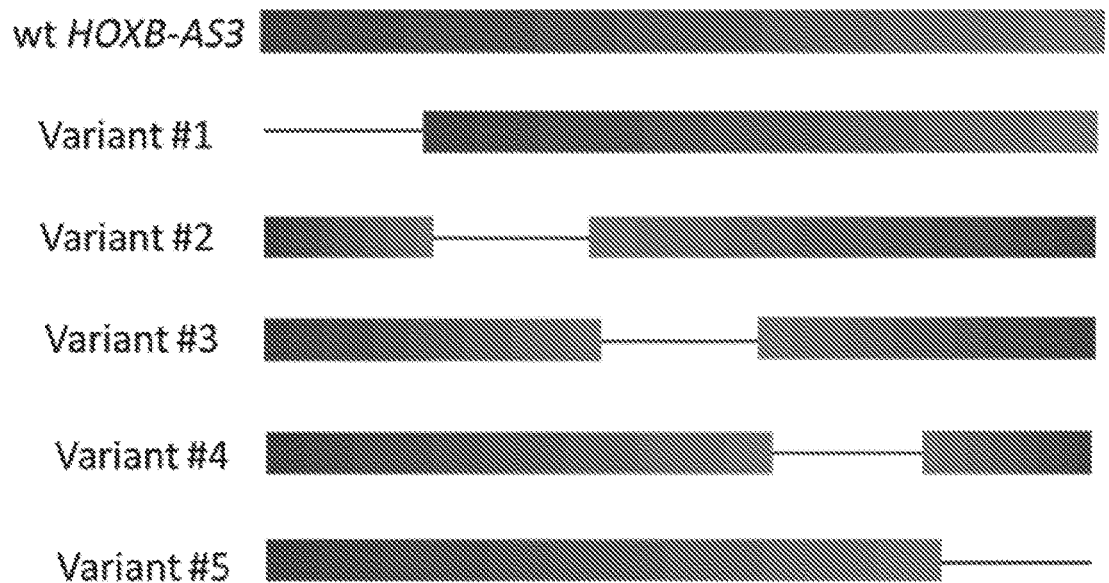
FIG. 6A-6B. Functional characterization of the HOXB-AS3 long non-coding RNA region which interacts with the EBP1 protein.
Figure 6B:
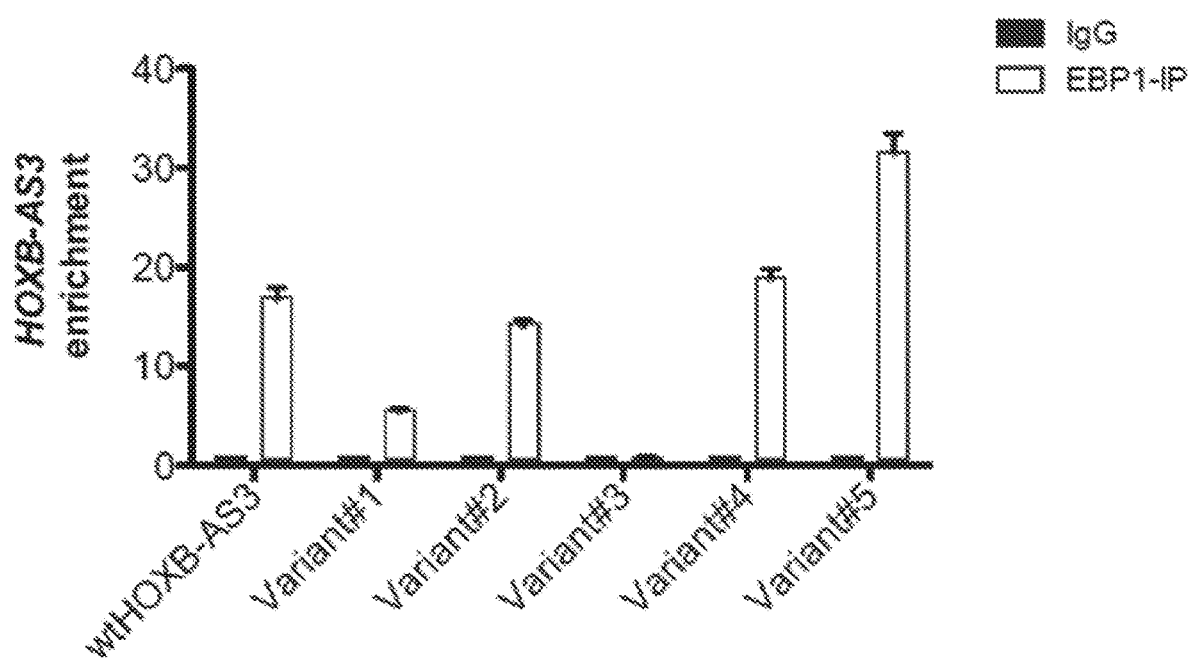

Identification of the Specific HOXB-AS3 Regions which Interact with the EBP1 and NONO Proteins To identify the specific regions of HOXB-AS3 that interact with the EBP1 protein, overlapping PCR experiments were performed to generate mutant variants of the HOXB-AS3 lncRNA. Specifically, 5 variants of the HOXB-AS3 lncRNA were generated, each of which was lacking 100 nucleotides when compared to the wt sequence (FIG. 6A). The primers used to generate the constructs are the following:

```
Primer Pair A:
Fw:
                                          (SEQ ID NO: 18)
5'-CAAGCTGGAATGGAGGAGGGGA-3'

Rev:
                                          (SEQ ID NO: 19)
5'-CGTCAGTTCCACTCGGTTGTC-3'

Primer Pair B:
Fw#1:
                                          (SEQ ID NO: 20)
5'-CAAGCTGGAATGGAGGAGGGGA-3'

Rev#1:
                                          (SEQ ID NO: 21)
5'-GAGCGAGGAGGAAGCCGAG-3'

Fw#2:
                                          (SEQ ID NO: 22)
5'-CGGCTTCCTCCTCGCTCTTATCTAAGC-3'

Rev#2:
                                          (SEQ ID NO: 23)
5'-TACGCTACGTAACGGCATGACAG-3

Primer Pair C:
Fw#1:
                                          (SEQ ID NO: 24)
5'-CAAGCTGGAATGGAGGAGGGGA-3'

Rev#1:
                                          (SEQ ID NO: 25)
5'-GGTTAGTGGCTCCATCTCCAGAC-3'

Fw#2:
                                          (SEQ ID NO: 26)
5'-GATGGAGCCACTAACCAACCAGGAG-3'

Rev#2:
                                          (SEQ ID NO: 27)
5'-TACGCTACGTAACGGCATGACAG-3'

Primer Pair D:
Fw#1:
                                          (SEQ ID NO: 28)
5'-CAAGCTGGAATGGAGGAGGGGA-3'

Rev#1:
                                          (SEQ ID NO: 29)
5'-GGTTGTGCAAGTGAGTGCCGA-3'

Fw#2
                                          (SEQ ID NO: 30)
5'-CACTTGCACAACCGAGTGGAACTG-3'

Rev#2:
                                          (SEQ ID NO: 31)
5'-TACGCTACGTAACGGCATGACAG-3'

Primer Pair E:
Fw:
                                          (SEQ ID NO: 32)
5'-CTCGGCTTCCTCCTCACCAGC-3'

Rev:
                                          (SEQ ID NO: 33)
5'-TACGCTACGTAACGGCATGACAG-3'
```

Primer pairs A, B, C, D and E were used for the generation of the mutant variants 1, 2, 3, 4 and 5 respectively. Overexpression experiments were performed with the wt and mutant HOXB-AS3 variants in K562 cells followed by RIPs with an EBP1-binding antibody and RT-PCRs assays specifically designed to measure the expression levels of each HOXB-AS3 variant. Deletion of the region between nucleotides 200 and 300 of the HOXB-AS3 lncRNA significantly reduced the amount of the lncRNA that is bound by EBP1 and identified this region as the primary site of the EBP1-HOXB-AS3 interaction. Consistently, transfection of K562 cells with the mutant variants of HOXB-AS3 did not affect the proliferation rate of K562 cells or the transcription of rRNA species.

Discussion

Deregulation of lncRNA expression is gaining gradual recognition for its important role in leukemogenesis. Previous work in cohorts of younger adults and older patients with CN-AML has identified a lncRNA which strongly associates with the presence of NPM1 mutations, named HOXB-AS3. In the example here, a series of experiments were performed to show that there is a causal relationship of the HOXB-AS3 and the presence of NPM1 mutations. In fact, transcript quantification by RNA sequencing analyses showed that HOXB-AS3 is the most aberrantly overexpressed gene of the HOXB cluster in OCI-AML3 cells and is expressed at similar levels with the protein coding HOXA9 and HOXA10.

Despite the association with the aberrant activation of the HOXB locus and the functional role of other HOX-locus embedded lncRNAs, depletion of HOXB-AS3 did not have an effect on the of HOX mRNA or HOX protein levels at the time when its effect on cell proliferation was observed.

The interactions of HOXB-AS3 with the proteome of OCI-AML3 cells were investigated and it was found that the HOXB-AS3 strongest interactor was the EBP1 protein. EBP1 has been shown to interact with NPM1 and to regulate transcription of rRNA species and ribosome biogenesis. It was shown here that HOXB-AS3 affects the interaction of EBP1 with NPM1; when OCI-AML3 cells were depleted of HOXB-AS3, a lesser amount of NPM1 was found to interact and could be co-immunoprecipitated with EBP1 and vice versa. Furthermore, it was found that the depletion of HOXB-AS3 impacts on the rRNA transcription, the ribosome biogenesis and, subsequently to the protein synthesis capacity of the cells. This is consistent with the impact of HOXB-AS3 manipulations on the proliferating capacity of the leukemic blasts as the amounts of transcribed rRNA has been shown to affect cell cycle progression of cells. In this sense, the functional role of HOXB-AS3, in the context of NPM1 mutations could be regarded as a compensatory mechanism which allows the leukemic blasts to maintain adequate amounts of ribosomal RNA and maximize the efficiency of the protein translating machinery in the metabolically demanding state of constant proliferation. Compatible with this scenario are unpublished Observation in CRISPRi-modified OCI-AML3 cells; the deletion of the NPM1 mutant allele, which results to a frank NPM1 haploinsufficiency and downregulation of HOXB-AS3 expression, leads to decreased rRNA transcription and ribosome biogenesis.

EBP1 is the protein most avidly binding to HOXB-AS3 in OCI-AML3 cells. Additional proteins which mediate key cellular functions were also identified and validated as HOXB-AS3 interactors. RNAseq analyses focused on the protein-coding fraction of the transcriptome revealed that the pathways of DNA-damage response could be affected by aberrant HOXB-AS3 expression. While it is likely that HOXB-AS3 exerts more than one function, depletion of either EBP1 or NPM1 abrogated the proliferative phenotype that is induced by HOXB-AS3 overexpression. These findings indicate that the effects of HOXB-AS3 manipulation on the proliferating capacity of leukemic blasts is primarily mediated by its interaction with EBP1. and NPM1 protein complex and the subsequent regulation of rRNA abundance and ribosome biogenesis.

As in vitro experiments delineate the significance of HOXB-AS3 expression in NPM1mut AML, HOXB-AS3 was also targeted in preclinical in vivo models for therapeutic use. An additional reason for this is the validated absence of HOXB-AS3 expression in healthy hematopoietic BM cells. A liposome-based method for packaging and delivering in vivo HOXB-AS3 targeting gapmers was used with no significant toxicities. Importantly in vivo knock down of HOXB-AS3 led to significant prolongation of the overall survival of mice xenografted with AML blasts of two different patients. In particular, in xenografts of one patient, HOXB-AS3 depletion led to eradication of the disease in a significant number of treated mice. This is the first known patient derived xenograft model in which in vivo depletion of a lncRNA shows therapeutic effects against AML as a single agent therapy.

Sequences

The Symbols used in the Sequences are as Follows:

iMe-dC: This refers to a deoxyCytidine that is substituted with a Methyl-deoxyCytidine.
+: Locked nucleic acid-modified bases,
*: Phosphorothioated bonds among bases.

```
LNA#1                                                                (SEQ ID NO: 1)
+C*+G*G*/iMe-dC/G*C*A*T*/iMe-dC/G*A*G*A*T*C*+G*+C

LNA#2                                                                (SEQ ID NO: 2)
+G*+G*A*G*G*G*A*A*T*T*G*T*A*G*+C*+G*+A

LNA#3                                                                (SEQ ID NO: 3)
+T*+G*/ImE-dC/G*T*T*G*T*A*T*T*G*G*T*A*T*G*+G*+G

LNA#4                                                                (SEQ ID NO: 4)
+G*+G*G*G*A*G*G*T*T*A*T*T*T*C*+G*+T*+T

LNA#5                                                                (SEQ ID NO: 5)
+T*+T*+C*T*A*T*T*A*C*T*T*G*/iMe-dC/*G*T*T*G*+T*+A

Negative Control                                                     (SEQ ID NO: 6)
+C*+G*+A*A*T*A*G*T*T*A*G*T*A*+G*+C*+G NR_033201.2                                                          (SEQ ID NO: 7)
    1 gtcatagcga cttttgggat agtttgctat cgacaaaggg agacaaagtc aagggggtgaa
   61 gggaaaggag ggccaagtag agcctccacg accctcggct tcctcctcac cagctccccc
  121 tccctccaag tccagtaaga agttgggcca agctggaagg gattgaccgg ccgtttcctc
  181 tccctcgccg gcctcggcgg agattccagg ccctatagaa accaggacgt cccttagcgc
  241 caccgcctca catgccagtg ctgccgggaa cccagcgata tccgcaccag cggagaaggt
  301 tccaggctgc cggcggcggc gcagagagcg ggaagagagg ctcggaggaa gccccgggcg
  361 tggcgtggtc aggctccgag agcggccggg atgcggccac accggcctgg taaactcgca
  421 cctcttagga tcttgctccc ggactcattc ccttccccac cccctatttt aaagttttat
  481 ttgggtcgtc tgtatcaatt tagaacgaga taaattaaga caaagaaagt aaaataaatc
  541 gaaataaaat ataggaatag ctcttggcga aaaaaaaaa aaaaaaaaa aaaaaaaaa
  601 aaaaaaaaa a NR_033202.2                                                          (SEQ ID NO: 8)
    1 gtcatagcga cttttgggat agtttgctat cgacaaaggg agacaaagtc aagggggtgaa
   61 gggaaaggag ggccaagtag agcctccacg accctcggct tcctcctcac cagctccccc
  121 tccctccaag tccagtaaga agttgggcca agctggaagg gattgaccgg gttgcttgtc
  181 tggagatgga gccactacag gcgggcctgg gcgcctggag tcgggcatga aagaaaatag
  241 cgcctcatcg ctcttatcta agcccagagg tagacttcgc ttgaaaagat cgagaatgga
  301 ggaggggatc ggcactcact tgcagacatc aacagtttcc agaaaattcg gttcaattcc
  361 ttcaccacgg acccaccaac caaggagctg gcaaacccca ctaaccaacc aggagaacac
```

```
421  agacccggtt tgtcttttga caaccgagtg gaactgacgg ggccggcgcc tgccctgcgg 481  gtccctccc ttggctgaga agaaaaccaa ataaaccttg aacagccttg gcttcgaaaa 541  aaaaaaaaa
```

NR_033203.1                                                                (SEQ ID NO: 9)

```
  1  ggaaccagat cttgatctgg cgctcggaca ggcagagtgc gtgggcgatc tcgatgcgcc 61  gtcgccgggt caggttgctt gtctggagat ggagccacta caggcgggcc tgggcgcctg 121  gagtcgggca tgaaagaaaa tagcgcctca tcgctcttat ctaagcccag aggtagactt 181  cgcttgaaaa gatcgagaat ggaggagggg atcggcactc acttgcagac atcaacagtt 241  tccagaaaat tcggttcaat tccttcacca cggacccacc aaccaaggag ctggcaaaac 301  ccactaacca accaggagaa cacagacccg gtttgtcttt tgacaaccga gtggaactga 361  cggggccggc gcctgccctg cgggtcccct cccttggctg agaagaaaac caaataaacc 421  ttgaacagcc ttggcttcga aaaaaaaaaa aa
``` us60gwg.1                                                                (SEQ ID NO: 10)

```
cagtttccagaaaattcggttcaattccttcaccacggacccaccaaccaaggagctggcaaaacccactaaccaac caggagaacacagacccgccgtttcctctccctcgccggcctcggcggagattccaggccctatagaaaccaggacg tcccttagcgccaccgcctcacatgccagtgctgccgggaacccagcgatatccgcaccagcggagaaggttccagg ctgccggcggcggcgcagagagcgggaagagaggctcggaggaagccccgggcgtggcgtggtcaggctccgagagc ggccgggatgcggccacaccggcctggtaaactcgcacctcttaggatcttgctcccggactcattcccttccccac cccctattttaaagttttatttgggtcgtctgtatcaatttagaacgagataaattaagacaaagaaagtaaaataa atcgaaataaaatata
```

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A single stranded oligomer, wherein the oligomer is perfectly complementary to a corresponding region of HOXB-AS3 non-coding RNA, wherein the oligomer comprises at least one nucleotide analogue having a modified sugar moiety, wherein the at least one nucleotide analogue having a modified sugar moiety comprises a Locked Nucleic Acid, and wherein the oligomer is between 15-25 nucleotides.

2. The oligomer of claim 1, wherein the oligomer further comprises a modified phosphodiester linkage.

3. The oligomer of claim 2, wherein the modified phosphodiester linkage comprises a phosphorothioate bond.

4. The oligomer of claim 1, wherein the HOXB-AS3 non-coding RNA has the nucleic acid sequence encoded by SEQ ID NO:7, SEQ ID NO:8, SEQ ID NO:9, or SEQ ID NO:10.

5. The oligomer of claim 1, wherein the oligomer comprises a nucleic acid sequence selected from SEQ ID NO:1, SEQ ID NO:2, SEQ ID NO:3, SEQ ID NO:4, SEQ ID NO:5, or a mixture thereof.

6. The oligomer of claim 5, wherein the oligomer comprises the nucleic acid sequence SEQ ID NO:2.

7. The oligomer of claim 5, wherein the oligomer comprises the nucleic acid sequence SEQ ID NO:3.

8. A method for treating acute myeloid leukemia comprising administering to a subject in need thereof a single stranded oligomer, wherein the oligomer is perfectly complementary to a corresponding region of HOXB-AS3 non-coding RNA, wherein the oligomer comprises at least one nucleotide analogue having a modified sugar, wherein the at least one nucleotide analogue having a modified sugar moiety comprises a Locked Nucleic Acid, and wherein the oligomer is between 15-25 nucleotides.

9. The method of claim 8, wherein the HOXB-AS3 non-coding RNA has the nucleic acid sequence encoded by SEQ ID NO:7, SEQ ID NO:8, SEQ ID NO:9, or SEQ ID NO:10.

10. The method of claim 8, wherein the oligomer comprises a nucleic acid sequence selected from SEQ ID NO:1, SEQ ID NO:2, SEQ ID NO:3, SEQ ID NO:4, SEQ ID NO:5, or a mixture thereof.

11. The method of claim 10, wherein the oligomer comprises the nucleic acid sequence SEQ ID NO:2.

12. The method of claim 10, wherein the oligomer comprises the nucleic acid sequence SEQ ID NO:3.

13. The method of claim 8, wherein the oligomer inhibits the expression of HOXB-AS3 non-coding RNA in a cell.

14. The method of claim 8, wherein the acute myeloid leukemia is cytogenetically normal AML (CN-AML).

15. A method of inhibiting the expression of HOXB-AS3 in a cell, comprising contacting the cell with an effective amount of a single stranded oligomer, wherein the oligomer is perfectly complementary to a corresponding region of HOXB-AS3 non-coding RNA, wherein the oligomer comprises at least one nucleotide analogue having a modified sugar moiety, wherein the at least one nucleotide analogue having a modified sugar moiety comprises a Locked Nucleic Acid, and wherein the oligomer is between 15-25 nucleotides.

16. The method of claim 15, wherein the cell is within a tissue of a mammal.

* * * * *